(12) United States Patent
Wisselink et al.

(10) Patent No.: US 9,353,376 B2
(45) Date of Patent: May 31, 2016

(54) PENTOSE AND GLUCOSE FERMENTING YEAST CELL

(75) Inventors: Hendrik Wouter Wisselink, Culemborg (NL); Antonius Jeroen Adriaan Van Maris, Delft (NL); Jacobus Thomas Pronk, Delft (NL)

(73) Assignee: DSM IP ASSETS, B.V., Heerlen (NL)

( * ) Notice: Subject to any disclaimer, the term of this patent is extended or adjusted under 35 U.S.C. 154(b) by 307 days.

(21) Appl. No.: 13/822,285

(22) PCT Filed: Oct. 11, 2011

(86) PCT No.: PCT/EP2011/067720
§ 371 (c)(1),
(2), (4) Date: Jun. 14, 2013

(87) PCT Pub. No.: WO2012/049170
PCT Pub. Date: Apr. 19, 2012

(65) Prior Publication Data
US 2013/0273601 A1 Oct. 17, 2013

Related U.S. Application Data

(60) Provisional application No. 61/392,617, filed on Oct. 13, 2010.

(30) Foreign Application Priority Data

Oct. 13, 2010 (EP) ..................................... 10075710

(51) Int. Cl.
| | |
|---|---|
| *C12P 7/10* | (2006.01) |
| *C12P 7/06* | (2006.01) |
| *C12P 7/16* | (2006.01) |
| *C12N 15/81* | (2006.01) |
| *C07K 14/395* | (2006.01) |
| *C12N 9/12* | (2006.01) |

(52) U.S. Cl.
CPC .............. *C12N 15/81* (2013.01); *C07K 14/395* (2013.01); *C12N 9/1205* (2013.01); *C12P 7/06* (2013.01); *C12P 7/10* (2013.01); *Y02E 50/16* (2013.01); *Y02E 50/17* (2013.01)

(58) Field of Classification Search
CPC combination set(s) only.
See application file for complete search history.

(56) References Cited

U.S. PATENT DOCUMENTS

2012/0208231 A1    8/2012    Van Maris et al.

FOREIGN PATENT DOCUMENTS

| WO | 2008/041840 | 4/2008 |
|---|---|---|
| WO | 2009/011591 | 1/2009 |
| WO | 2010/099153 | 9/2010 |
| WO | 2010/099343 | 9/2010 |
| WO | 2012/049173 | 4/2012 |

OTHER PUBLICATIONS

Kramarenko et al.; "Sugar Repression in the Methylotrophic Yeast Hansenula Polymorpha Studied by Using Hexokinase-Negative, Glucokinase-Negative and Double Kinase-Negative Mutants"; Folia Microbiol.; vol. 45; No. 6; 2000; pp. 521-529.
Diderich et al.; "Physiological Properties of *Saccharomyces cerevisiae* From Which Hexokinase II Has Been Deleted"; Applied and Environmental Microbiology; Apr. 2001; vol. 67; No. 4; pp. 1587-1593; American Society for Microbiology.
Raghevendran et al.; "Phenotypic Characterization of Glucose Repression Mutants of *Saccharomyces cerevisiae* Using Experiments With 13C-Labelled Glucose"; Yeast; vol. 21; 2004; pp. 769-779; John Wiley & Sons, Ltd.
Hahn-Haegerdal et al.; "Towards Industrial Pentose-Fermenting Yeast Strains"; Appl. Microbiol Biotechnol; 2007; vol. 74; pp. 937-953; Springer-Verlag.
Kuemmel et al.; "Differential Glucose Repression in Common Yeast Strains in Response to HXK2 Deletion"; FEMS Yeast Res; vol. 10; 2010; pp. 322-332; Federation of European Microbiology Societies; Blackwell Publishing Ltd.
Wisselink et al.; "Engineering of *Saccharomyces cerevisiae* for Efficient Anaerobic Alcoholic Fermentation of L-Arabinose"; Applied and Environmental Microbiology; Aug. 2007; vol. 73; No. 15; pp. 4881-4891; American Society for Microbiology.
Walsh et al.; "*Saccharomyces cerevisiae* Null Mutants in Glucose Phosphorylation: Metabolism and Invertase Expression"; Genetics; vol. 128; Jul. 1991; pp. 521-527; Genetics Society of America.
Wisselink et al; "Novel Evolutionary Engineering Approach for Accelerated Utilization of Glucose, Xylose, and Arabinose Mixtures by Engineered *Saccharomyces cerevisiae* Strains"; Applied and Environmental Microbiology; Feb. 2009; vol. 75; No. 4; pp. 907-914.
Wedlock et al.; "Glucose-Negative Mutants of Pachysolen Tannophilus"; Journal of General Microbiology; 1989; vol. 135; pp. 2019-2026; SGM.
Van Maris et al.; "Alcoholic Fermentation of Carbon Sources in Biomass Hydrolysates by *Saccharomyces cerevisiae*: Current Status"; 2006; vol. 90; pp. 391-418; Springer.
Wedlock et al.; "Transformation of a Glucose Negative Mutant of Pachysolen Tannophilus With a Plasmid Carrying the Cloned Hexokinase PII Gene From *Saccharomyces cerevisiae*"; Biotechnology Letters; vol. II; No. 9; 1989; pp. 601-604.
International Search Report Based on Application No. PCT/EP2011/067720 Mailed Apr. 17, 2012.
International Search Report & Written Opinion Based on Application No. PCT/EP2011/067726 Mailed Feb. 1, 2012.
Becker et al.; "A Modified *Saccharomyces cerevisiae* Strain That Consumes L-Arabinose and Produces Ethanol"; Applied and Environmental Microbiology; Jul. 2003; vol. 69; No. 7; pp. 4144-4150; American Society for Microbiology.

(Continued)

*Primary Examiner* — Kagnew H Gebreyesus
(74) *Attorney, Agent, or Firm* — McBee Moore Woodward & Vanik IP, LLC

(57) ABSTRACT

The present invention relates to a yeast cell comprising one or more exogenous genes of a pentose metabolic pathway non-native to the yeast cell wherein the yeast cell has a disruption of the hxk1, hxk2 glk1 and gal1 native in the yeast cell. The invention further relates to pentose and glucose fermenting yeast cell that is capable of simultaneous pentose and glucose consumption.

11 Claims, 30 Drawing Sheets

(56) References Cited

OTHER PUBLICATIONS

Wisselink et al.; "Metabolome, Transcriptome and Metabolic Flux Analysis of Arabinose Fermintation by Engineerined *Saccharomyces cerevisiae*"; Metabolic Engineering; vol. 12; 2010; pp. 537-551; Elsevier Inc.

Kasahara et al.; "Three Aromatic Amino Acid Residues Critical for Galactose Transport in Yeast GAL2 Transporter"; The Journal of Biological Chemistry; vol. 275; No. 6; Issue Feb. 11, 2000; pp. 4422-4428; The American Society for Biochemistry and Molecular Biology, Inc.

Raamsdonk et al.; "Co-Consumption of Sugars or Ethanol and Glucose in a *Saccharomyces cerevisiae* Strain Deleted in the HXK2 Gene"; Yeast; Aug. 2001; vol. 18; No. 11; pp. 1023-1033 (Abstract Only).

```
GAL1 CEN.PK      1 mtkshseevivpefnssakelprplaekcpsiikkfisaydakpdfvarspgrvnligeh
GAL1 IMK318     1 ............................................................
GAL1 IMW017     1 ............................................................
GAL1 IMW018     1 ............................................................

GAL1 CEN.PK     61 idycdfsvlplaidfdmlcavkvlneknpsitlinadpkfaqrkfdlpldgsyvtidpsv
GAL1 IMK318    61 ............................................................
GAL1 IMW017    61 ............................................................
GAL1 IMW018    61 ............................................................

GAL1 CEN.PK    121 sdwsnyfkcglhvahsflkklaperfasaplaglqvfcegdvptgsglsssaaficaval
GAL1 IMK318   121 ............................................................
GAL1 IMW017   121 ............................................................
GAL1 IMW018   121 ............................................................

GAL1 CEN.PK    181 avvkanmgpgyhmskqnlmritvvaehyvgvnnggmdqaasvcgeedhalyvefkpqlka
GAL1 IMK318   181 ............................................................
GAL1 IMW017   181 ............................................................
GAL1 IMW018   181 ............................................................

GAL1 CEN.PK    241 tpfkfpqlknheisfviantlvvsnkfetaptnynlrvvevttaanvlaatygvvlpsgk
GAL1 IMK318   241 ............................................................
GAL1 IMW017   241 .................................f..........................
GAL1 IMW018   241 ............................................................

GAL1 CEN.PK    301 egsstnkgnlrdimnvyyaryhnistpwngdiesgierltkmlvlveeslankkqgfsvd
GAL1 IMK318   301 ............................................................
GAL1 IMW017   301 ............................................................
GAL1 IMW018   301 ............................................................

GAL1 CEN.PK    361 dvaqslncsreeftrdylttspvrfqvlklyqrakhvyseslrvlkavklmttesftade
GAL1 IMK318   361 ...............v............................................
GAL1 IMW017   361 ...............v............................................
GAL1 IMW018   361 ...............v............................................

GAL1 CEN.PK    421 dffkqfgalmnesqascdklyecscpeidkicsialsngsygsrltgagwggctvhlvpg
GAL1 IMK318   421 ............................................................
GAL1 IMW017   421 ............................................................
GAL1 IMW018   421 ............................................................

GAL1 CEN.PK    481 gpngniekvkealanefykvkypkitdaelenaiivskpalgsclyel
GAL1 IMK318   481 ................................................
GAL1 IMW017   481 ................................................
GAL1 IMW018   481 ................................................
```

Fig.19

```
GAL2 CENPK AA      1 maveennmpvvsqqpqagedvisslskdshlsaqsqkysndelkagesgpegsqsvpiei
GAL2 IMK318 AA     1 ............................................................
GAL2 IMW017 AA     1 ............................................................
GAL2 IMW018 AA     1 ............................................................

GAL2 CENPK AA     61 pkkpmseyvtvsllclcvafggfmfgwdtgtisgfvvqtdflrrfgmkhkdgthylsnvr
GAL2 IMK318 AA    61 ............................................................
GAL2 IMW017 AA    61 ............................................................
GAL2 IMW018 AA    61 ............................................................

GAL2 CENPK AA    121 tglivaifnigcafggiilskggdmygrkkglsivvsvyivgiiiqiasinkwyqyfigr
GAL2 IMK318 AA   121 ............................................................
GAL2 IMW017 AA   121 ............................................................
GAL2 IMW018 AA   121 ............................................................

GAL2 CENPK AA    181 iisglgvggiavlcpmliseiapkhlrgtlvscyqlmitagiflgyctnygtksysnsvq
GAL2 IMK318 AA   181 ............................................................
GAL2 IMW017 AA   181 ..............................n.............................
GAL2 IMW018 AA   181 ............................................................

GAL2 CENPK AA    241 wrvplglcfawslfmigaltlvpespryclcevnkvedaklsiaksnkvspedpavqaeld
GAL2 IMK318 AA   241 ............................................................
GAL2 IMW017 AA   241 ............................................................
GAL2 IMW018 AA   241 ............................................................

GAL2 CENPK AA    301 limagieaeklagnaswgelfstktkvfqrllmgvfvqmfqqltgnnyffyygtvifksv
GAL2 IMK318 AA   301 ............................................................
GAL2 IMW017 AA   301 ............................................................
GAL2 IMW018 AA   301 ............................................................

GAL2 CENPK AA    361 glddsfetsivigvvnfastffslwtvenlgrrkclllgaatmmacmviyasvgvtrlyp
GAL2 IMK318 AA   361 ............................................................
GAL2 IMW017 AA   361 ............................................................
GAL2 IMW018 AA   361 ...............s............................................

GAL2 CENPK AA    421 hgksqpsskgagncmivftcfyifcyattwapvawvitaesfplrvkskcmalasasnwv
GAL2 IMK318 AA   421 ............................................................
GAL2 IMW017 AA   421 ............................................................
GAL2 IMW018 AA   421 ............................................................

GAL2 CENPK AA    481 wgfliafftpfitsainfyygyvfmgclvamffyvfffvpetkglsleeiqelweegvlp
GAL2 IMK318 AA   481 ............................................................
GAL2 IMW017 AA   481 ............................................................
GAL2 IMW018 AA   481 ............................................................

GAL2 CENPK AA    541 wksegwipssrrgnnydledlqhddkpwykamle
GAL2 IMK318 AA   541 .................................
GAL2 IMW017 AA   541 .................................
GAL2 IMW018 AA   541 .................................
```

Fig. 20

PENTOSE AND GLUCOSE FERMENTING YEAST CELL

CROSS REFERENCE TO RELATED APPLICATIONS

This application is a §371 National Stage Application of PCT/EP2011/067720 filed Oct. 11, 2011, which claims priority to European Application No. 10075710.3 filed Oct. 13, 2010 and U.S. Provisional Application No. 61/392,617, filed Oct. 13, 2010.

BACKGROUND OF THE INVENTION

1. Field of the Invention

The invention relates to a pentose and glucose fermenting yeast cell, suitable for fermentation of a sugar composition comprising C5 and C6 sugar(s) (such composition is herein also designated as the mixed sugar composition). The mixed sugar composition may originate from ligno-cellulosic material. The invention also relates to a process for the production of fermentation product from the mixed sugar composition using the pentose and glucose fermenting yeast cell.

2. Description of Related Art

Most of the ethanol produced as alternative for fossil fuels is currently from fermentation of corn starch and sugar cane based sucrose. In order to reach the ambitious goals for producing renewable fuels, new technologies are being developed for converting non-food biomass into fermentation products such as ethanol. *Saccharomyces cerevisiae* is the organism of choice in the ethanol industry, but it cannot utilize five-carbon sugars contained in the hemicellulose component of biomass feedstocks. Hemicellulose can make up to 20-30% of biomass, with xylose and arabinose being the most abundant C5 sugars. Heterologous expression of a xylose isomerase (XI) is an option for enabling yeast cells to metabolize and ferment xylose. Likewise, expression of bacterial genes araA, araB, and araD in *S. cerevisiae* strains results in utilization and efficient alcoholic fermentation of arabinose.

Fermentation of pentose to ethanol by known pentose-fermenting yeast species occurs slowly and results in low yields relative to fermentation rates and ethanol yields that are obtained with conventional yeasts in glucose fermentations. In order to improve the cost effectiveness of the pentose fermentation, it is necessary to increase the rate of fermentation and the ethanol yields obtained.

*S. cerevisiae* has an inherent preference for glucose. As a consequence, all current pentose fermenting strains demonstrate sequential utilisation of mixtures of glucose and pentoses or at best the pentose fermentation starts at low glucose concentrations.

WO2008041840 describes an eukaryotic cell expressing nucleotide sequences encoding the ara A, ara B and ara D enzymes whereby the expression of these nucleotide sequences confers on the cell the ability to use L-arabinose and/or convert L-arabinose into L-ribulose, and/or xylulose 5-phosphate and/or into a desired fermentation product such as ethanol. Optionally, the eukaryotic cell is also able to convert xylose into ethanol. The strain IMS0003 (page 46) is able to completely consume within 70 hours, glucose, xylose and arabinose, as shown in FIG. 7. FIG. 7 shows that substantial consumption of xylose and arabinose only starts after 20 hours, i.e. when the glucose has already be completely converted. The consumption of glucose and pentose is sequential.

Raamsdonk L M et al., Yeast 2001; 18; 1023-1003 describe co-consumption of sugars or ethanol and glucose in a *Saccharomyces cerevisiae* strain deleted in the HXK2 gene. However the strain hardly produced ethanol and grows almost exclusively oxidatively in the presence of abundant glucose.

It would be desirable to provide a yeast strain that can an-aerobically ferment pentose either simultaneous with glucose (co-fermentation of pentose and glucose) and/or faster than is known.

SUMMARY

It is an object of the invention to provide a yeast strain that can an-aerobically co-ferment pentose and glucose.

It is an object of the present invention to provide a cost-effective method of producing ethanol by fermentation of pentose.

It is another object of the present invention to provide a yeast cell that is capable of fermenting pentose at a higher rate than can be achieved using strains currently known to the art.

It is another object to reduce the fermentation time of C5/C6 fermentation.

Other objects, features, and advantages of the invention will be apparent from review of the specification and claims.

One or more of these objects are obtained according to the invention. One embodiment of the invention is a Yeast cell comprising one or more exogenous genes of one or more pentose metabolic pathway non-native to the yeast cell wherein the yeast cell has a disruption of the hxk1, hxk2 glk1 and gal1 native in the yeast cell.

Such a cell with one or more disruption(s) is herein designated as disruptant yeast cell. The cell with disruption of the hxk1, hxk2, glk1 and gal1 is herein also called quadruple disruptant.

The invention further relates to a process for preparation of a pentose fermenting yeast cell, wherein a yeast cell comprising one or more exogenous genes of a pentose pathway is subjected to disruption of the gene hxk2 native in the yeast cell, wherein the resulting disruptant yeast cell is subjected to evolutionary engineering to improve pentose consumption, until the yeast cell has growth rate of $0.05\ h^{-1}$ or more on the pentose as sole carbon source and isolating the resulting pentose fermenting yeast cell. In an embodiment, the pentose fermenting yeast cell is not able to consume glucose. The cell that is the product of the evolutionary engineering is herein designated as pentose fermenting yeast cell.

In a preferred embodiment of this process, the disruptant cell is a yeast cell comprising one or more exogenous genes that allow the cells to ferment pentose wherein the cell has a disruption of hxk1, hxk2 glk1 and gal1 native in the yeast cell, i.e. is a quadruple disruptant.

In an embodiment the pentose fermenting yeast cell comprises one or more exogenous hexokinase. By reintroduction of hexokinase activity through an exogenous hexokinase, the glucose consumption by the pentose fermenting yeast cell may be restored. Preferably the exogenous hexokinase(s) have the same activity as the hexokinase(s) native in yeast cell. Such yeast cell in which hexokinase has been reintroduced is herein designated as pentose and glucose fermenting yeast cell or yeast cell. The invention further relates to a pentose and glucose fermenting *Saccharomyces* cell that is capable of anaerobic simultaneous pentose and glucose consumption.

Figure 1:
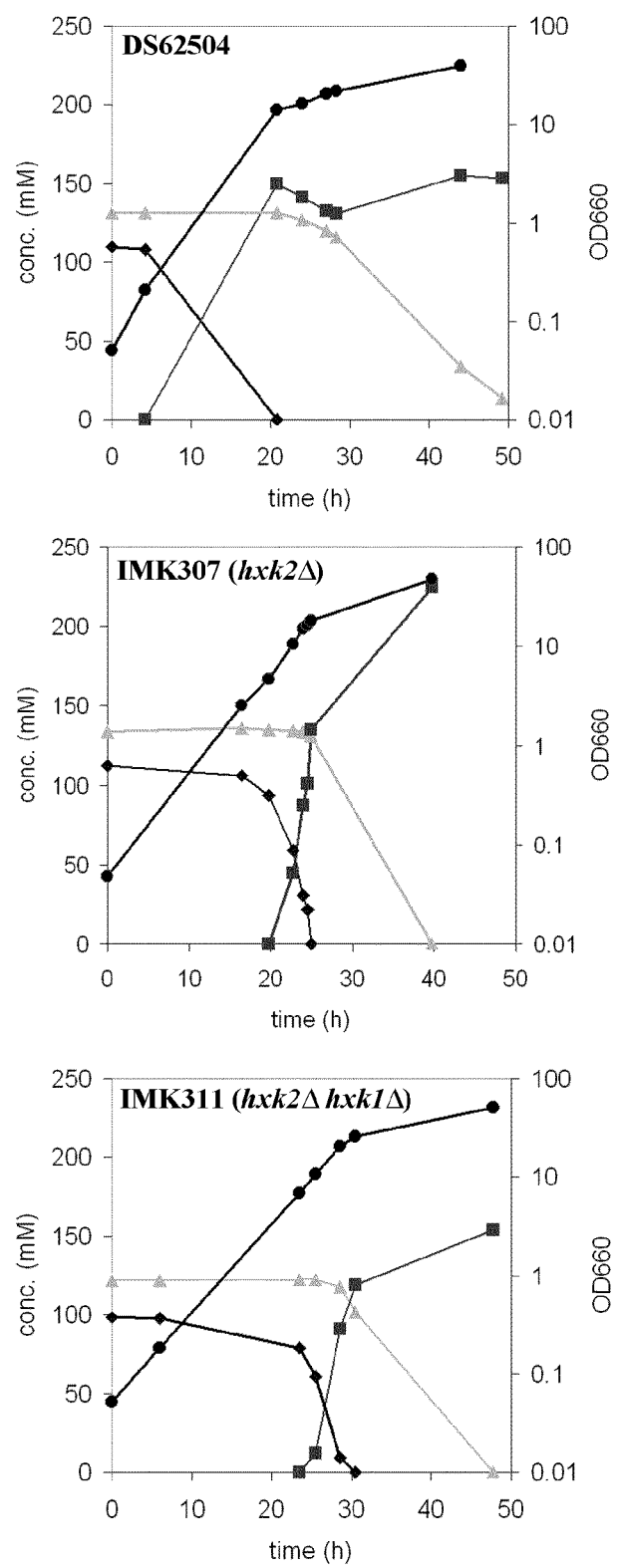
FIG. 1 shows glucose (♦), arabinose (▲) and ethanol (■) concentrations and optical density at 660 nm (OD660, ●)

during shake flask cultivations of strains DS62504 (FIG. 1 (a)), IMK307 (FIG. 1 (b)) and IMK311 (FIG. 1 (c)).

Figure 2:
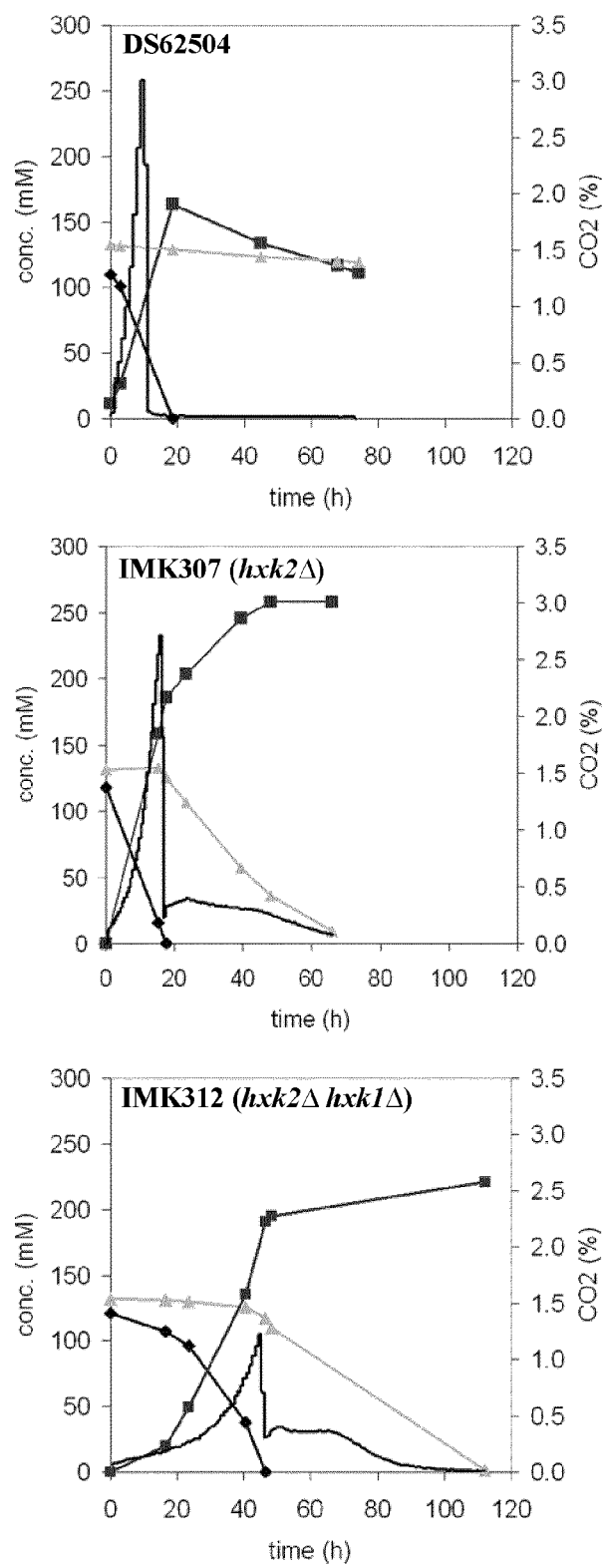

FIG. 2 shows glucose (♦), arabinose (▲) and ethanol (■) concentrations and $CO_2$ percentage in the exhaust gas (solid black line) during anaerobic cultivations of strains DS62504 (FIG. 2 (a)), IMK307 (FIG. 2 (b)) and IMK311 (FIG. 2 (c)). Fermentations were inoculated with glucose-grown shake flask cultures.

Figure 3:
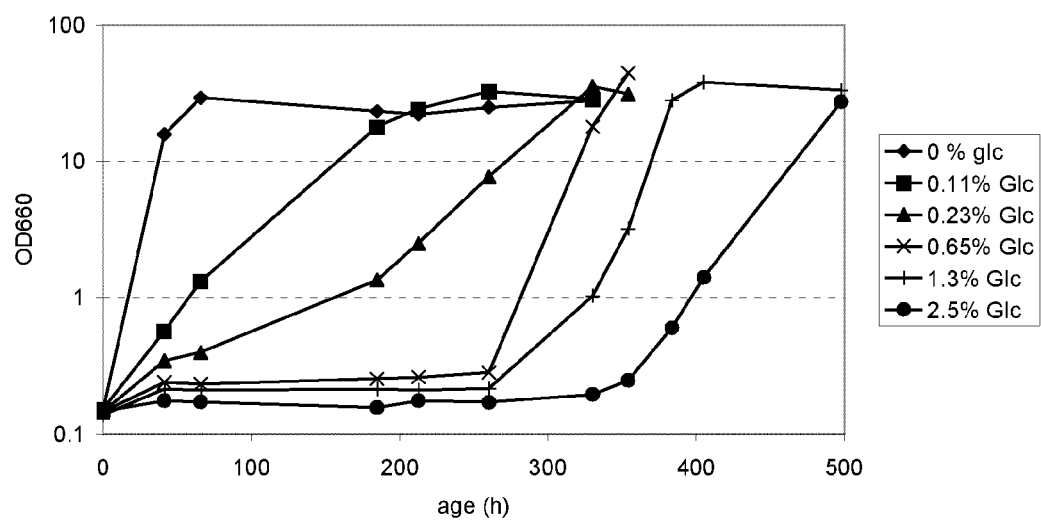

FIG. 3 shows growth profiles determined by measuring optical density at 660 nm (OD660) for shake flask cultivations of strain IMK318 in MYurea containing 2% arabinose and various concentrations of glucose (0, 0.11, 0.23, 0.65, 1.3 and 2.5%)

Figure 4:
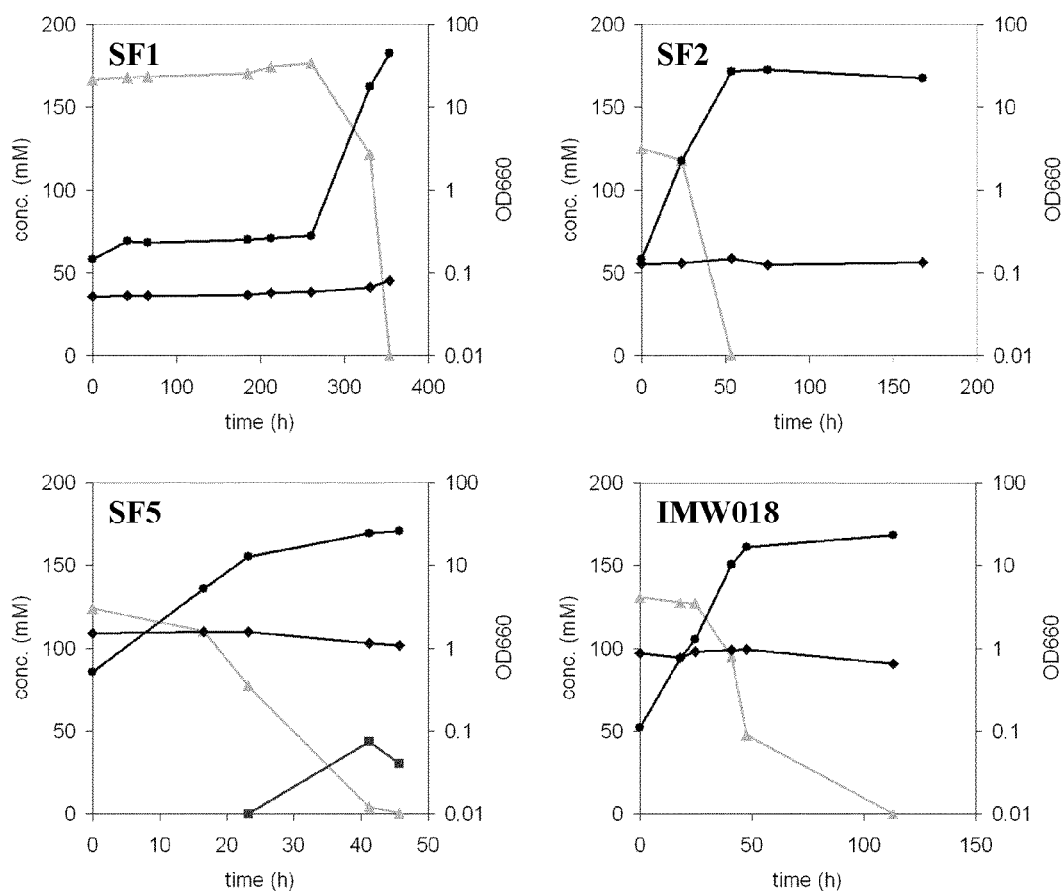

FIG. 4 Glucose (♦), arabinose (▲) and ethanol (■) concentrations and optical density at 660 nm (OD660, ●) during shake flask cultivations of: strain IMK318, serially transferred according to table 3 (Series A: SF1, SF2 and SF5); the single colony isolate selected from this series of shake flasks, IMW018.

Figure 5:
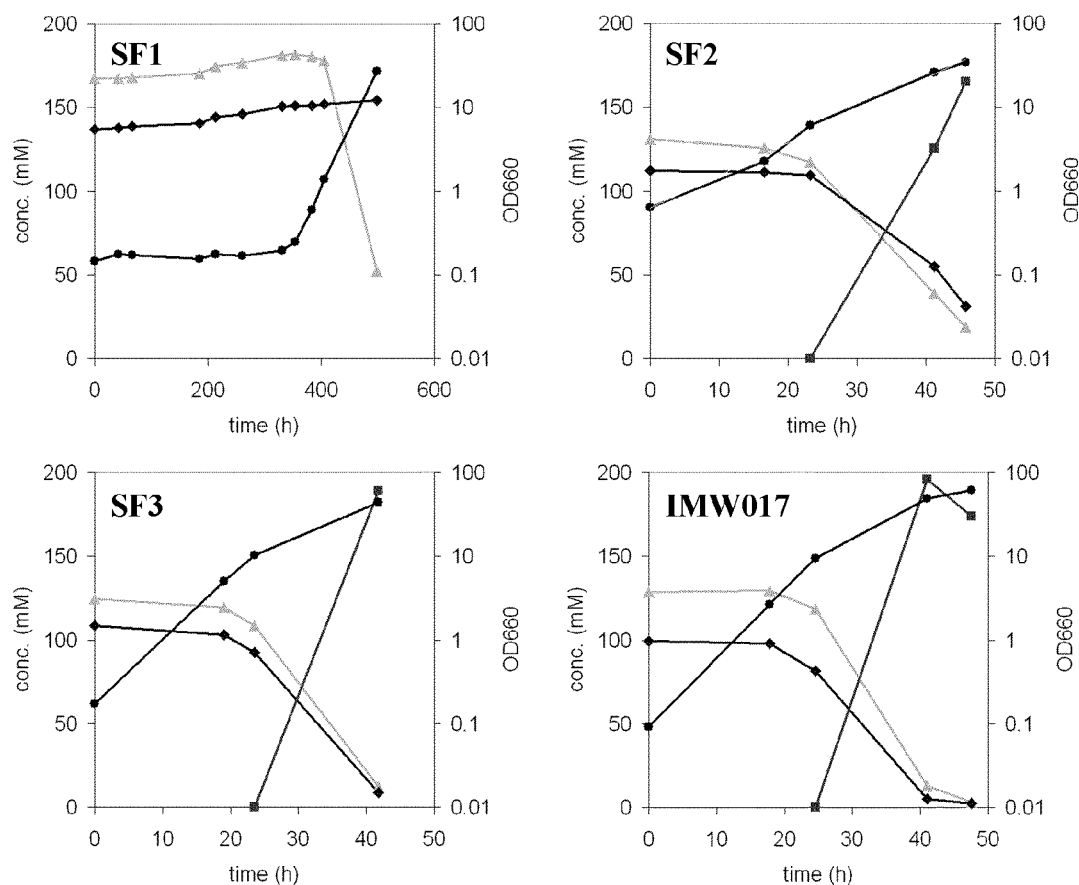

FIG. 5 shows glucose (♦), arabinose (▲) and ethanol (■) concentrations and optical density at 660 nm (OD660, ●) during shake flask cultivations of: strain IMK318, serially transferred according to table 3 (Series B: SF1, SF2 and SF3); the single colony isolate selected from this series of shake flasks, IMW017.

Figure 6:
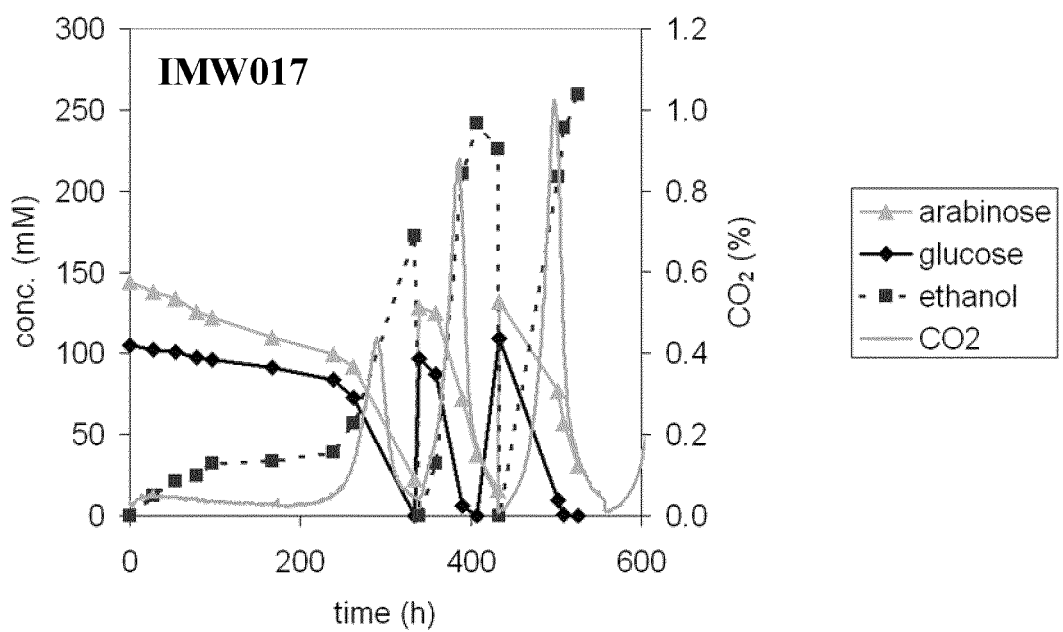

FIG. 6 shows glucose (♦), arabinose (▲) and ethanol (■) concentrations and $CO_2$ percentage in the exhaust gas (solid gray line) during sequential anaerobic cultivations of strain IMW017.

Figure 7:
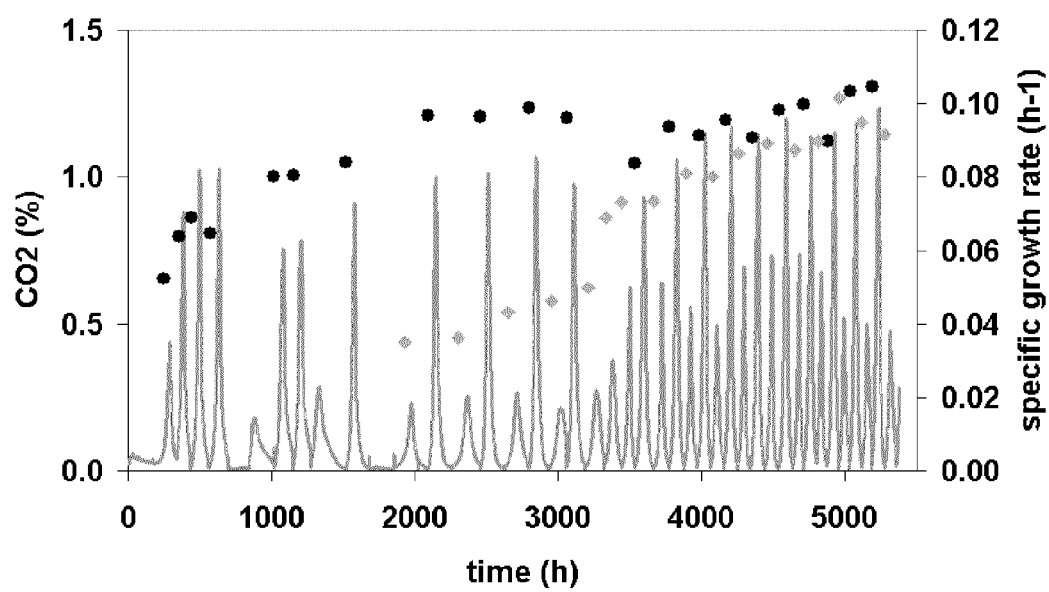

FIG. 7 shows $CO_2$ percentage in the exhaust gas (solid gray line) and growth rates during sequential anaerobic cultivations of strain IMW017. The specific growth rates are derived from the $CO_2$ production profile during the batch cultivations on either the mixture of glucose and arabinose (▲) or arabinose only (▲).

Figure 8:
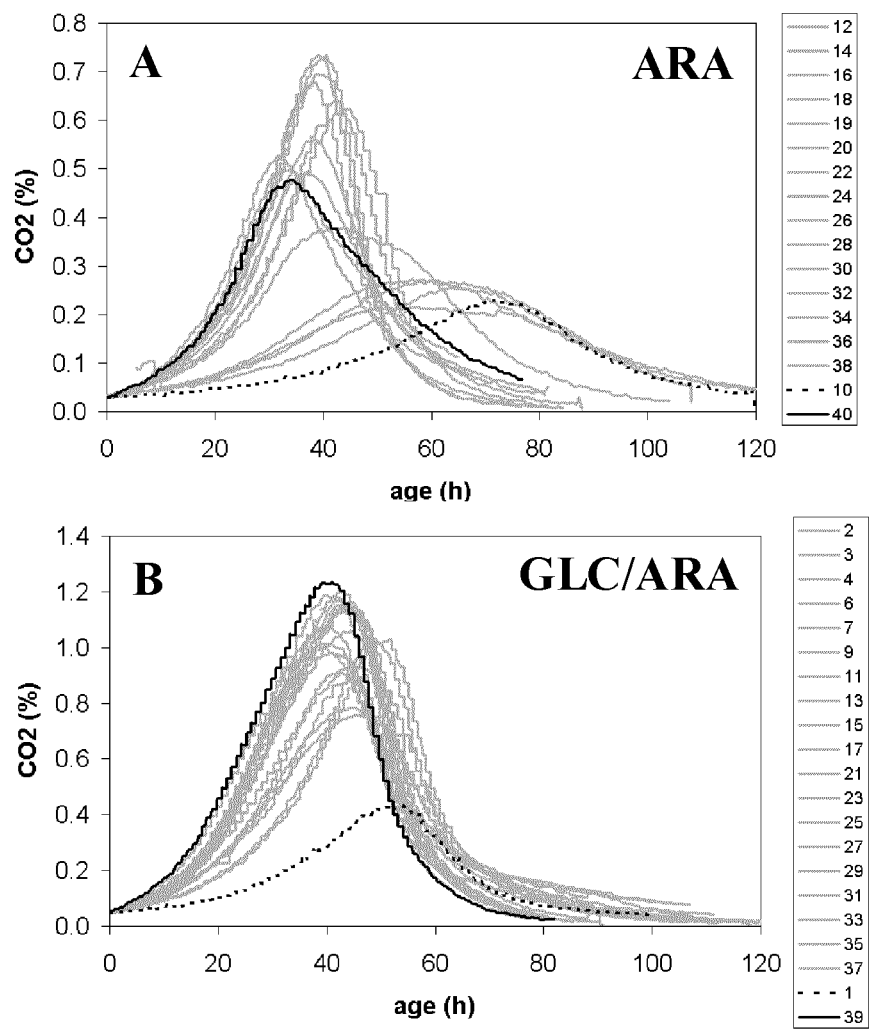

FIG. 8 shows the $CO_2$ production profiles of the individual batches in medium supplied with arabinose (A) and a mixture of glucose and arabinose (B) during anaerobic sequential batch cultivation of strain IMW017. The $CO_2$ production profiles are aligned assuming an equal initial $CO_2$ production level. The numbers in the legend indicate the consecutive batch numbers.

Figure 9:
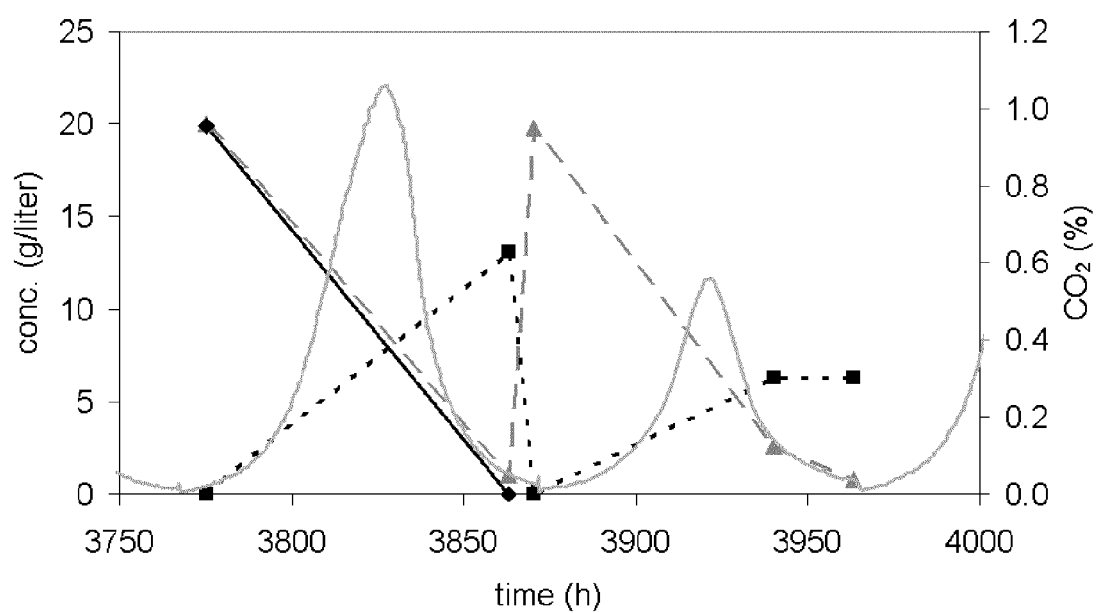

FIG. 9 shows glucose (♦), arabinose (▲) and ethanol (■) concentrations and $CO_2$ percentage in the exhaust gas (solid gray line) during batches 24 and 25 of the sequential anaerobic batch cultivation of strain IMW017.

Figure 10:
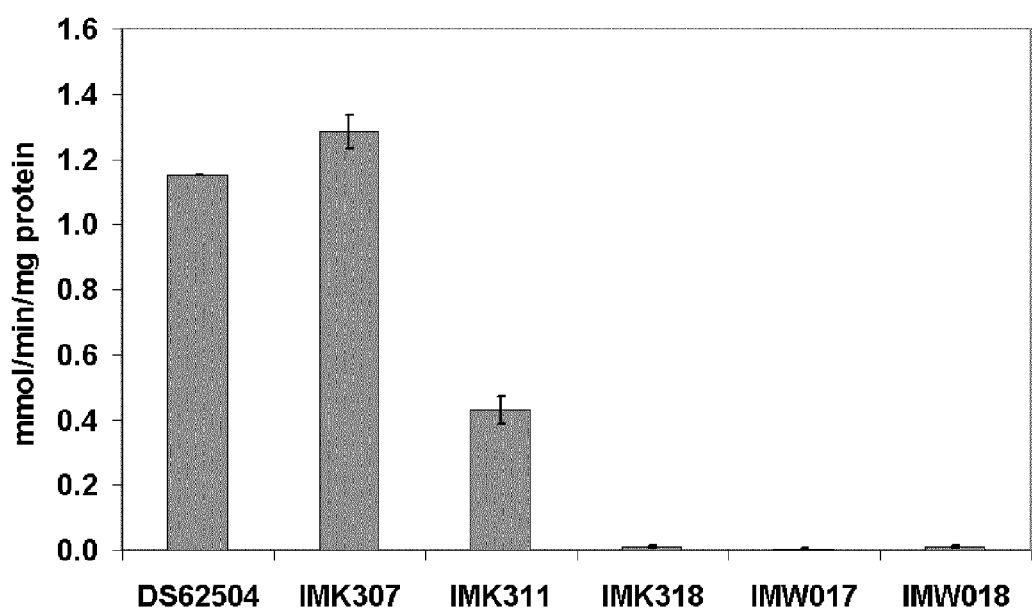

FIG. 10 shows the hexokinase enzyme activity of strains DS62504, IMK307, IMK311, IMK318, IMW017 and IMW018.

Figure 11:
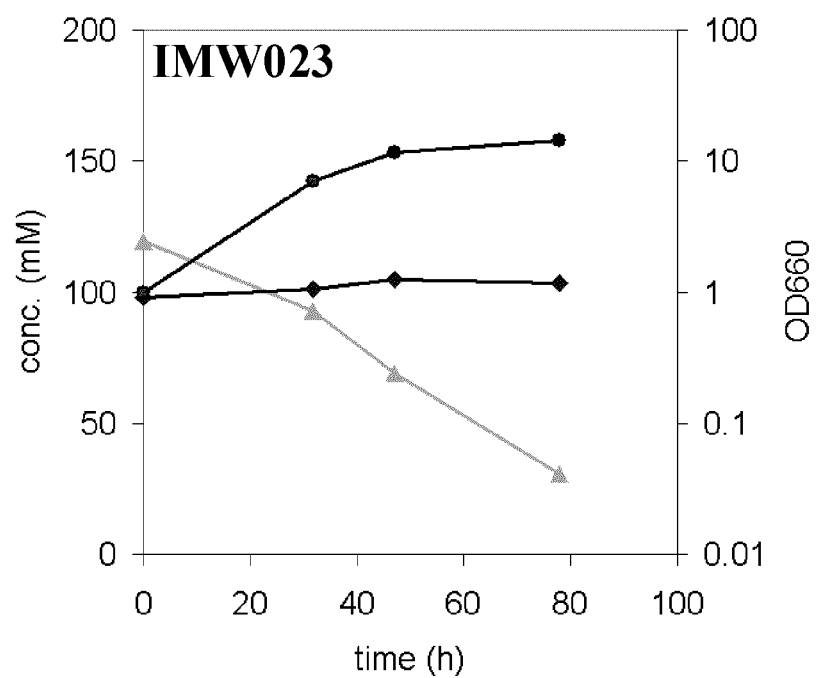

FIG. 11 shows the OD660 (●), arabinose concentration (▲), and glucose concentration (♦) during a shake flask cultivation of strain IMW023 in MY medium supplied with 2% of glucose and 2% of arabinose.

Figure 12:
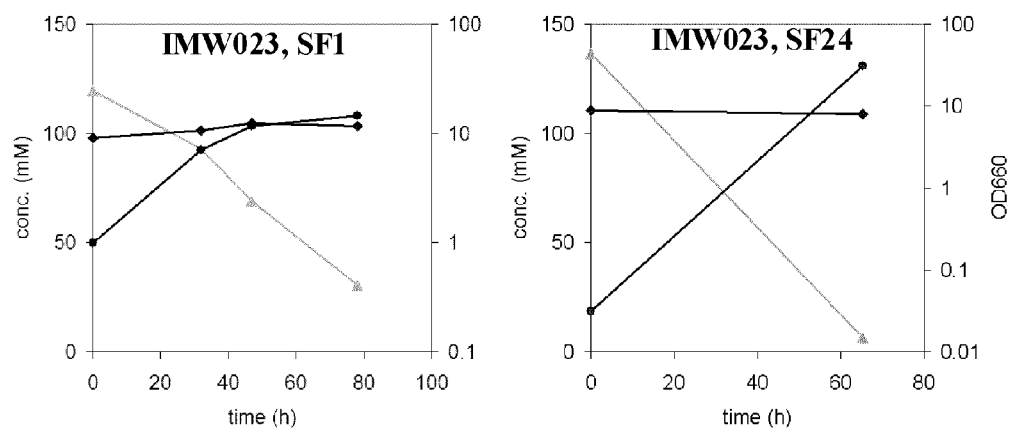

FIG. 12 shows the OD660 (●), arabinose concentration (▲), and glucose concentration (♦) during the first (SF1) and the 24$^{th}$ (SF24) shake flask cultivation of a serially transferred culture of strain IMW023 in MY medium supplied with 2% of glucose and 2% of arabinose.

Figure 13:
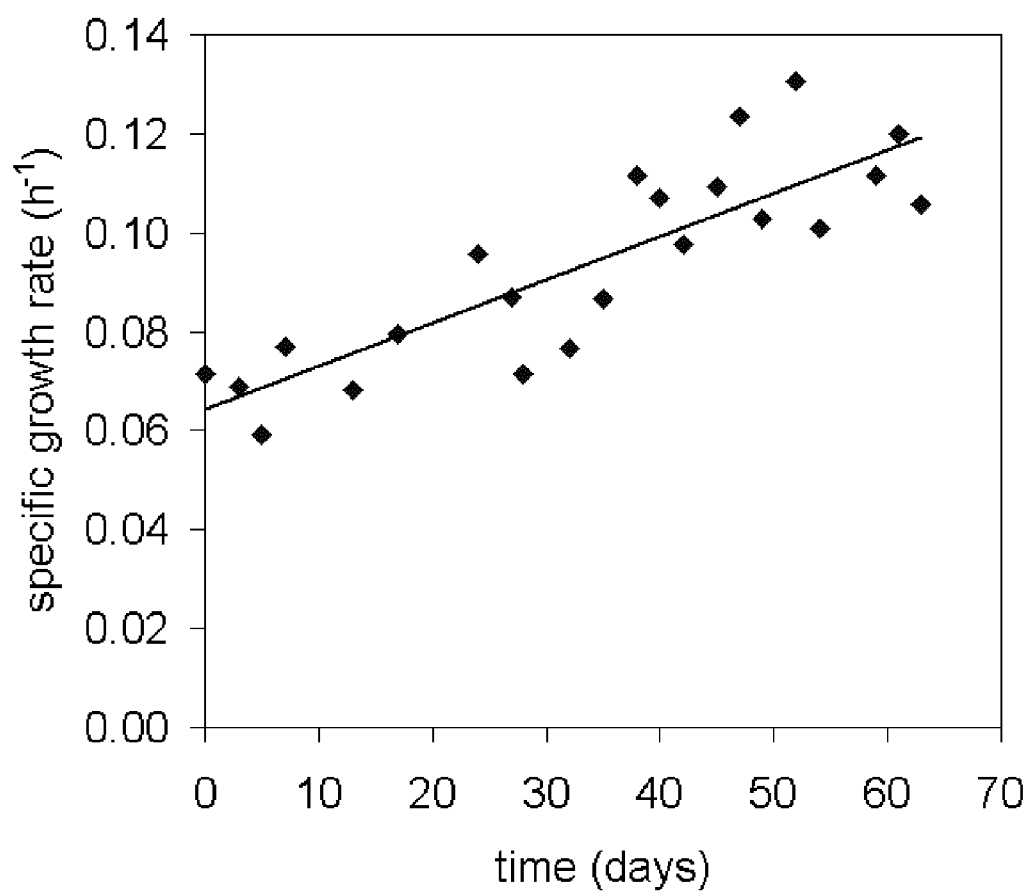

FIG. 13 shows the estimated specific growth rates determined in the individual shake flask cultivations of a serially transferred culture of strain IMW023 in MY medium supplied with 2% of glucose and 2% of arabinose.

Figure 14:
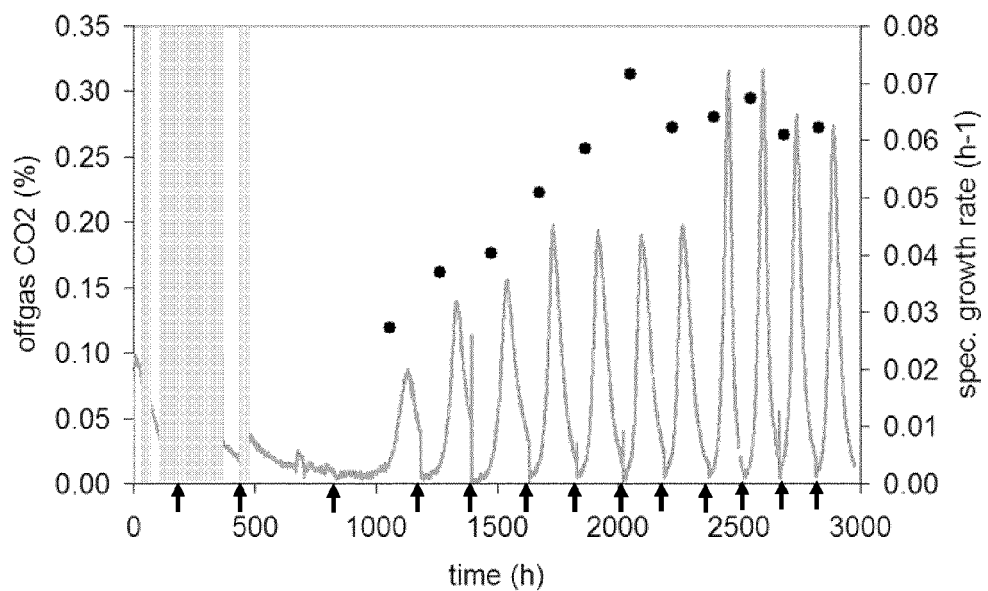

FIG. 14 shows the $CO_2$ percentage in the exhaust gas (solid gray line) and the specific growth rates during sequential anaerobic batch cultivations of strain IMW023 in MY medium supplied with 20 g/liter of glucose and 20 g/liter of arabinose, and the specific growth rates of the individual batch cultivations (●). The grey shades indicate where air was supplied in stead of nitrogen gas. The arrows indicate the start of a new consecutive batch.

Figure 15:
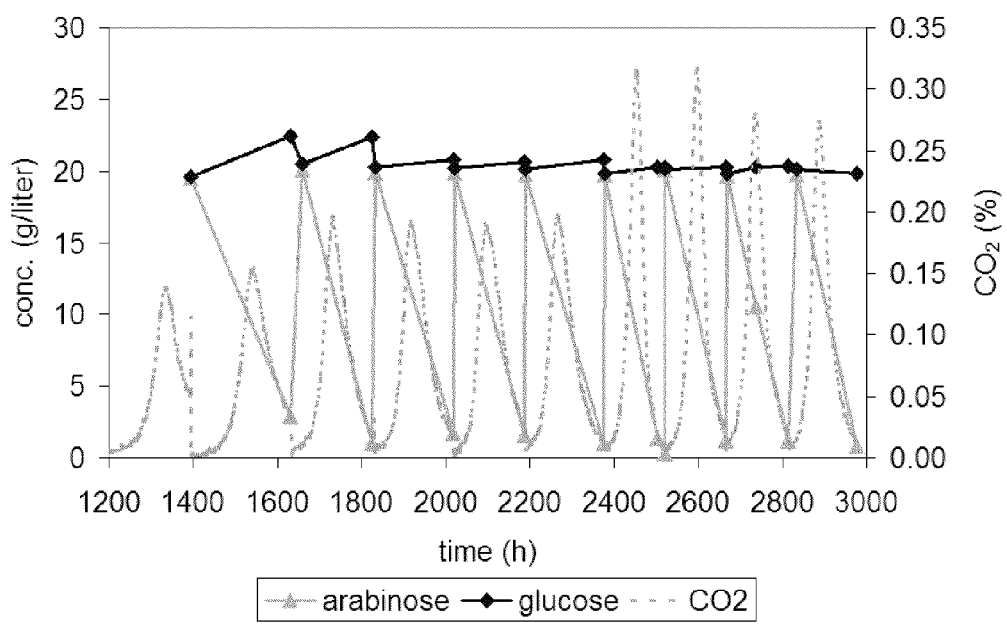

FIG. 15 shows the $CO_2$ percentage in the exhaust gas (solid gray line), the arabinose concentration (▲) and glucose concentration (▲) during sequential anaerobic batch cultivations of strain IMW023 in MY medium supplied with 20 g/liter of glucose and 20 g/liter of arabinose.

Figure 16:
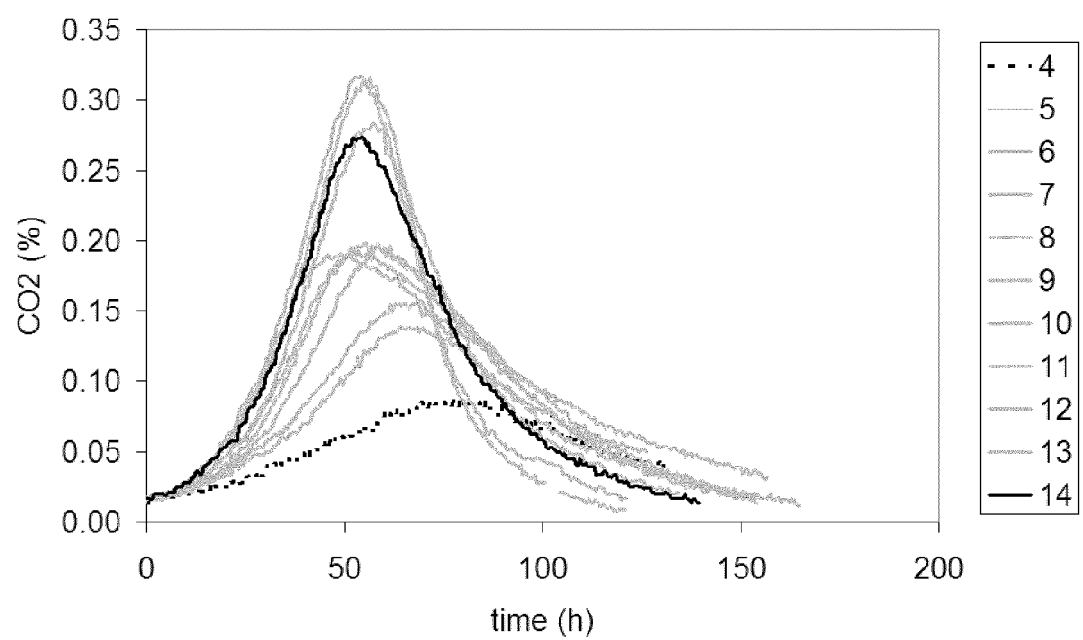

FIG. 16 shows the aligned $CO_2$ production profiles of the individual batches during anaerobic sequential batch cultivation of strain IMW023 in MY medium supplied with 20 g/liter of glucose and 20 g/liter of arabinose. The $CO_2$ production profiles are aligned assuming an equal initial $CO_2$ production level. The numbers in the legend indicate the consecutive batch numbers.

Figure 17:
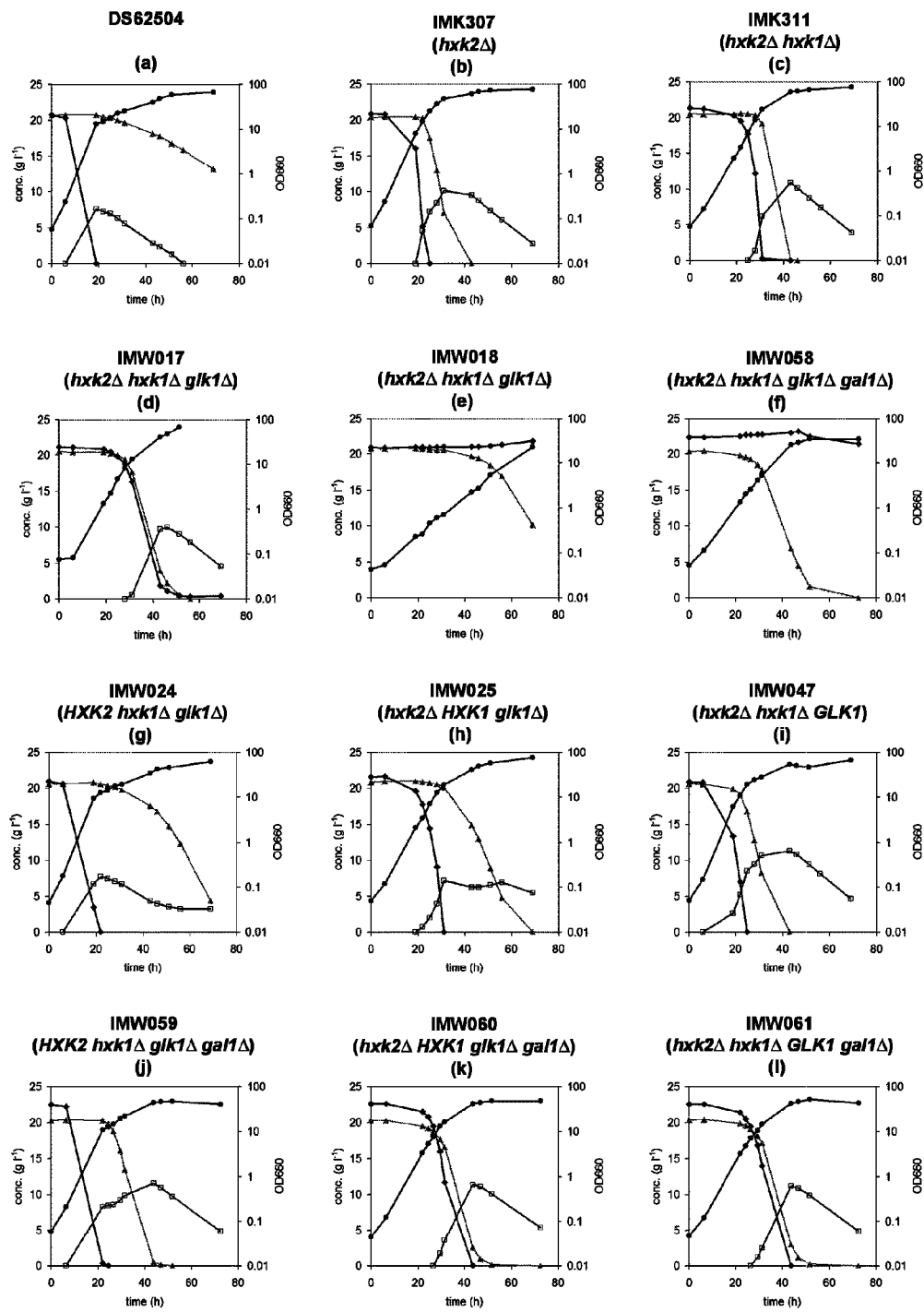

FIG. 17 shows glucose (♦), arabinose (▲) and ethanol (□) concentrations and optical density at 660 nm (OD660, ●) during shake flask cultivations of strains DS62504 (FIG. 17(a)), IMK307 (FIG. 17 (b), IMK311 (FIG. 17 (c)), IMW017 (FIG. 17 (d)), IMW018 (FIG. 17 (e)) and IMW058 (FIG. 17 (f)), IMW024 (FIG. 17 (g)), IMW025 (FIG. 17 (h)), IMW047 (FIG. 17 (i)), IMW059 (FIG. 17 (j)), IMW060 (FIG. 17 (k)), IMW061 (l)).

Figure 18:
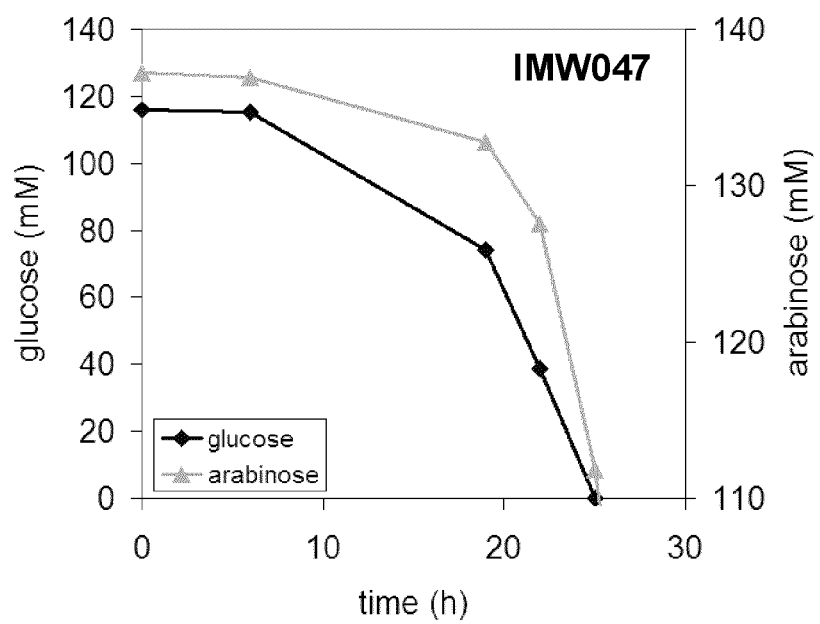

FIG. 18 shows glucose (♦) and arabinose (▲) concentrations during a shake flask cultivation of strain IMW047.

FIG. 19 shows the GAL1 amino acid alignment of strains CEN.PK 113-7D, IMK318, IMW017 and IMW018.

FIG. 20 shows the GAL2 amino acid alignment of strains CEN.PK 113-7D, IMK318, IMW017 and IMW018.

Figure 21:
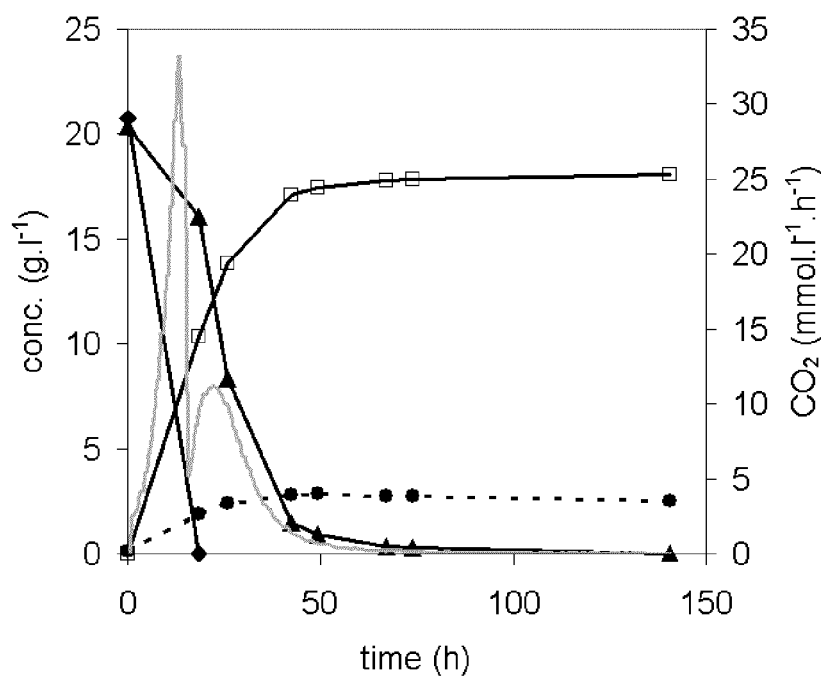

FIG. 21 shows glucose (♦), arabinose (▲), ethanol (□) concentrations, biomass dry weights (●) and CO2 production (solid grey line) during anaerobic cultivation of strain IMW059 in MY medium supplied with 20 g $l^{-1}$ glucose and 20 g $l^{-1}$ arabinose.

Figure 22:
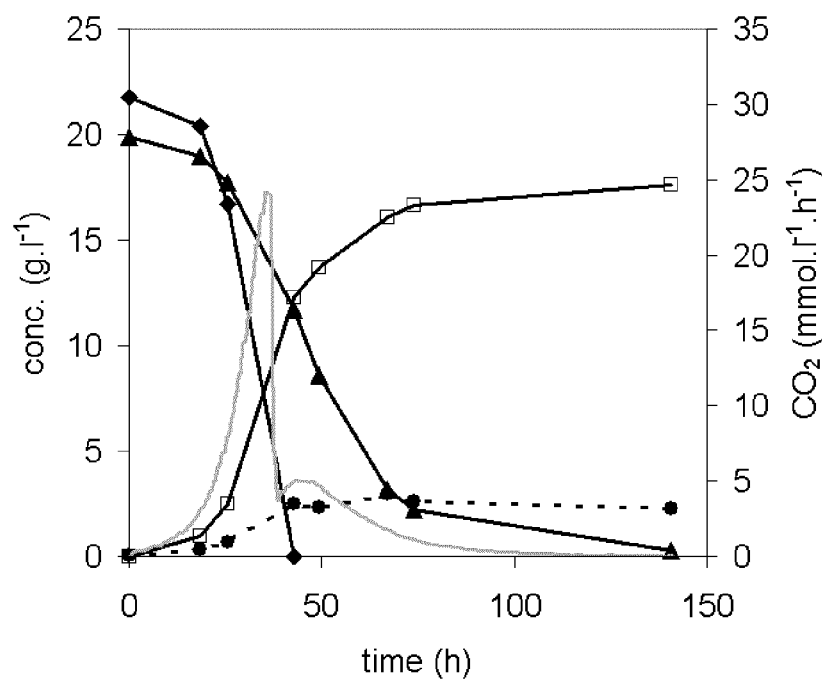

FIG. 22 shows glucose (♦), arabinose (▲), ethanol (□) concentrations, biomass dry weights (●) and CO2 production (solid grey line) during anaerobic cultivation of strain IMW060 in MY medium supplied with 20 g $l^{-1}$ glucose and 20 g $l^{-1}$ arabinose.

Figure 23:
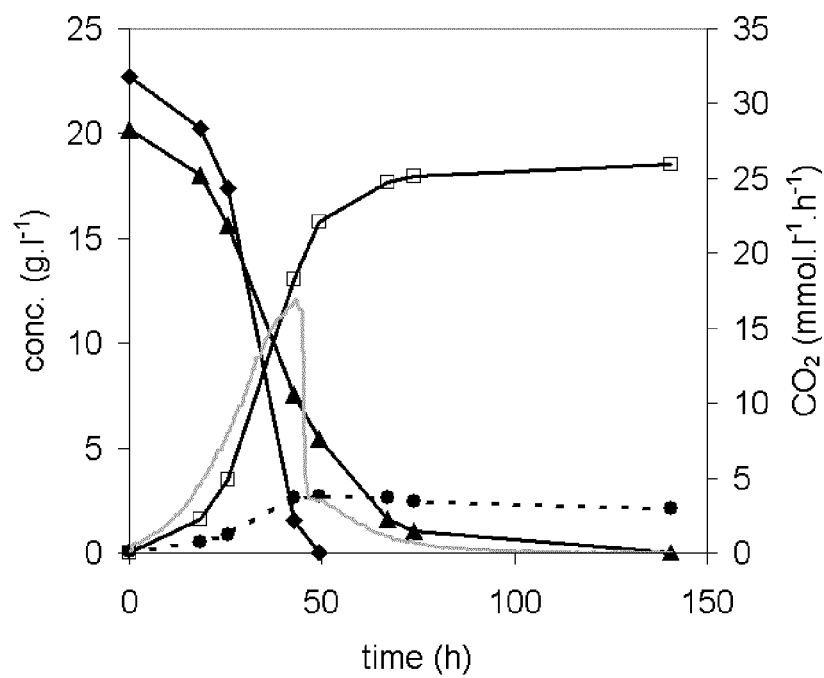

FIG. 23 shows glucose (♦), arabinose (▲), ethanol (□) concentrations, biomass dry weights (●) and CO2 production (solid grey line) during anaerobic cultivation of strain IMW061 in MY medium supplied with 20 g $l^{-1}$ glucose and 20 g $l^{-1}$ arabinose.

Figure 24:
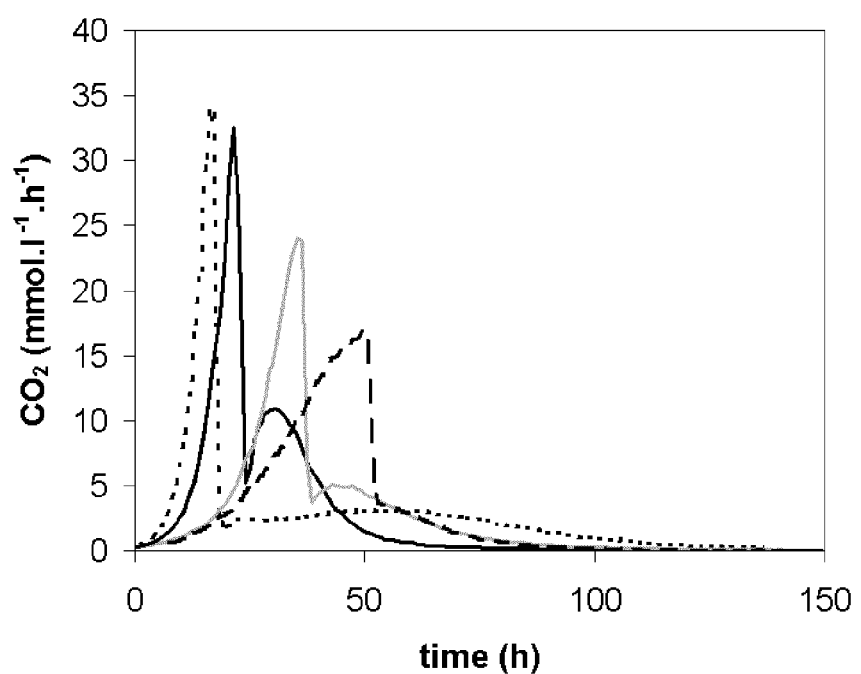

FIG. 24 shows the CO2 production profiles of strains DS62504 (dotted black line), IMW059 (solid black line), IMW060 (solid black line) and IMW061 (striped black line) during anaerobic cultivation in a mixture of 20 g $l^{-1}$ glucose and 20 g $l^{-1}$ arabinose.

Figure 25:
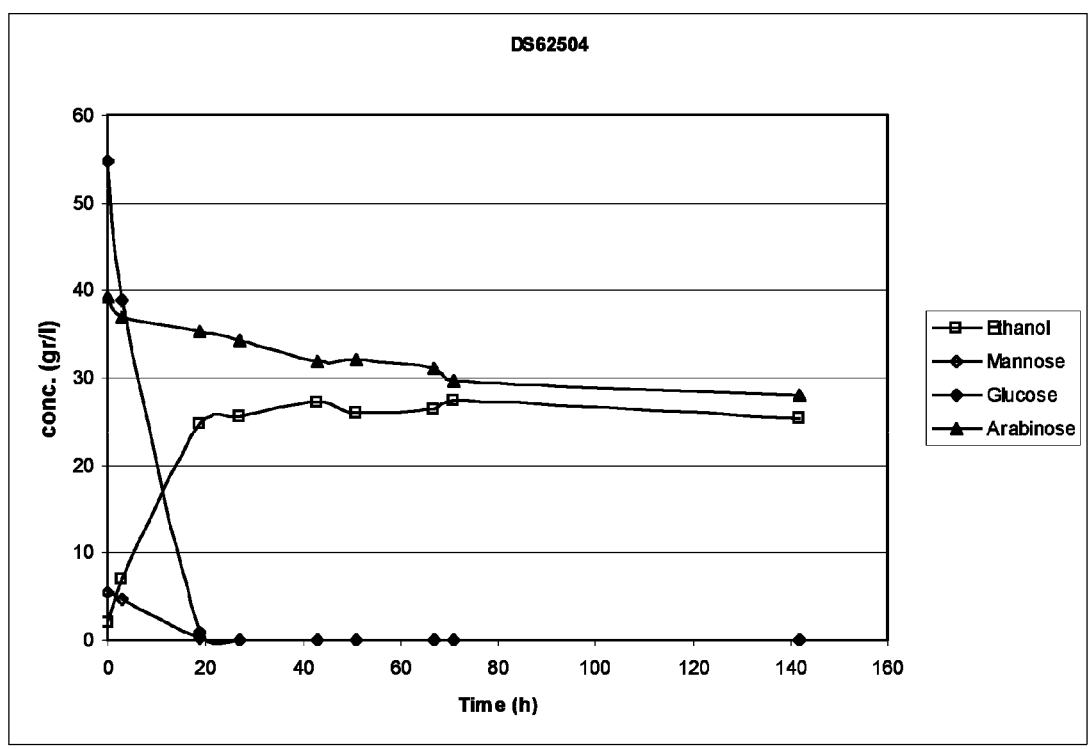

FIG. 25 shows glucose (♦), mannose (◇), arabinose (▲) and ethanol (□) concentrations during shake flask cultivations of strain DS62504 on medium CFMM2M.

Figure 26:
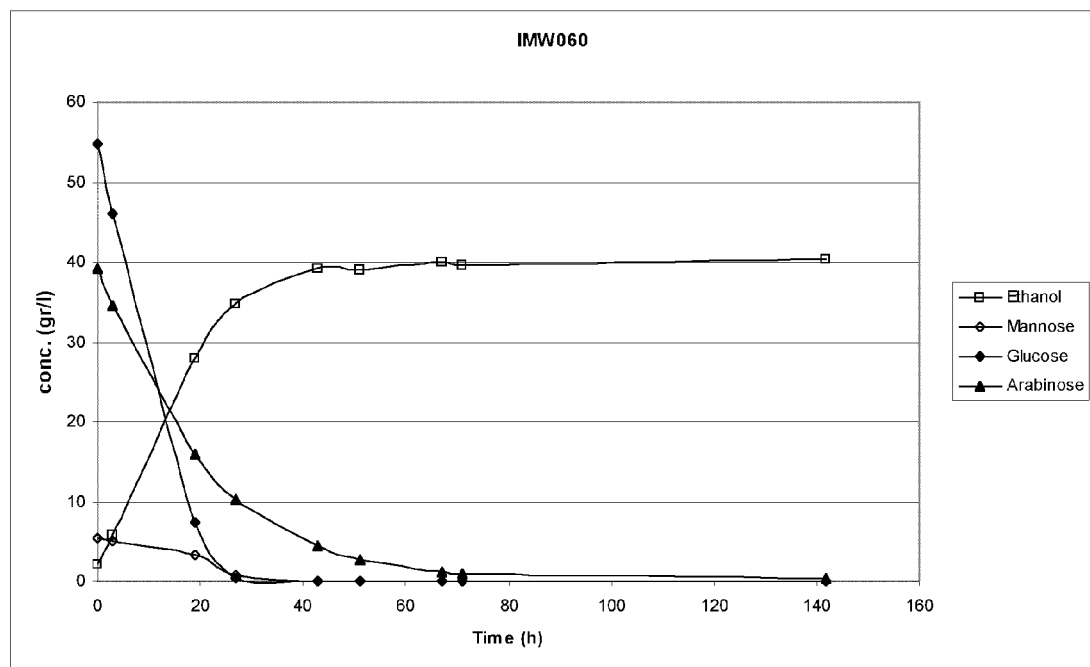

FIG. 26 shows glucose (♦), mannose (◇), arabinose (▲) and ethanol (□) concentrations during shake flask cultivations of strain IMW060 on medium CFMM2M.

Figure 27:
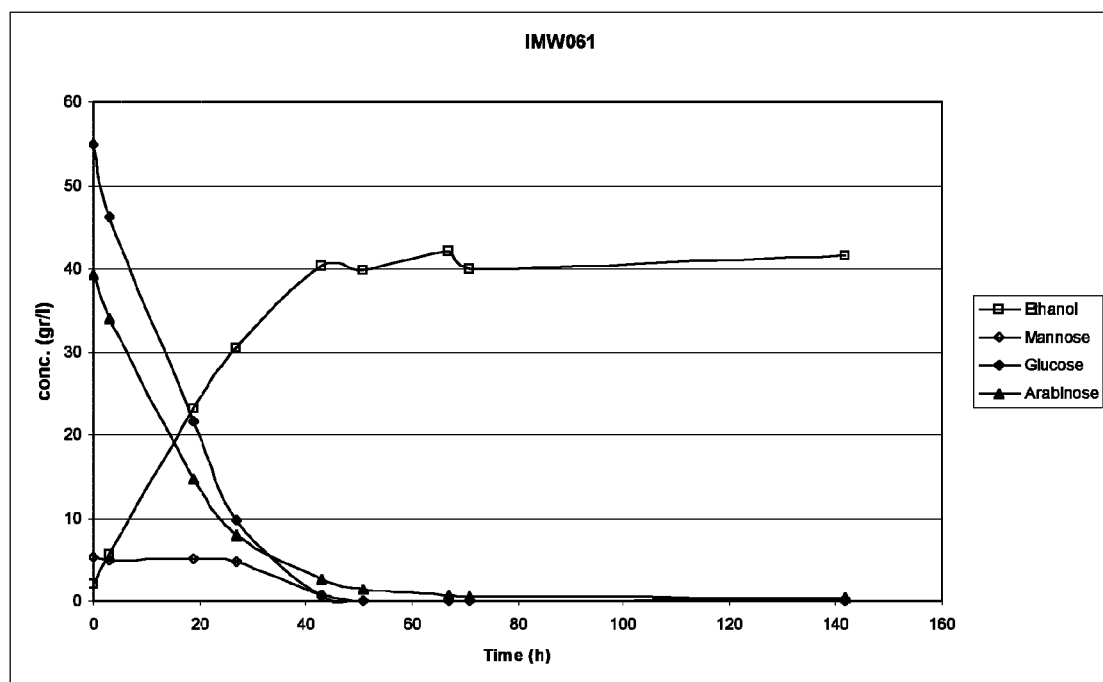

FIG. 27 shows glucose (♦), mannose (◇), arabinose (▲) and ethanol (□) concentrations during shake flask cultivations of strain IMW061 on medium CFMM2M.

Figure 28:
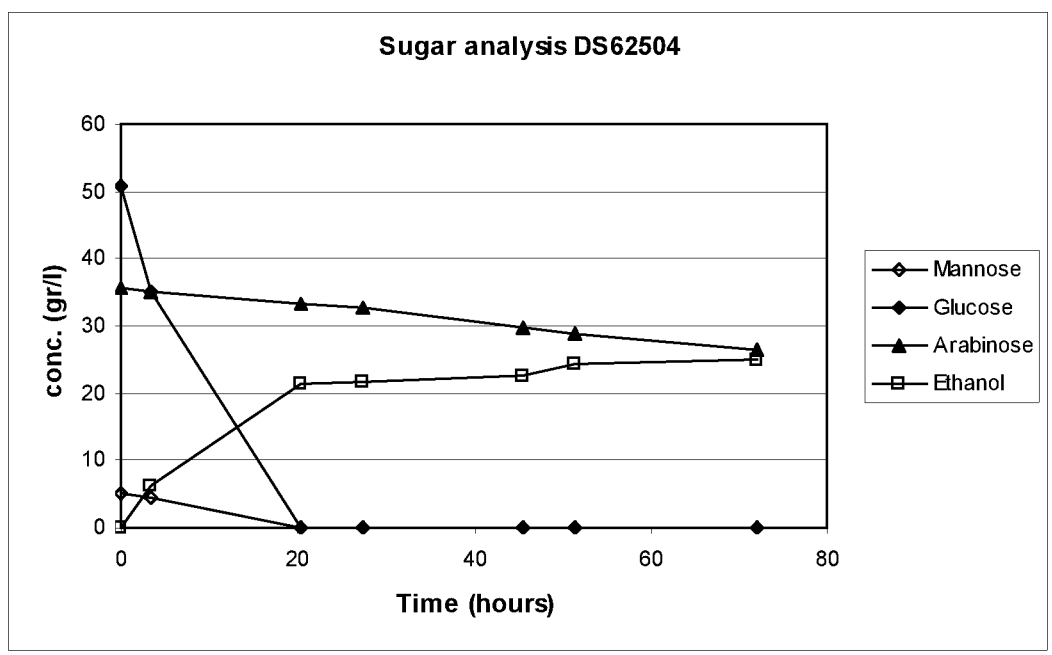

FIG. 28 shows glucose (♦), mannose (◇), arabinose (▲) and ethanol (□) concentrations during shake flask cultivations of strain DS62504 on medium CFMM1M.

Figure 29:
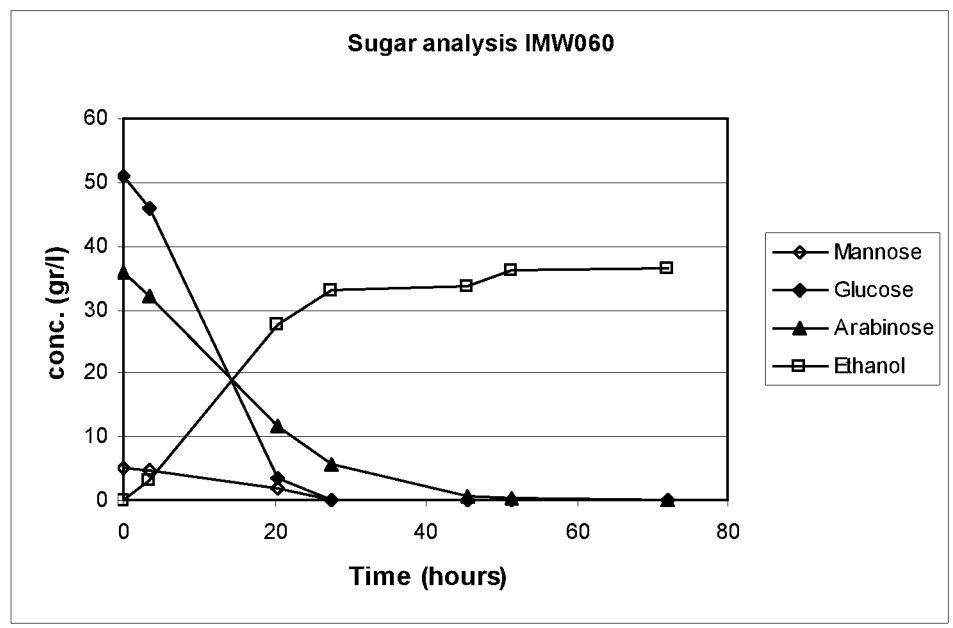

FIG. 29 shows glucose (♦), mannose (◇), arabinose (▲) and ethanol (□) concentrations during shake flask cultivations of strain IMW060 on medium CFMM1M.

Figure 30:
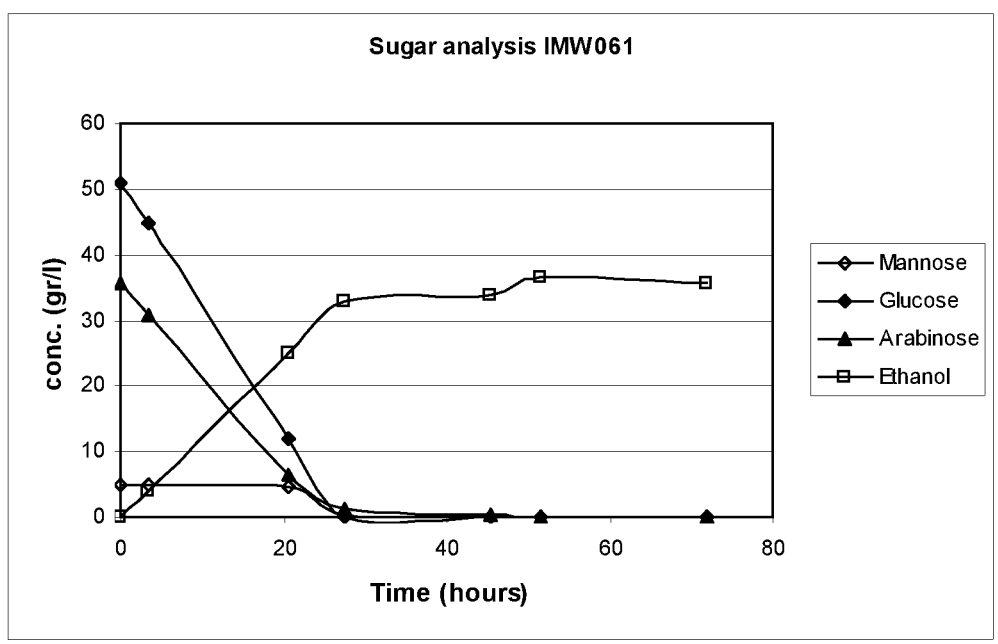

FIG. 30 shows glucose (♦), mannose (◇), arabinose (▲) and ethanol (□) concentrations during shake flask cultivations of strain IMW061 on medium CFMM1M.

BRIEF DESCRIPTION OF THE SEQUENCE LISTING

Oligonucleotides used for construction of gene disruption cassettes:
SEQ ID NO: 1 sets out the sequence of oligonucleotide HXK2-disA
SEQ ID NO: 2 sets out the sequence of oligonucleotide HXK2-disB
SEQ ID NO: 3 sets out the sequence of oligonucleotide HXK1-disA
SEQ ID NO: 4 sets out the sequence of oligonucleotide HXK1-disB
SEQ ID NO: 5 sets out the sequence of oligonucleotide GLK1-disA
SEQ ID NO: 6 sets out the sequence of oligonucleotide GLK1-disB
Oligonucleotides Used for Diagnostic Purposes:
SEQ ID NO: 7 sets out the sequence of oligonucleotide KanA
SEQ ID NO: 8 sets out the sequence of oligonucleotide KanB
SEQ ID NO: 9 sets out the sequence of oligonucleotide HXK2-FW
SEQ ID NO: 10 sets out the sequence of oligonucleotide HXK2-RV
SEQ ID NO: 11 sets out the sequence of oligonucleotide HXK1-FW
SEQ ID NO: 12 sets out the sequence of oligonucleotide HXK1-RV
SEQ ID NO: 13 sets out the sequence of oligonucleotide GLK1-FW
SEQ ID NO: 14 sets out the sequence of oligonucleotide GLK1-RV
SEQ ID NO: 15 sets out the DNA sequence of HXK1
SEQ ID NO: 16 sets out the DNA sequence of HXK2
SEQ ID NO: 17 sets out the DNA sequence of GLK1
SEQ ID NO: 18 sets out the DNA sequence of GAL1
SEQ ID NO: 19 sets out the DNA sequence of YDR516C
SEQ ID NO: 20 sets out the DNA sequence of YLR446W
SEQ ID NO: 21 sets out the AMINO ACID sequence of HXK1
SEQ ID NO: 22 sets out the AMINO ACID sequence of HXK2
SEQ ID NO: 23 sets out the AMINO ACID sequence of GLK1
SEQ ID NO: 24 sets out the AMINO ACID sequence of GAL1
SEQ ID NO: 25 sets out the AMINO ACID sequence of YDR516C
SEQ ID NO: 26 sets out the AMINO ACID sequence of YLR446W
SEQ ID NO: 27 sets out the sequence of oligonucleotide GAL1-DisA
SEQ ID NO: 28 sets out the sequence of oligonucleotide GAL1-DisB
SEQ ID NO: 29 sets out the sequence of oligonucleotide GAL1-FW2
SEQ ID NO: 30 sets out the sequence of oligonucleotide GAL1-RV2
SEQ ID NO: 31 sets out the sequence of oligonucleotide HXK2-FW2
SEQ ID NO: 32 sets out the sequence of oligonucleotide HXK2-RV2
SEQ ID NO: 33 sets out the sequence of oligonucleotide HXK2-FW3
SEQ ID NO: 34 sets out the sequence of oligonucleotide HXK2-RV3
SEQ ID NO: 35 sets out the sequence of oligonucleotide HXK1-FW2
SEQ ID NO: 36 sets out the sequence of oligonucleotide HXK1-RV2
SEQ ID NO: 37 sets out the sequence of oligonucleotide HXK1-FW3
SEQ ID NO: 38 sets out the sequence of oligonucleotide HXK1-RV3
SEQ ID NO: 39 sets out the sequence of oligonucleotide GLK1-FW4
SEQ ID NO: 40 sets out the sequence of oligonucleotide GLK1-RV4
SEQ ID NO: 41 sets out the sequence of oligonucleotide GLK1-FW5
SEQ ID NO: 42 sets out the sequence of oligonucleotide GLK1-RV5
SEQ ID NO: 43 sets out the DNA sequence of GAL1 (CEN.PK 113-7D)
SEQ ID NO: 44 sets out the DNA sequence of GAL1 (IMK318)
SEQ ID NO: 45 sets out the DNA sequence of GAL1 (IMW017)
SEQ ID NO: 46 sets out the DNA sequence of GAL1 (IMW018)
SEQ ID NO: 47 sets out the DNA sequence of GAL2 (CEN.PK 113-7D)
SEQ ID NO: 48 sets out the DNA sequence of GAL2 (IMK318)
SEQ ID NO: 49 sets out the DNA sequence of GAL2 (IMW017)
SEQ ID NO: 50 sets out the DNA sequence of GAL2 (IMW018)
SEQ ID NO: 51 sets out the AMINO ACID sequence of GAL1 (CEN.PK 113-7D)
SEQ ID NO: 52 sets out the AMINO ACID sequence of GAL1 (IMK318)
SEQ ID NO: 53 sets out the AMINO ACID sequence of GAL1 (IMW017)
SEQ ID NO: 54 sets out the AMINO ACID sequence of GAL1 (IMW018)
SEQ ID NO: 55 sets out the AMINO ACID sequence of GAL2 (CEN.PK 113-7D)
SEQ ID NO: 56 sets out the AMINO ACID sequence of GAL2 (IMK318)
SEQ ID NO: 57 sets out the AMINO ACID sequence of GAL2 (IMW017)
SEQ ID NO: 58 sets out the AMINO ACID sequence of GAL2 (IMW018)

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element. By way of example, cell can herein be one cell, but refer also to a population of cells or a strain.

The various embodiments of the invention described herein may be cross-combined.

Disruption is herein understood to mean any disruption of activity, and includes, but is not limited to deletion, mutation, reduction of the affinity of the disrupted gene and expression of antisense RNA complementary to hexokinase mRNA. A gene disruptant is a cell that has one or more disruption of the respective gene. Native in yeast herein is understood as that the gene is present in the yeast cell before the disruption. It includes the situation that the gene native in yeast is present in a wild-type yeast cell, a laboratory yeast cell or an industrial yeast cell. Yeast cell may herein also be designated as yeast strain or as part of yeast strain.

In an embodiment, the pentose and glucose fermenting yeast cell that produces ethanol at a higher overall rate than the corresponding wild-type strain and has shorter fermentation time and/or co-consumes pentose and glucose, preferably co-consumes these anaerobically pentose and simultaneously, as opposed to sequentially.

In an embodiment the yeast comprises an exogenous hexokinase. Preferably the exogenous hexokinase introduces into the cell a hexokinase activity.

Exogenous is herein understood as not present in the yeast cell before the introduction of the hexokinase. An exogenous hexokinase may include, but is not limited to, a gene that is native in yeast or a gene that has the same sequence as the disrupted hexokinase.

In an embodiment of the invention, the yeast cell is a strain wherein reduced expression of hexokinase in the yeast variant is effected by a means selected from the group consisting of disruption of the hexokinase gene and expression of antisense RNA complementary to hexokinase mRNA.

In an embodiment of the invention the yeast cell is a hexokinase disruptant of *Saccharomyces cerevisiae.*

In another embodiment the yeast cell is *Saccharomyces cerevisiae* IMW017, IMW018, IMK306, IMK307 and/or IMK318.

In an embodiment the yeast cell has a overall ethanol production rate that is at least about 20% higher, at least about 50% or at least about 100% higher than that of the corresponding wild-type yeast.

The invention further relates to a process for producing ethanol from the fermentation of pentose, comprising the step of: culturing a yeast cell according to the invention in a pentose-containing sugar composition under suitable fermentation conditions for a period of time sufficient to allow the fermentation of pentose to ethanol, wherein the yeast cell ferments pentose to produce ethanol at a high level relative to the corresponding wild-type yeast and wherein the yeast cell has reduced expression of functional hexokinase, relative to the corresponding wild-type yeast.

In an embodiment of the process, the fermentation time is reduced relative to the corresponding fermentation of wild-type yeast, preferably the fermentation time is reduced 40% or more.

In an embodiment of the process, pentose and glucose are co-fermented. In another embodiment of the process, the overall ethanol production rate is at least about 20%, at least about 50% or about 100% higher than that of a process with the corresponding wild-type yeast.

In an embodiment of the process, the yeast cell is *Saccharomyces cerevisiae* IMW017, IMW018, IMK306, IMK307 and/or IMK318.

In an embodiment of the process the pentose-containing material comprises a hydrolysate of lignocellulosic material.

In an embodiment of the process, the hydrolysate is an enzymatic hydrolysate of lignocellulosic material.

The invention further relates to the use of a disruption of one or more hexokinases in yeast in a process of evolutionary engineering and/or process of strain improvement of the yeast. These are known processes. Evolutionary engineering is a process wherein industrially relevant phenotypes of a microorganism, herein the yeast, can be coupled to the specific growth rate and/or the affinity for a nutrient, by a process of rationally set-up natural selection. Evolutionary Engineering is for instance described in detail in Kuijper, M, et al, FEMS Yeast Research 5 (2005) 925-934, WO2008041840 and WO2009112472. After the evolutionary engineering the resulting pentose fermenting yeast cell is isolated. The isolation may be executed in any known manner, e.g. by separation of cells from a yeast cell broth used in the evolutionary engineering, for instance by taking a cell sample or by filtration or centrifugation.

The present invention is a yeast cell that ferments pentose in sugar mixtures that also contain glucose at a higher rate than the corresponding wild-type yeast, the yeast cell characterized by reduced expression of one or more native hexokinase gene.

Without limitations to the scope of the invention and without wishing to be bound to theory, this phenomenon is most likely a consequence of competitive inhibition of pentose transport by glucose or due to glucose repression of genes crucial for pentose fermentation or due to inactivation or degradation of proteins involved or reduction of affinity in the presence of glucose. In the presence of glucose, evolutionary engineering for growth on pentoses of strains that no longer (can) utilise glucose should result in a glucose insensitive phenotype. Such a strain, that can no longer consume glucose, can for instance be obtained by deletion of all three hexo/gluco-kinases (hxk1Δ hxk2Δ glk1Δ). Herein it is shown that also deletion of gal1 (gal1Δ) is advantageous to further decrease glucose consumption in the triple disruptant, thus creating a quadruple disruptant.

The present invention is also a method of producing ethanol from the fermentation of pentose, comprising the step of: culturing a yeast cell in a pentose-containing material under suitable fermentation conditions for a period of time sufficient to allow the fermentation of pentose to ethanol, the yeast variant being capable of fermenting pentose at a high rate relative to the corresponding wild-type yeast and having reduced expression of functional hexokinase.

The yeast cell of the present invention is a hexokinase disruptant. By a hexokinase disruptant, it is meant a variant in which a part or all of the native gene is removed or replaced with DNA of which the expression does not result in a expression product having any function of the native hexokinase.

In an alternative embodiment of disruptant, expression of hexokinase may be down-regulated through the use of an antisense construct in which part or all of the antisense strand coding for hexokinase is expressed under the regulation of a promotor that responds to diminished oxygen. In this embodiment, the antisense mRNA for hexokinase is expressed under oxygen limiting conditions and thereby inactivates the functional hexokinase.

In another alternative embodiment of disruptant, the promotor region for the functional hexokinase is replaced by a promoter that responds to diminished oxygen by down-regulating expression of the hexokinase gene.

By "wild-type" yeast, it is meant a pentose-fermenting yeast strain with normal levels of functional hexokinase from which the yeast cell of the present invention is derived. In certain cases, the "wild-type yeast" as defined in this patent application, may include mutagenized yeast. For example, the *Saccharomyces cerevisiae* strain DS62504, from which IMW017, IMW018, IMK306, IMK307 and IMK318 were developed, is itself a mutated yeast strain. However, DS62504 is also a wild-type yeast, as defined herein, because it is a pentose-fermenting yeast with normal levels of functional hexokinase that was used to develop a yeast cell of the present invention.

Hexokinase (hxk) is herein any enzyme that phosphorylates a six-carbon sugar, a hexose, to a hexose phosphate. In most tissues and organisms, glucose is the most important substrate of hexokinases, and glucose-6-phosphate the most important product.

Hexokinases have been found in most organisms checked, ranging from bacteria, yeast, and plants to humans and other vertebrates. They are categorized as actin fold proteins, sharing a common ATP binding site core surrounded by more variable sequences that determine substrate affinities and other properties. Several hexokinase isoforms or isozymes providing different functions can occur in a single species.

Reaction of Hexokinase:
The intracellular reactions mediated by hexokinases can be typified as:

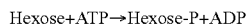

Hexose+ATP→Hexose-P+ADP

The Yeast Cell

According to the invention disruption of native hexokinase activity leads to shorter fermentation time in C5/C6 fermentation and/or to co-consumption by the yeast cell of pentose and glucose.

Resultant yeast cells, designated IMW017, IMW018, IMK306, IMK307 and/or IMK318, were obtained and has been characterized as described in detail below. It is anticipated that a yeast cell of *S. cerevisiae* characterized by reduced expression of functional hexokinase gene and increased overall ethanol yield may be obtained by means other than eliminating the hexokinase gene by one step site-specific integration using a disruption cassette. For example, a variant lacking functional hexokinase, or which expresses hexokinase at a reduced level, could be obtained by any of several means known to the art, such as exposing yeast cells to DNA-intercalating agents or irradiating yeast cells with ultra violet light. It is likely that hexokinase deficient cells could be distinguished from wild type cells on the basis of colony size and other morphological patterns (i.e., petite size, yellow colonies with a wrinkled appearance). The hexokinase status of putative hexokinase deficient colonies presumptively identified on the basis of this unique phenotype could be confirmed by for instance the inability to grow on medium containing glucose as the sole carbon source or by hexokinase activity determinations.

The yeast cell typically contains genes of a pentose metabolic pathway non-native to the yeast and/or that allow the yeast cell to convert pentose(s). In one embodiment, the yeast cell may comprise one or two or more copies of one or more xylose isomerases and/or one or two or more copies of one or more xylose reductase and xylitol dehydrogenase genes, allowing the yeast cell to convert xylose. In an embodiment thereof, these genes may be integrated into the yeast cell genome. In another embodiment, the yeast cell comprises the genes araA, araB and araD. It is then able to ferment arabinose. In one embodiment of the invention the yeast cell comprises xylA-gene, XYL1 gene and XYL2 gene and/or XKS1-gene, to allow the yeast cell to ferment xylose; deletion of the aldose reductase (GRE3) gene; overexpression of PPP-genes TAL1, TKL1, RPE1 and RKI1 to allow the increase of the flux through the pentose phosphate pass-way in the cell, and/or overexpression of GAL2, and/or deletion of GAL80. Thus though inclusion of the above genes, suitable pentose or other metabolic pathway(s) may be introduced in the yeast cell that were non-native in the (wild type) yeast cell.

In an embodiment, the yeast cell is derived from an industrial yeast, by disruption of hexokinase. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial yeast cell is constructed on the basis of an industrial host cell, wherein the construction is conducted as described hereinafter. Examples of industrial yeast (*S. cerevisiae*) are Ethanol Red® (Fermentis) Fermiol® (DSM) and Thermosacc® (Lallemand).

In an embodiment the yeast cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxymethylfurfural. Examples or phenolic compounds are vanillin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

The yeast cells according to the invention are preferably inhibitor tolerant, i.e. they can withstand common inhibitors at the level that they typically have with common pretreatment and hydrolysis conditions, so that the yeast cells can find broad application, i.e. it has high applicability for different feedstock, different pretreatment methods and different hydrolysis conditions.

In one embodiment, the industrial yeast cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

In an embodiment, the yeast cell is marker-free. As used herein, the term "marker" refers to a gene encoding a trait or a phenotype which permits the selection of, or the screening for, a host cell containing the marker. Marker-free means that markers are essentially absent in the yeast cell. Being marker-free is particularly advantageous when antibiotic markers have been used in construction of the yeast cell and are removed thereafter. Removal of markers may be done using any suitable prior art technique, e.g intramolecular recombination. A suitable method of marker removal is illustrated in the examples.

The yeast cell further may comprise those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the yeast cell a cell that is naturally capable of alcoholic fermentation, preferably, anaerobic alcoholic fermentation. A yeast cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a yeast cell may be naturally present in the cell or may be introduced or modified by genetic modification.

Construction of the Yeast Cell

According to an embodiment, the genes may be introduced in the yeast cell by introduction into a host cell:
a) a cluster consisting of PPP-genes TAL1, TKL1, RPE1 and RKI1, optionally under control of strong constitutive promoter;
b) a cluster consisting of a xylA-gene under under control of strong constitutive promoter;
c) a cluster comprising a XKS1-gene under control of strong constitutive promoter,
d) a cluster consisting of the genes araA, araB and araD under control of a strong constitutive promoter
e) deletion of an aldose reductase gene
f) disruption of one or more hexokinase genes native in yeast;
g) evolutionary engineering of the strain resulting from a) to e); and optionally
h) introduction of one or more exogenous hexokinase gene into the cell resulting from the evolutionary engineering to produce the yeast cell.

The above cell may be constructed using known recombinant expression techniques.

Recombinant Expression

The yeast cell is a recombinant cell. That is to say, a yeast cell comprises, or is transformed with or is genetically modified with a nucleotide sequence that does not naturally occur in the cell in question.

Techniques for the recombinant expression of enzymes in a cell, as well as for the additional genetic modifications of a yeast cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Sequence Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

The terms "homology", "percent homology", "percent identity" or "percent similarity" are used interchangeably herein. For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of squence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using the program NEEDLE.

The protein sequences used in the present invention can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences and BLASTN for nucleotide sequences. The BLAST program uses as defaults:

Cost to open gap: default=5 for nucleotides/11 for proteins
Cost to extend gap: default=2 for nucleotides/1 for proteins
Penalty for nucleotide mismatch: default=−3
Reward for nucleotide match: default=1
Expect value: default=10
Wordsize: default=11 for nucleotides/28 for megablast/3 for proteins Furthermore the degree of local identity (homology) between the amino acid sequence query or nucleic acid sequence query and the retrieved homologous sequences is determined by the BLAST program. However only those sequence segments are compared that give a match above a certain thresshold. Accordingly the program calculates the identity only for these matching segments. Therefore the identity calculated in this way is referred to as local identity.

Bioproducts Production

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus* or *K. fragilis*.

A yeast cell may be a cell suitable for the production of ethanol. A yeast cell may, however, be suitable for the production of fermentation products other than ethanol Such non-ethanolic fermentation products include in principle any bulk or fine chemical that is producible by a eukaryotic microorganism such as a yeast or a filamentous fungus.

A preferred yeast cell for production of non-ethanolic fermentation products is a host cell that contains a genetic modification that results in decreased alcohol dehydrogenase activity Lignocellulose Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher tempatures, at a reaction time to release sufficient amounts of sugar(s). The result of the enzymatic hydrolysis is hydrolyisis product comprising C5/C6 sugars, herein designated as the sugar composition.

The Sugar Composition

The sugar composition used according to the invention comprises glucose and one or more pentose, e.g. arabinose and/or xylose. Any sugar composition may be used in the invention that suffices those criteria. Optional sugars in the sugar composition are galactose and mannose. In a preferred embodiment, the sugar composition is a hydrolysate of one or more lignocellulosic material. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 1. The listed lignocelluloses include: corn cobs, corn fiber, rice hulls, melon shells, sugar beet pulp, wheat straw, sugar cane bagasse, wood, grass and olive pressings.

TABLE 1

Overview of sugar compositions from lignocellulosic materials.

| Lignocellulosic material | Gal | Xyl | Ara | Man | Glu | Rham | Sum | %. Gal. | Lit. |
|---|---|---|---|---|---|---|---|---|---|
| Corn cob a | 10 | 286 | 36 | | 227 | 11 | 570 | 1.7 | (1) |
| Corn cob b | 131 | 228 | 160 | | 144 | | 663 | 19.8 | (1) |
| Rice hulls a | 9 | 122 | 24 | 18 | 234 | 10 | 417 | 2.2 | (1) |
| Rice hulls b | 8 | 120 | 28 | | 209 | 12 | 378 | 2.2 | (1) |
| Melon Shells | 6 | 120 | 11 | | 208 | 16 | 361 | 1.7 | (1) |
| Sugar beet pulp | 51 | 17 | 209 | 11 | 211 | 24 | 523 | 9.8 | (2) |
| Whea straw Idaho | 15 | 249 | 36 | | 396 | | 696 | 2.2 | (3) |
| Corn fiber | 36 | 176 | 113 | | 372 | | 697 | 5.2 | (4) |
| Cane Bagasse | 14 | 180 | 24 | 5 | 391 | | 614 | 2.3 | (5) |
| Corn stover | 19 | 209 | 29 | | 370 | | 626 | | (6) |
| Athel (wood) | 5 | 118 | 7 | 3 | 493 | | 625 | 0.7 | (7) |
| *Eucalyptus* (wood) | 22 | 105 | 8 | 3 | 445 | | 583 | 3.8 | (7) |
| CWR (grass) | 8 | 165 | 33 | | 340 | | 546 | 1.4 | (7) |
| JTW (grass) | 7 | 169 | 28 | | 311 | | 515 | 1.3 | (7) |
| MSW | 4 | 24 | 5 | 20 | 440 | | 493 | 0.9 | (7) |
| Reed Canary Grass Veg | 16 | 117 | 30 | 6 | 209 | 1 | 379 | 4.2 | (8) |
| Reed Canary Grass Seed | 13 | 163 | 28 | 6 | 265 | 1 | 476 | 2.7 | (9) |
| Olive pressing residu | 15 | 111 | 24 | 8 | 329 | | 487 | 3.1 | (9) |

Gal = galactose,
Xyl = xylose,
Ara = arabinose,
Man = mannose,
Glu = glutamate,
Rham = rhamnose.
The percentage galactose (% Gal) and literature source is given.

It is clear from table 1 that in these lignocelluloses a high amount of sugar is presence in de form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the yeast cell.

It is expected that yeast cells of the present invention can be further manipulated to achieve other desirable characteristics, or even higher overall ethanol yields.

Selection of improved yeast cells by passaging the yeast cells on medium containing hydrolysate has resulted in improved yeast with enhanced fermentation rates. Using the teachings of the present invention, one could readily such improved strains.

By pentose-containing material, it is meant any medium comprising pentose, whether liquid or solid. Suitable pentose-containing materials include hydrolysates of polysaccharide or lignocellulosic biomass such as corn hulls, wood, paper, agricultural biproducts, and the like.

By a "hydrolysate" as used herein, it is meant a polysaccharide that has been depolymerized through the addition of water to form mono and oligosaccharide sugars. Hydrolysates may be produced by enzymatic or acid hydrolysis of the polysaccharide-containing material.

Preferably, the yeast cell is able to grow under conditions similar to those found in industrial sources of pentose. The method of the present invention would be most economical when the pentose-containing material can be inoculated with the yeast variant without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. The examples below describe the fermentation of pentose in acid hydrolysates (or sulfite waste liquor) of hard woods and soft woods by the yeast cells of the present invention. It is reasonably expected that yeast strains capable of growing in sulfite waste liquor could grow be expected grow in virtually any other biomass hydrolysate.

Fermentation

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, malic acid, fumaric acid, an amino acid and ethylene.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical mamimum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermenation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following non-limiting examples are intended to be purely illustrative.

EXAMPLES

Strains and Maintenance.

For storage of the strains used in this study (Table 1), shake flask cultures were performed in complex medium (YP), consisting of 10 g l$^{-1}$ yeast extract (BD Difco) and 20 g l$^{-1}$ peptone (BD Difco), supplemented with either 2% glucose (YPD), 2% ethanol+1.5% glycerol (YP-EtOH/Glyc) or 2% arabinose (YP-Ara). Cultures were incubated at 30° C. in an orbital shaker (200 rpm) until stationary growth phase. After addition of 30% (v/v) glycerol, samples from shake-flask cultures were stored in 2 ml aliquots at −80° C.

Shake-Flask Cultivation.

Cultivation in shake flasks was performed at 30° C. in synthetic medium containing 2.3 g l$^{-1}$ urea, 6.6 g l$^{-1}$ K$_2$SO$_4$, 3 g l$^{-1}$ KH$_2$PO$_4$, 0.5 g l$^{-1}$ MgSO$_4$.7H$_2$O, and trace elements (MYurea) [7]. For shake flask cultivation, medium pH was adjusted to 4.7 with 2 M KOH prior to sterilization. After heat sterilization (121° C., 20 min), a filter-sterilized vitamin solution [7] and sugars were added. Shake-flask cultures were prepared by inoculating 100 ml medium containing the appropriate sugar in a 500-ml shake flask with a frozen stock culture, and incubated at 30° C. in an orbital shaker (200 rpm).

Anaerobic Batch Cultivation.

Anaerobic batch cultivation was carried out at 30° C. in 2 liter fermenters (Applikon, Schiedam, the Netherlands) with a working volume of 1 l. Cultures were performed in synthetic medium containing 5 g l$^{-1}$ (NH$_4$)$_2$SO$_4$, 3 g KH$_2$PO$_4$, 0.5 g l$^{-1}$ MgSO$_4$.7H$_2$O and trace elements [7]. After heat sterilization (121° C., 20 min.) the medium was supplemented with 0.01 g l$^{-1}$ ergosterol and 0.42 g l$^{-1}$ Tween 80 dissolved in ethanol [1,2], silicon antifoam, trace elements, filter sterilized vitamin solution [7], and the appropriate carbon source. Cultures were stirred at 800 rpm and sparged with 0.5 l min$^{-1}$ nitrogen gas (<10 ppm oxygen) and were maintained at pH 5.0 by automatic addition of 2 M KOH. To minimize oxygen diffusion, fermenters were equipped with Norprene tubing (Cole Palmer Instrument Company, Vernon Hills, USA). Absence of oxygen was verified with an oxygen electrode (Applisens, Schiedam, the Netherlands). Batch cultivations were started by inoculation with a 100 ml glucose-grown shake flask culture.

Growth Rate Determination.

For shake flask cultures growth profiles were made by measuring the optical density at 660 nm (OD660) in time. For anaerobic cultivations in fermenters the specific growth rates were determined based on the CO$_2$ concentrations in the exhaust gas. The specific growth rates were determined by fitting data points with an exponential curve.

Carbon Dioxide and Extracellular Metabolite Analysis.

Exhaust gas from anaerobic fermenters was cooled in a condenser (2° C.) and dried with a Permapure dryer type MD-110-48P-4 (Permapure, Toms River, USA). Carbon dioxide concentrations were determined with a NGA 2000 analyzer (Rosemount Analytical, Orrville, USA). Exhaust gas flow rates and specific carbon dioxide production rates were determined as described previously [6,8].

Glucose, arabinose, acetate, lactate, succinate, glycerol and ethanol were analyzed by HPLC using a Waters Alliance 2690 HPLC (Waters, Milford, USA) supplied with a BioRad HPX 87H column (BioRad, Hercules, USA), a Waters 2410 refractive-index detector and a Waters 2487 UV detector. The column was eluted at 60° C. with 0.5 g l$^{-1}$ sulfuric acid at a flow rate of 0.6 ml min$^{-1}$.

Hexokinase Activity Determination.

Hexokinase activity in cell extracts of the used strains in this study is determined by measuring the conversion of glucose into glucose-6-phosphate (reaction 1), using a coupled enzymatic reaction (reaction 2) that converts the formed glucose-6-phosphate into 6-phosphogluconate by the enzyme glucose-6-phosphate dehydrogenase. The rate of NADPH formed in this coupling reaction is equal to the hexokinase activity and is determined by measuring the absorbance at 340 nm.

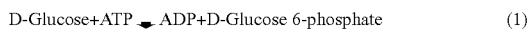
D-Glucose+ATP → ADP+D-Glucose 6-phosphate (1)

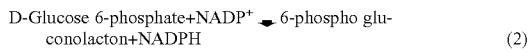
D-Glucose 6-phosphate+NADP$^+$ → 6-phospho gluconolacton+NADPH (2)

Example 1

Gene Deletions.

Gene deletions herein were achieved by integration of a G418 resistance cassette replacing the target gene. For the deletion of HXK2, HXK1 and GLK1, the KanMX cassette from pUG6 was amplified by PCR [4], using oligonucleotides indicated in Table 2.

TABLE 2

Oligonucleotides used in this study for the construction of gene deletions and related diagnostic purposes. A KanMX gene deletion cassette was obtained by PCR by using combinations of the DisA and DisB oligonucleotides. Genes were disrupted by homologues recombination between the target gene and the KanMX gene deletion cassette. Recombination sites are indicated by the underlined regions in the oligonucleotides. Deletion or disruption was confirmed by PCR using diagnostic primers KanA and KanB combined with the FW and the RV diagnostic primers corresponding with the target gene (e.g. KanA combined with HXK2-FW and KanB combined with HXK2-RV).

| Name | 5'-3' DNA sequence |
|---|---|
| Oligonucleotides used for construction of gene disruption cassettes | |
| HXK2-disA | GTTGTAGGAATATAATTCTCCACACATAATAAGTACGCTAA TTCAGCTGAAGCTTCGTACGC |
| HXK2-disB | AAAAGGGCACCTTCTTGTTGTTCAAACTTAATTTACAAATT AAGTGCATAGGCCACTAGTGGATCTG |
| HXK1-disA | TTTCTTTTAATCAAACTCACCCAAACAACTCAATTAGAATA CTGCAGCTGAAGCTTCGTACGC |
| HXK1-disB | GAATAATAATATTAAGGGAGGGAAAAACACATTTATATTTC ATTACAGCATAGGCCACTAGTGGATCTG |
| GLK1-disA | CTCGGACAAAGGTCTTCCTATGATTCCGGCGTTCGTCACCG GGTCCAGCTGAAGCTTCGTACGC |
| GLK1-disB | TAAAGGAGAGAAGATGGTAAGTACGGTGGGATACGTACACA AACATAGGCCACTAGTGGATCTG |
| Oligonucleotides used for diagnostic purposes | |
| KanA | CGCACGTCAAGACTGTCAAG |
| KanB | TCGTATGTGAATGCTGGTCG |
| HXK2-FW | TTCGCCACTGTCTTATCTAC |

TABLE 2-continued

Oligonucleotides used in this study for the
construction of gene deletions and related
diagnostic purposes. A KanMX gene deletion
cassette was obtained by PCR by using combinations
of the DisA and DisB oligonucleotides. Genes were
disrupted by homologues recombination between the
target gene and the KanMX gene deletion cassette.
Recombination sites are indicated by the under-
lined regions in the oligonucleotides. Deletion or
disruption was confirmed by PCR using diagnostic
primers KanA and KanB combined with the FW and the
RV diagnostic primers corresponding with the
target gene (e.g. KanA combined with HXK2-FW and
KanB combined with HXK2-RV).

| Name | 5'-3' DNA sequence |
|---|---|
| HXK2-RV | CCGTTCGTTCCAGAATTATC |
| HXK1-FW | CCTTAGGACCGTTGAGAGGAATAG |
| HXK1-RV | TCCCGGAGAACAAAGTAAGTGG |
| GLK1-FW | AAAAACGGGAAATAACAATAACGAC |
| GLK1-RV | TGCGATCTTATTAGTGTGTGACATT |

After purification of the PCR products (GenElute PCR Clean-up Kit, Sigma, Steinheim, Germany), overnight cultures were transformed [3] with the gene disruption cassette. Transformed cells were selected on YPD-agar containing 100 μg ml⁻ G418 (InvivoGen, San Diego, USA). Correct integration of the KanMX cassette was verified by PCR on single colonies using diagnostic oligonucleotides that bind to the KanMX cassette and regions up- and downstream of the target gene (Table 1).

For multiple gene deletions, the KanMX marker was rescued before deletion of the next gene. To this end, cells were transformed with pSH65, expressing the inducible Cre-recombinase and carrying the phleomycin resistance gene $ble^r$ [5]. Transformed cells were spread on YPD plates containing phleomycin and incubated at 30° C. until colonies appeared. Liquid YP-galactose containing 7.5 μg/ml phleomycin (InvivoGen, San Diego, USA) was inoculated with several phleomycin resistant colonies, incubated overnight at 30° C. for induction of the Cre-recombinase, and transferred to solid YPD with phleomycin. Removal of the KanMX cassette by the Cre-recombinase was confirmed by replica plating of phleomycin-resistant yeast colonies on YPD and YPD-G418 and by diagnostic PCR on single colonies that had lost G418 resistance. Subsequently, loss of pSH65 was achieved by growing cells non-selectively for 5-10 generations in YPD without phleomycin, after which loss of phleomycin resistance was confirmed by replica plating of single colonies on solid YPD with and without phleomycin. Subsequent deletion of HXK2, HXK1 and GLK1, and removal of the KanMX gene after each deletion, resulted in strains IMK306, IMK307, IMK311, IMK312 and IMK318 (Table 3).

TABLE 3

S. cerevisiae strains constructed and used herein.

| Strain | Relevant genotype/characteristics |
|---|---|
| DS62504 | MAT a MAL2-8c SUC2 ygr059w::{TDH3p-araA; ENO1p-araB; PGI1p-araD} gre3::{TPI1p-TAL1; ADH1p-TKL1; PGI1p-RPE1; ENO1p-RKI1} yel023c::{TPI1p-XylA; TDH1p-XKS1} |
| IMK306 | As DS62504; Δhxk2::LoxP-KanMX-LoxP |
| IMK307 | As DS62504; Δhxk2::LoxP |
| IMK311 | As DS62504; Δhxk2::LoxP Δhxk1::LoxP-KanMX-LoxP |
| IMK312 | As DS62504; Δhxk2::LoxP Δhxk1::LoxP |
| IMK318 | As DS62504; Δhxk2::LoxP Δhxk1::LoxP glk1::LoxP-KanMX-LoxP |
| IMW017 | As DS62504; Δhxk2::LoxP Δhxk1::LoxP glk1::LoxP-KanMX-LoxP; single colony isolate derived from IMK318, selected for glucose-insensitive arabinose consumption; co-consuming glucose and arabinose |
| IMW018 | As DS62504; Δhxk2::LoxP Δhxk1::LoxP glk1::LoxP-KanMX-LoxP; single colony isolate derived from IMK318, selected for glucose-insensitive arabinose consumption; consuming arabinose in the presence of >2% (w/v) glucose |

The Effect of hxk2 and hxk2 hxk1 Deletion on Glucose and Arabinose Consumption.

To determine the effect of HXK2 and HXK1 deletion on glucose and arabinose consumption, strains DS62504, IMK307 (hxk2Δ) and IMK311/IMK312 (hxk2Δ hxk1Δ) were cultivated both in shake flasks (FIG. 1) and anaerobic fermenters (FIG. 2) at 30° C. in MY supplemented with a mixture of 2% arabinose and 2% glucose.

The shake flask cultures were started at an initial OD660 of approximately 0.05 by inoculation with shake flask cultures grown in MY-glc. Strain DS62504 (FIG. 1) consumed glucose within 21 hours and upon glucose depletion, arabinose consumption started. Both sugars were consumed in a total time of more than 50 hours. In the culture of strain IMK307 (FIG. 1), glucose was totally consumed with 25 hours and arabinose was depleted in less than 15 hours after that. Overall IMK307 demonstrated an at least 20% reduction in total fermentation time compared to DS62504. Strain IMK311 (FIG. 1) consumed 2% glucose within approximately 30 hours. With still approximately 10 mM of glucose left in the culture, arabinose consumption was observed. The arabinose was completed within 48 hours. Although slower than IMK307, the overall fermentation time of IMK311 was still shorter than that of DS62504.

The anaerobic cultivations (FIG. 2) were started at an initial OD660 of approximately 1 by inoculation with shake flaks cultures grown in MY-glc. Based on the $CO_2$ production profile it could be deduced that strain DS64205 completely consumed the glucose within less than 15 hours. The specific growth rate during glucose consumption was 0.29 $h^{-1}$. The arabinose however, was consumed at a much lower rate. After 80 hours, approximately 90% of the arabinose is still present in the fermentation broth. Glucose consumption for strain IMK307 (hxk2Δ) was slower. Both the $CO_2$ production profile and the glucose measurements indicated that all the glucose was consumed within 20 hours. The specific growth rate during glucose consumption was 0.20 $h^{-1}$. Arabinose consumption started upon glucose depletion and 92% of the arabinose was consumed within 66 hours, which is a clear improvement if compared to strain DS62504. Deletion of HXK1 additional to HXK2 (strain IMK312) had a severe effect on the specific growth rate on glucose. The growth rate 0.05 $h^{-1}$ for strain IMK312 was 75% lower than that of strain IMK307. Glucose was depleted within 46 hours. Within these 46 hours, approximately 10% of the total of 132 mM of arabinose was consumed. Arabinose was completely consumed within less than 112 hours.

Example 2

Selection of IMK318 Growing on Arabinose in the Presence of Glucose.

It was confirmed by 450 hours of cultivation in shake flasks on glucose that the hexokinase/glucokinase deletion strain IMK318 (hxk1Δ hxk2Δ glk1Δ) is unable to grow on glucose alone. Therefore the strain was cultivated in YP-EtOH/Glyc and subsequently stored at −80° C. after the addition of glycerol. Subsequently, IMK318 was cultivated in 100 ml MY containing 2% arabinose. After 3 days, at an OD660 of approximately 1, 2 ml of the culture was transferred to 100 ml fresh MY containing 2% arabinose. After approximately 12 days the OD660 of the culture was >5 and samples were stored at −80° C. as glycerol stocks. Strain IMK318 was cultivated at 30° C. for several days in MY-ara. At an OD660 of approximately 5, 2 ml of the culture was transferred to 6 separate shake flasks containing 100 ml MYurea supplemented with 2% arabinose and varying concentrations of glucose: 0, 0.11, 0.23, 0.65, 1.3 and 2.5 (w/v) %. Growth of these 6 parallel cultures was recorded by OD660 measurements (FIG. 3). It was observed that, in the presence of glucose, growth is delayed. An increasing amount of glucose resulted in an increasingly delayed growth on arabinose. Two of these parallel cultures (Line A which started at 0.65 w/v % glucose; Line B which started at 2.5 w/v % glucose) were transferred serially to 100 ml MY supplemented with arabinose and glucose according to the transfer-schemes shown in Table 4.

TABLE 4

Schematic representation of serially transferred shake flask cultures (SF) of strain IMK318 in MYurea with arabinose (ara) and glucose (glc) concentrations as indicated. Transfer series A and B finally resulted in single colony isolates IMW018 and IMW017 respectively.

| Series | SF1 | SF2 | SF3 | SF4 | SF5 | SF6 | SF7 | Single colony isolate |
|---|---|---|---|---|---|---|---|---|
| A | 2% Ara | 2% Ara | 2% Ara | 2% Ara | 2% Ara | 2% Ara | 2% Ara | IMW018 |
|   | 0.65 Glc | 1% Glc | 2.5% Glc | 2% Glc | 2% Glc | 2% Glc | 2% Glc | |
| B | 2% Ara | 2% Ara | 2% Ara | | | | | IMW017 |
|   | 2.5% Glc | 2% Glc | 2% Glc | | | | | |

In series A, where cultures were transferred to medium with increasing concentrations of glucose (Table 3), arabinose is completely consumed while less than 10% of the glucose was consumed (FIG. 4). From SF7, samples were spread on solid YP-ara supplemented with 100 μg ml$^{-1}$ G418 and incubated at 30° C. until colonies appeared. Separate colonies were transferred to solid YP-ara. Single colony isolates were cultivated in YP-ara and stored at −80° C. Two single colony isolates of this series of serially transferred shake flasks were tested and found qualitatively similar to the mixed culture. One of these isolates was designated as strain IMW018.

In series B (Table 3), shake flask cultures were transferred in MY medium with fixed concentrations of 2% arabinose and 2% glucose (FIG. 5). Surprisingly, co-consumption of arabinose and glucose was observed after the first transfer (SF1→SF2). From SF3, samples were spread on solid YP-ara supplemented with 100 μg ml$^{-1}$ G418 and incubated at 30° C. until colonies appeared. Separate colonies were transferred to solid YP-ara. Single colony isolates were cultivated in YP-ara and stored at −80° C. as glycerol stocks. Two single colony isolates of this series of serially transferred shake flasks were tested and found qualitatively similar to the mixed culture. One of these isolates was designated as strain IMW017.

Glucose and arabinose consumption of both single colony isolate strains IMW017 and IMW018 was tested in shake flask cultures (FIGS. 4 and 5). The single colony isolates exhibited glucose- and arabinose concentration profiles that were similar to the serially transferred shake flask cultures they originate from. Interestingly, the glucose concentration regimes applied in this evolutionary engineering strategy based on the hexokinase/glucokinase deletion strain IMK318 (hxk1Δ hxk2Δ glk1Δ), resulted in two different phenotypes: (i) Glucose-insensitive arabinose consumption by strain IMW018, and (ii) Co-consumption of arabinose and glucose by strain IMW017.

Example 3

Anaerobic Co-Fermentation of Arabinose and Glucose.

Strain IMW017 was cultivated anaerobically in a mixture of glucose and arabinose, using a sequential batch fermenter set-up. Three consecutive batches in the glucose/arabinose mixture were performed (FIG. 6). In each batch glucose and arabinose were consumed simultaneously and was fermented into ethanol. Deduced from the $CO_2$ production profile, it was observed that the specific growth rate on the glucose/arabinose mixture increased from 0.05 h$^{-1}$ in the first batch to 0.07 h$^{-1}$ in the third batch.

During further consecutive batch fermentations, the growth rate is increased even further. A single colony isolate strain taken from the final batch, exhibits glucose and arabinose co-consumption at an increased specific consumption rates compared to IMW017.

Example 4

Hexokinase Activities.

The hexokinase activities in cell-extracts of strains DS62504, IMK307, IMK312, IMK318, IMW017 and IMW018 are determined. The hexokinase activity in cell extracts of IMK307 (hxk2Δ) are lower than that of strain DS62504. The hexokinase activity of IMK312 (hxk2Δ hxk1Δ) are lower than that of IMK307, whereas IMK318 (hxk2Δ hxk1Δ glk1Δ) exhibits no/the lowest_hexokinase activity. Hexokinase activities in strain IMW018 are similar to hexokinase activities observed for IMK318, whereas IMW017 has higher hexokinase acitivities than IMK318.

Example 5

Identification of an Unknown Hexokinase in IMW017.

Based on the measured hexokinase activity in the evolved hxk1 hxk2 glk1 strains, it is expected that another gene with the potential to encode a sugar kinase present in the genome had either become active or changed its substrate specificity to glucose. The gene encoding this activity is identified by genomics analysis. Additional deletion of this gene results in a decrease of the hexokinase activity. This quadruple knock-out strain provides an even stronger platform for evolutionary engineering of arabinose consumption in the presence of glucose.

Example 6

Re-Introduction of Hexokinase or Glucokinase Activity in IMK318.

To restore growth on glucose, either HXK1, HXK2 or GLK1 is re-introduced into IMK318. Activity measurements show that reintroduction of one of these genes in IMK318 results in increased hexo/glucokinase activity. Growth on glucose as the sole carbon source is restored.

Example 7

Re-Introduction of Hexokinase or Glucokinase Activity in IMW018.

Activity measurements show that reintroduction of either HXK1, HXK2 or GLK1 in IMW018 results in increased hexo/glucokinase activity compared to strain IMW018. Growth on glucose as the sole carbon source is restored. Reintroduction of either HXK1, HXK2 or GLK1 results in growth on both glucose and arabinose as sole carbon source. The resulting strain grows in a mixture of glucose and arabinose, exhibiting co-consumption of glucose and arabinose.

Example 8

Identification of Underlying Mutations of the Glucose-Insensitive Phenotype of IMW017 and IMW018.

It is expected that the glucose-insensitive phenotype of strains IMW017 and IMW018 can be explained by mutations that have been gathered during selective growth of strain IMK318 in medium containing glucose and arabinose. To identify these mutations, the genomes of strains IMK318, IMW017 and IMW018 are sequenced. By comparing the genome sequences of IMW017 vs IMK318 and IMW018 vs IMK318 genomic modifications, like e.g. single nucleotide polymorphisms, are identified. Introduction of these single nucleotide polymorphisms in DS62504 results in phenotypes of which growth on arabinose is insensitive to glucose.

Example 9

Deletion of GAL1.

Another approach to determine the protein(s) responsible for the remaining hexokinase activity is to delete genes that potentially encode hexokinase activity in the hxk1 hxk2 glk1 strain. To this aim, the GAL1 gene is deleted in the hxk1 hxk2 glk1 strain. The resulting strain shows lower hexokinase activity than the parental hxk1 hxk2 glk1 strain or shows a decreased ability to grow on glucose as the sole carbon source compared to the parental hxk1 hxk2 glk1 strain. This quadruple knock-out strain provides an even stronger platform for evolutionary engineering of arabinose consumption in the presence of glucose.

Example 10

Deletion of YDR516C.

Another approach to determine the protein(s) responsible for the remaining hexokinase activity is to delete genes that potentially encode hexokinase activity in the hxk1 hxk2 glk1 strain. To this aim, the YDR516C gene is deleted in the hxk1 hxk2 glk1 strain. The resulting strain shows lower hexokinase activity than the parental hxk1 hxk2 glk1 strain or shows a decreased ability to grow on glucose as the sole carbon source compared to the parental hxk1 hxk2 glk1 strain. This quadruple knock-out strain provides an even stronger platform for evolutionary engineering of arabinose consumption in the presence of glucose.

Example 11

Deletion of YLR446W.

Another approach to determine the protein(s) responsible for the remaining hexokinase activity is to delete genes that potentially encode hexokinase activity in the hxk1 hxk2 glk1 strain. To this aim, the YLR446W gene is deleted in the hxk1 hxk2 glk1 strain. The resulting strain shows lower hexokinase activity than the parental hxk1 hxk2 glk1 strain or shows a decreased ability to grow on glucose as the sole carbon source compared to the parental hxk1 hxk2 glk1 strain. This quadruple knock-out strain provides an even stronger platform for evolutionary engineering of arabinose consumption in the presence of glucose.

Example 12

Anaerobic Co-Fermentation of Arabinose and Glucose.

To improve co-consumption of glucose and arabinose of strain IMW017, strain IMW017 was cultivated anaerobically in MY supplied with a mixture of 20 g/liter glucose and 20 g/liter arabinose, using a sequential batch fermenter set-up. Initially, four consecutive batches in the glucose/arabinose mixture were performed. In each batch glucose and arabinose were consumed simultaneously and was fermented into ethanol (FIG. 6, example 3). Deduced from the $CO_2$ production profile, it was observed that the specific growth rate on the glucose/arabinose mixture increased from 0.05 $h^{-1}$ in the first batch to 0.06 $h^{-1}$ in the fourth batch. After the fourth batch, consecutive batch cultivations were performed in either mixtures of glucose and arabinose (batch nrs 6, 7, 9, 11, 13, 15, 17, 21, 23, 25, 27, 29, 31, 33, 35, 37 and 39) or arabinose only (batch nrs 5, 8, 10, 12, 14, 16, 18, 19, 20, 22, 24, 26, 28, 30, 32, 34, 36, 38 and 40). After 19 and 21 batches in MY-arabinose and MY-glucose/arabinose respectively, the anaerobic growth rate increased to 0.09 $h^{-1}$ on arabinose as sole carbon source and 0.10 $h^{-1}$ on the glucose/arabinose mixture (FIG. 7). Comparison of the $CO_2$ production profiles of the individual batch cultivations shows that the repeated batch regime has resulted in a decreased fermentation time for either arabinose only or the glucose/arabinose mixture from approximately 120 hours to approximately 80 hours, assuming an equal initial inoculum size for each batch (FIG. 8). The single peak of $CO_2$ production that was observed for the batch cultivations in the glucose/arabinose mixture indicates that glucose and arabinose are consumed simultaneously, rather than sequentially (FIGS. 8 and 9).

Example 13

Hexokinase Activities.

The hexokinase activities of strains DS62504, IMK307, IMK312, IMK318, IMW017 and IMW018 were determined in cell-extracts of shake flask cultures grown in YP supplied with arabinose. The hexokinase reaction mixture consisted of 50 mM imidazole-HCl, pH 7.6, 1 mM $NADP^+$, 10 mM $MgCl_2$, 2 U glucose-6-phosphate dehydrogenase, 10 mm D-glucose and cell extract. The reaction was started by the addition of 1 mM ATP and the formation of NADPH was determined by measuring the absorbance of the reaction mixture at 340 nm. The hexokinase activity in cell extracts of strains DS62504 and IMK307 (hxk2Δ) were 1.2 and 1.3 µmol·min$^{-1}$·mg$^{-1}$ protein respectively (FIG. 10). The hexokinase activity of 0.4 µmol·min$^{-1}$·mg$^{-1}$ protein in cell extracts of IMK312 (hxk2Δ hxk1Δ) was lower than that of IMK307. Strains IMK318 and IMW018 (hxk2Δ hxk1Δ glk1Δ) exhibited a hexokinase activity of less than 0.02 µmol·min$^{-1}$·mg$^{-1}$ protein. Strain IMW017, being able to consume glucose despite the triple hxk2 hxk1 and glk1 deletions, was expected to have a higher hexokinase activity compared to strain IMK318 and IMW018, both not being able to consume glucose. Hexokinase activity for strain IMW017 was also less than 0.02 µmol·min$^{-1}$·mg$^{-1}$ protein under the assay conditions.

Example 14

Identification of GAL1 as a Hexokinase in IMW017.

Based on growth experiments of the evolved hxk1Δ hxk2Δ glk1Δ strain IMW017 on mixtures of glucose and arabinose, it was expected that another gene with the potential to encode a sugar kinase present in the genome had either become active or changed its substrate specificity to glucose. To investigate whether the unknown hexokinase activity was encoded by GAL1, the GAL1 gene was deleted in IMW017. After removal of the KanMX cassette from the glk1 locus using pSH65 (see example 1), GAL1 deletion was achieved by integration of a G418 resistance cassette that was amplified by PCR using oligonucleotides GAL1-DisA and GAL1-DisB (Table 5). Transformed cells were selected on YP-agar containing 100 µg ml⁻ G418 (InvivoGen, San Diego, USA) and 1.5% (w/v) ethanol and 1.5% (w/v) glycerol as carbon source. Correct integration of the KanMX cassette was verified by PCR on single colonies using combinations of the diagnostic oligonucleotides GAL1-FW2/KanA and GAL1-RV2/KanB. (Table 4). Deletion of GAL1 in the resulting strain IMW023 was confirmed by the inablity to grown on galactose as sole carbon source.

Interestingely, IMW023 was not able to use glucose as carbon source, indicating that GAL1 was responsible for the unknown hexokinase activity in its parental hxk1Δ, hxk2Δ, glk1Δ, strain IMW017. During a shake flask cultivation in a mixture of glucose and arabinose, IMW023 did not consume glucose while arabinose was consumed (FIG. 11).

TABLE 5

Oligonucleotides used in this study for the deletion of GAL1 and related diagnostic purposes. A KanMX gene deletion cassette was obtained by PCR by using combinations of the GAL1-DisA and GAL1-DisB oligonucleotides. GAL1 was disrupted by homologues recombination between the target gene and the KanMX gene deletion cassette. Recombination sites are indicated by the underlined regions in the oligonucleotides. Deletion or disruption was confirmed by PCR using diagnostic primers KanA and KanB combined with the FW and the RV diagnostic primers corresponding with the target gene.

| | |
|---|---|
| GAL1-DisA | <u>TAATATACCTCTATACTTTAACGTCAAGGAGAAAAAACTAT</u>AATGCAGCTGAAGCTTCGTACGC |
| GAL1-DisB | <u>AATGAGAAGTTGTTCTGAACAAAGTAAAAAAAGAAGTATA</u>CTTACATAGGCCACTAGTGGATCTG |
| KanA | CGCACGTCAAGACTGTCAAG |

TABLE 5-continued

Oligonucleotides used in this study for the deletion of GAL1 and related diagnostic purposes. A KanMX gene deletion cassette was obtained by PCR by using combinations of the GAL1-DisA and GAL1-DisB oligonucleotides. GAL1 was disrupted by homologues recombination between the target gene and the KanMX gene deletion cassette. Recombination sites are indicated by the underlined regions in the oligonucleotides. Deletion or disruption was confirmed by PCR using diagnostic primers KanA and KanB combined with the FW and the RV diagnostic primers corresponding with the target gene.

| | |
|---|---|
| KanB | TCGTATGTGAATGCTGGTCG |
| GAL1-FW2 | ATGGCATTATACTCCTGCTAGAAAG |
| GAL1-RV2 | AAAGGATGGCAGAGCATGTTATCG |

Example 15

Towards Anaerobic Fermentation of Arabinose in the Presence of Glucose.

Since it was found that GAL1p in IMW017 also exhibits hexokinase activity, the hxk1Δ hxk2Δ glk1Δ gal1Δ strain IMW023 provides a more solid platform to improve arabinose consumption in the presence of glucose by evolutionary engineering, without glucose being consumed. To select for improved arabinose consumption in the presence of glucose in the medium, strain IMW023 was cultivated in shake flask cultures by serial transfer in MY medium supplied with 2% arabinose and 2% glucose. Growth was monitored by OD660 measurements and specific growth rates were estimated from either 2 or 3 OD660 measurements per culture. Glucose and arabinose concentrations were determined by HPLC analysis. After 24 serial transfers on the arabinose/glucose mixtures in 63 days, the transferred culture of strain IMW023 was still able to grow on arabinose in the presence of 2% glucose, without consuming glucose (FIG. 12). The specific growth rate on arabinose increased from approximately 0.06 h$^{-1}$ to approximately 0.11 h$^{-1}$ (FIG. 13).

To select for cells that are able to consume arabinose in the presence of glucose under anaerobic conditions, and to further improve the arabinose consumption in the presence of glucose, the sequential transfer of strain IMW023 in MY medium supplied with 2% arabinose and 2% glucose was continued in an anaerobic sequential batch fermentation setup. For this, the final shake flask culture of the serially transferred culture (SF24) of strain IMW023 was used as inoculum. In the first 1000 hours of cultivation, increased CO$_2$ production was only observed when air was supplied to the headspace of the fermenter in stead of nitrogen gas (FIG. 14). After approximately 1000 hours of cultivation during the fourth batch, an increase of the CO$_2$ concentrations in the exhaust gas was observed. Deduced from the CO$_2$ production profile, this first batch of anaerobic growth exhibited a specific growth rate of approximately 0.03 h$^{-1}$. After another ten transfers, the specific growth rate increased to approximately 0.06 h$^{-1}$ (FIG. 14). During the sequentially transferred batch cultures arabinose was consumed while glucose was not (FIG. 15). The CO$_2$ production profiles of the individual batch cultivations show that the rate of CO$_2$ production, and thus the arabinose consumption rate, has increased during the sequential transfers, which has resulted in a decrease of the fermentation time needed to completely consume arabinose (FIG. 16).

A single colony isolate taken from the final batch, designated as strain IMW058, exhibits increased arabinose consumption rates in the presence of glucose compared to IMW023.

Example 16

Re-Introduction of Hexokinase or Glucokinase Activity in IMW018.

Reintroduction of either HXK1, HXK2 or GLK1 in strain IMW018 was performed to restore growth on glucose. For this, HXK2, HXK1 and GLK1 were amplified by PCR using oligonucleotide combinations HXK2FW/HXK2RV, HXK1 FW/HXK1RV and GLK1 FW/GLK1RV, using genomic DNA of S. cerevisiae CENPK113-7D as a template. After purification of the PCR products (GenElute PCR Clean-up Kit, Sigma, Steinheim, Germany), an overnight culture of IMW018 was transformed (Gietz and Woods 2002) with the PCR products. Transformed cells were selected for growth on glucose on MY-agar containing 2% of glucose. Correct integration of HXK2, HXK1 and GLK1 by homologous recombination at their original locus was verified by PCR on single colonies using the diagnostic primer pairs (TABLE 6).

The resulting strains IMW024 (HXK2), IMW025 (HXK1) and IMW047 (GLK1) were cultivated with an initial OD660 of 0.05±0.01 in shake flasks at 30° C. in MY-urea medium (pH 4.7) supplied with 2% glucose and 2% arabinose, using precultures grown on glucose. For comparison, strains DS62504, IMK307 and IMK311 were cultivated under the same conditions. Growth and sugar consumption was monitored for 69 hours. Strains IMW024, IMW025 and IMW047 were all able to utilize both glucose and arabinose (FIG. 17). Re-introduction of GLK1 in IMW018 (IMW047) resulted in fast glucose and arabinose consumption. Arabinose and glucose were completed within 43 hours of cultivation, which is similar to what was observed for IMK307 (hxk2Δ) and IMK311 (hxk1Δ hxk2Δ). The arabinose consumption observed for IMW024 (HXK2) and IMW025 (HXK1) was both slower than for IMK307 and IMK311, however faster than for the parental strain DS62504 without any HXK/GLK deletions (FIG. 17 (a)). Co-consumption of arabinose and glucose was only observed for strain IMW047 (FIG. 18). Before glucose was depleted at 22 hours, approximately 7% of the arabinose was consumed. At 25 hours, when glucose was completely consumed, 19% of the arabinose was utilized.

TABLE 6

Oligonucleotides used in this study for the amplification of HXK2, HXK1 and GLK1. Integration of these PCR products at their original locus was verified by PCR using diagnostic primers of which their annealing sites are located on the insert and in the flanking regions of the integration site.

| Amplification primer pair | DNA sequence |
|---|---|
| HXK2-FW/ | TTCGCCACTGTCTTATCTAC |
| HXK2-RV | CCGTTCGTTCCAGAATTATC |
| HXK1-FW/ | CCTTAGGACCGTTGAGAGGAATAG |
| HXK1-RV | TCCCGGAGAACAAAGTAAGTGG |
| GLK1-FW/ | AAAAACGGGAAATAACAATAACGAC |
| GLK1-RV | TGCGATCTTATTAGTGTGTGACATT |

| Diagnostic primer pair | DNA sequence |
|---|---|
| HXK2-FW2/ | GATTGCGAGATCCACGAAATTACC |
| HXK2-RV2 | AATCACCGGATTCCTTACCAGTTG |
| HXK2-FW3/ | GAAATTCACGGGATTTATTCGTGAC |
| HXK2-RV3 | TTTCCATGTTTCTAAGCGTAGTGAG |
| HXK1-FW2/ | CCCGTTTGTTGGAAGATAGC |
| HXK1-RV2 | CACATCAGCCATGGAACC |
| HXK1-FW3/ | GCAGGTGCTGCTGTTATTG |
| HXK1-RV3 | CCGAGCTATCCTACGACTTTC |
| GLK1-FW4/ | GCCCGACAGGGTAACATATTATC |
| GLK1-RV4 | CCGGAATCATAGGAAGACCTTTG |
| GLK1-FW5/ | AGAGGAAGGTGCACTTGAAGATTG |
| GLK1-RV5 | ATAAGATGGAATTGGCCGGTCTTG |

Example 17

Re-Introduction of Hexokinase or Glucokinase Activity in IMW058.

Reintroduction of either HXK1, HXK2 or GLK1 in strain IMW058 was performed to restore growth on glucose. For this, HXK2, HXK1 and GLK1 were amplified by PCR using oligonucleotide combinations HXK2FW/HXK2RV, HXK1 FW/HXK1RV and GLK1 FW/GLK1RV, using genomic DNA of S. cerevisiae CENPK113-7D as a template. After purification of the PCR products (GenElute PCR Clean-up Kit, Sigma, Steinheim, Germany), an overnight culture of IMW058 was transformed (Gietz and Woods 2002) with the PCR products. Transformed cells were selected for growth on glucose on MY-agar containing 2% of glucose. Correct integration of HXK2, HXK1 and GLK1 by homologeous recombination at their original locus was verified by PCR on single colonies using diagnostic oligonucleotides (TABLE 5).

The resulting strains IMW059 (HXK2), IMW060 (HXK1) and IMW061 (GLK1) were cultivated with an initial OD660 of 0.05±0.01 in shake flasks at 30° C. in MY-urea medium (pH 4.7) supplied with 2% glucose and 2% arabinose, using precultures grown on glucose. Growth and sugar consumption was monitored for 72 hours. Strains IMW059, IMW060 and IMW061 were all able to utilize both glucose and arabinose (FIG. 17). Re-introduction of HXK2 in IMW058 resulted in fast sequential consumption of arabinose and glucose. While the reference strain DS62504 did not completely consume the arabinose within 69 hours (FIG. 17 (a)), strain IMW059 consumed more than 99% of the arabinose within approximately 46 hours (FIG. 17 (j)).

For strains IMW060 (HXK1) and IMW061 (GLK1) simultaneous consumption of glucose and arabinose was observed (FIGS. 17 (k) and (l)). In the first 22 hours of cultivation, approximately 18% of the arabinose was co-consumed together with approximately 48% of the glucose. Within 50 hours of cultivation, 99% of the arabinose was consumed.

Example 18

Comparative Whole Genome Sequencing of Strains IMK318, IMW017 and IMW018.

Whole genome DNA sequencing for strains IMK318, IMW017 and IMW018 was performed using Illumina GAIIx technology (75 bp reads, paired-ends). Sequence reads were aligned to a reference genome sequence of *S. cerevisiae* CEN.PK 113-7D using CLC Genomics Workbench version 4.5. SNP analysis was performed using CLC Genomics Workbench version 4.5.

In total, SNP analysis yielded four mutations in coding regions resulting in an aminoacid change when IMK318, IMW017 and IMW018 were compared to the reference sequence of CEN.PK 113-7D.

One mutation, resulting in a Asp376Val amino acid change in GAL1 which encodes galactokinase. The mutation was found in IMK318, IMW017 and IMW018 when compared to the reference sequence (FIG. 19).

Surprisingly, only two unique mutations for IMW017 were found. One of them, a Tyr274Phe mutation in GAL1, is located in the galactose binding site of galactokinase, which was described by Thoden et al. (2005). Combined with the observation that deletion of GAL1 in IMW017 eliminates growth on glucose, it seems likely that this mutation is responsible for the hexokinase activity of GAL1 that allowed glucose consumption in IMW017. A second mutation was found in transmembrane motif 5 of GAL2 (Thr219Asn), which encodes the galactose permease in *S. cerevisiae*. GAL2p is known to be able to transport arabinose (Kou et. al 1970; Becker et al. 2003). A mutation in GAL2 that increases the affinity for arabinose or decreases the affinity for glucose, will result in improved arabinose consumption in the presence of glucose.

Surprisingly, only 1 unique mutation was found in the coding regions of IMW018. This mutation was located in transmembrane motif 8 of GAL2 (Asn376Ser), which encodes the galactose permease in *S. cerevisiae*. GAL2p is known to be able to transport arabinose (Kou et. al 1970; Becker et al. 2003). A mutation in GAL2 that increases the affinity for arabinose or decreases the affinity for glucose, will result in improved arabinose consumption in the presence of glucose.

Example 19

Fast Anaerobic Fermentation of Glucose and Arabinose by IMW059

Strain IMW059 was cultivated anaerobically in MY medium with 20 g $l^{-1}$ glucose and 20 g $l^{-1}$ arabinose. Sugar consumption was monitored by HPLC measurements. Growth of the yeast was determined by dry weight meaurements and monitoring the OD660. $CO_2$ production was determined by measuring $CO_2$ concentrations in the exhaust gas. Ethanol production was calculated based on the $CO_2$ production. To correct for ethanol evaporation the amount of ethanol produced was assumed to be equal to the measured cumulative production of $CO_2$ minus the $CO_2$ production that occurred due to biomass synthesis (5.85 mmol $CO_2$ per gram biomass) and the $CO_2$ associated with acetate formation.

Within 19 hours the glucose was depleted. Based on the $CO_2$ production profile and arabinose concentrations (FIG. 21) arabinose consumption started after the glucose was completely consumed. No co-consumption of glucose and arabinose was observed. After 74 hours of anaerobic cultivation 99% of the arabinose was consumed. Ethanol was produced with an overall yield of 0.43 g $g^{-1}$ of total sugar. Comparison of the $CO_2$ production profile to that of strain DS62504 (FIG. 24) shows that, based on the first $CO_2$ production peak during anaerobic fermentation of a glucose/arabinose mixture, glucose consumption is slower for strain IMW059. Arabinose however, is consumed much faster by IMW059, which is reflected by the higher $CO_2$ production levels during the second $CO_2$ production peak and the shorter total fermentation time.

Example 20

Anaerobic Co-Consumption of Glucose and Arabinose by IMW060

Strain IMW060 was cultivated anaerobically in MY medium with 20 g $l^{-1}$ glucose and 20 g $l^{-1}$ arabinose. Sugar consumption was monitored by HPLC measurements. Growth of the yeast was determined by dry weight meaurements and monitoring the OD660. $CO_2$ production was determined by measuring $CO_2$ concentrations in the exhaust gas. Ethanol production was calculated based on the $CO_2$ production. To correct for ethanol evaporation the amount of ethanol produced was assumed to be equal to the measured cumulative production of $CO_2$ minus the $CO_2$ production that occurred due to biomass synthesis (5.85 mmol $CO_2$ per gram biomass) and the $CO_2$ associated with acetate formation.

Based on the $CO_2$ production profile and glucose and arabinose concentrations (FIG. 22) arabinose is simultaneously consumed with glucose within the first approximately 40 hours. Within the first 43 hours glucose is completely consumed while 41% of the arabinose was consumed. After 74 hours of anaerobic cultivation 89% of the arabinose was consumed. After 140 hours of anaerobic cultivation 98% of the arabinose was consumed. Ethanol was produced with an overall yield of 0.43 g $g^{-1}$ of total sugar. Comparison of the $CO_2$ production profile to that of strain DS62504 (FIG. 24) shows that, based on the first $CO_2$ production peak during anaerobic fermentation of a glucose/arabinose mixture, glucose consumption is slower for strain IMW060. The total time to ferment the glucose/arabinose mixture however, is shorter than that of DS62504.

Example 21

Anaerobic Co-Consumption of Glucose and Arabinose by IMW061

Strain IMW061 was cultivated anaerobically in MY medium with 20 g $l^{-1}$ glucose and 20 g $l^{-1}$ arabinose. Sugar consumption was monitored by HPLC measurements. Growth of the yeast was determined by dry weight meaurements and monitoring the OD660. $CO_2$ production was determined by measuring $CO_2$ concentrations in the exhaust gas. Ethanol production was calculated based on the $CO_2$ production. To correct for ethanol evaporation the amount of ethanol produced was assumed to be equal to the measured cumulative production of $CO_2$ minus the $CO_2$ production that occurred due to biomass synthesis (5.85 mmol $CO_2$ per gram biomass) and the $CO_2$ associated with acetate formation.

Based on the $CO_2$ production profile and glucose and arabinose concentrations (FIG. 23) arabinose is simultaneously consumed with glucose within the first 43 hours. Within the first 49 hours glucose is completely consumed while 73% of the arabinose was consumed. After 74 hours of anaerobic cultivation 95% of the arabinose was consumed. After 140 hours of anaerobic cultivation 99% of the arabinose was consumed. Ethanol was produced with an overall yield of 0.44 g $g^{-1}$ of total sugar. Comparison of the $CO_2$ production profile to that of strain DS62504 (FIG. 24) shows that, based on the first CO$_2$ production peak during anaerobic fermentation of a glucose/arabinose mixture, glucose consumption is slower for strain IMW061. The total time to ferment the glucose/arabinose mixture however, is shorter than that of DS62504.

Example 22

Performance Test in BAM

In order to test the performance of the strains IMW060 and IMW061, the strains were inoculated in Verduyn medium, supplemented with 2% glucose. As controls, strain DS62504, was included.

After overnight incubation at 30° C. and 280 rpm in a rotary shaker, cells were harvested by centrifugation and cultivations for CO$_2$ production were performed at 33° C. in the BAM (Biological Activity Monitor), in 100 ml Verduyn medium supplemented with the sugars indicated in table 7. The cells were added to the 100 ml of Verduyn medium supplemented with the sugars and the inhibitors acetic acid, coumaric acid, ferulic acid, furfural, HMF and formic acid at the indicated concentrations. In a second experiment, 100 ml of Verduyn medium supplemented with the sugars but without inhibitors was used. The CO$_2$ production was constantly monitored, and samples were taken at intervals for analysis (optical density at 600 nm, ethanol, and residual sugars).

The results of the BAM experiment are shown in FIGS. 25, 26, and 27 for the medium with inhibitors and 28, 29 and 30 for the medium without inhibitors. It can be concluded that both IMW060 and IMW061 are capable of converting the sugars glucose and arabinose fast and simultaneously into ethanol, while the strain DS62504 can not, i.e DS62504 consumes arabinose after the glucose is exhausted from the medium. The same result, i.e. co-consumption of arabinose and glucose, is obtained in the presence of inhibitors, although the time it takes to consume all sugars is slower in the presence of inhibitors, as is known from the literature.

TABLE 7

Composition of the Verduyn medium CFMM2M; CFMM1M has the same composition except without inhibitors:

| Component | Amount (g/l) |
| --- | --- |
| Glucose | 55 |
| Arabinose | 35 |
| Mannose | 5 |
| Acetic Acid | 3.0 |
| Coumaric Acid* | 0.03 |
| Ferulic Acid* | 0.2 |
| Furfural** | 0.1 |
| HMF | 0.1 |
| Formic Acid | 0.1 |

REFERENCES

[1] A. A. Andreasen, T. J. Stier, Anaerobic nutrition of *Saccharomyces cerevisiae*. I. Ergosterol requirement for growth in a defined medium, J. Cell Physiol. 41 (1953) 23-36.
[2] A. A. Andreasen, T. J. Stier, Anaerobic nutrition of *Saccharomyces cerevisiae*. II. Unsaturated fatty acid requirement for growth in a defined medium, J. Cell Physiol. 43 (1954) 271-281.
[3] R. D. Gietz, R. A. Woods, Transformation of yeast by lithium acetate/single-stranded carrier DNA/polyethylene glycol method, Methods Enzymol. 350 (2002) 87-96.
[4] U. Güldener, S. Heck, T. Fiedler, J. Beinhauer, J. H. Hegemann, A new efficient gene disruption cassette for repeated use in budding yeast, Nucleic Acids Res. 24 (1996) 2519-2524.
[5] U. Güldener, J. Heinisch, G. J. Koehler, D. Voss, J. H. Hegemann, A second set of loxP marker cassettes for Cre-mediated multiple gene knockouts in budding yeast, Nucleic Acids Research 30(6) (2002) e23.
[6] H. Van Urk, P. R. Mak, W. A. Scheffers, J. P. Van Dijken, Metabolic responses of *Saccharomyces cerevisiae* CBS 8066 and *Candida utilis* CBS 621 upon transition from glucose limitation to glucose excess, Yeast 4 (1988) 283-291.
[7] C. Verduyn, E. Postma, W. A. Scheffers, J. P. Van Dijken, Effect of benzoic acid on metabolic fluxes in yeasts: a continuous-culture study on the regulation of respiration and alcoholic fermentation, Yeast 8 (1992) 501-517.
[8] R. A. Weusthuis, W. Visser, J. T. Pronk, W. A. Scheffers, J. P. Van Dijken, Effects of oxygen limitation on sugar metabolism in yeasts—a continuous-culture study of the Kluyver effect, Microbiology 140 (1994) 703-715.
[9] S. C. Kou, et al. (1970). J. Bact. 102, 671-678.
[10] J. Becker et al. (2003). Appl. Environ. Microbiol. 69, 4144-4150.
[11] J. B. Thoden et al. (2005). J. Biol. Chem. 280, 36905-36911

The invention claimed is:

1. A yeast cell comprising
at least one exogenous gene of at least one pentose metabolic pathway non-native to the yeast cell,
wherein said yeast cell has a disruption of the hexokinase 1 (hxk1), hexokinase 2 (hxk2), glucokinase 1 (glk1), and galactokinase 1 (gal1) native in the yeast cell, and
wherein said yeast cell further comprising at least one of re-introduced hxk1, hxk2, glk1, and gal1 gene, in order to restore an ability of said yeast to consume glucose.

2. A process for preparing a pentose fermenting yeast cell, comprising
subjecting a yeast cell comprising at least one exogenous gene of pentose metabolic pathway to disruption of the gene hxk2 native in the yeast cell,
subjecting a resulting disruptant strain to evolutionary engineering to improve pentose consumption, until the yeast cell has growth rate of at least 0.05 h$^{-1}$ on the pentose as sole carbon source,
isolating the resulting pentose fermenting yeast cell, and
introducing in the resulting yeast, at least one of hxk1, hxk2, glk1, and gal1 gene, in order to restore an ability of said yeast to consume glucose.

3. A process, for preparing a pentose fermenting yeast cell, comprising
subjecting a yeast cell comprising at least one-exogenous gene of pentose metabolic pathway to disruption of the gene hxk2 native in the yeast cell, and
subjecting a resulting disruptant strain to evolutionary engineering to improve pentose consumption, until the yeast cell has growth rate of at least 0.05 h$^{-1}$ on the pentose as sole carbon source, and
isolating the resulting pentose fermenting yeast cell,
wherein in the disruptant strain is the yeast cell of claim 1.

4. A pentose and glucose fermenting *Saccharomyces* cell that is capable of anaerobic simultaneous pentose and glucose consumption, obtainable according to the process of claim 2.

5. A process for producing a fermentation product from the fermentation of pentose, comprising:
culturing the pentose and glucose fermenting yeast cell according to claim 4 in a pentose and glucose containing material under suitable fermentation conditions for a period of time sufficient to allow the fermentation of pentose and glucose to fermentation product, wherein said yeast cell ferments pentose to produce fermentation product at a higher level relative to a corresponding wild-type yeast.

6. The process according to claim 5, wherein the fermentation time is reduced relative to the corresponding fermentation of wild-type yeast.

7. The process according to claim 6, wherein the fermentation time is reduced at least 40% or more.

8. The process according to claim 5, wherein pentose and glucose are co-fermented.

9. The process according to claim 8, wherein overall fermentation rate is at least about 20%, optionally at least about 50% or optionally about 100% higher than that of a process with a corresponding wild-type yeast.

10. The process according to claim 5, wherein the pentose-containing material comprises a hydrolysate of lignocellulosic material.

11. The process according to claim 10, wherein the hydrolysate is an enzymatic hydrolysate of lignocellulosic material.

* * * * *

SEQUENCE LISTING

<160> NUMBER OF SEQ ID NOS: 58

<210> SEQ ID NO 1
<211> LENGTH: 62
<212> TYPE: DNA
<213> ORGANISM: Artificial Sequence
<220> FEATURE:
<223> OTHER INFORMATION: Synthetic DNA

<400> SEQUENCE: 1

```
gttgtaggaa tataattctc cacacataat aagtacgcta attcagctga agcttcgtac    60
gc                                                                  62
```

```
<210> SEQ ID NO 2
<211> LENGTH: 67
<212> TYPE: DNA
<213> ORGANISM: Artificial Sequence
<220> FEATURE:
<223> OTHER INFORMATION: Synthetic DNA

<400> SEQUENCE: 2
aaaagggcac cttcttgttg ttcaaactta atttacaaat taagtgcata ggccactagt     60
ggatctg                                                                67

<210> SEQ ID NO 3
<211> LENGTH: 63
<212> TYPE: DNA
<213> ORGANISM: Artificial Sequence
<220> FEATURE:
<223> OTHER INFORMATION: Synthetic DNA

<400> SEQUENCE: 3
tttcttttaa tcaaactcac ccaaacaact caattagaat actgcagctg aagcttcgta     60
cgc                                                                    63

<210> SEQ ID NO 4
<211> LENGTH: 69
<212> TYPE: DNA
<213> ORGANISM: Artificial Sequence
<220> FEATURE:
<223> OTHER INFORMATION: Synthetic DNA

<400> SEQUENCE: 4
gaataataat attaagggag ggaaaaacac atttatattt cattacagca taggccacta     60
gtggatctg                                                              69

<210> SEQ ID NO 5
<211> LENGTH: 64
<212> TYPE: DNA
<213> ORGANISM: Artificial Sequence
<220> FEATURE:
<223> OTHER INFORMATION: Synthetic DNA

<400> SEQUENCE: 5
ctcggacaaa ggtcttccta tgattccggc gttcgtcacc gggtccagct gaagcttcgt     60
acgc                                                                   64

<210> SEQ ID NO 6
<211> LENGTH: 64
<212> TYPE: DNA
<213> ORGANISM: Artificial Sequence
<220> FEATURE:
<223> OTHER INFORMATION: Synthetic DNA

<400> SEQUENCE: 6
taaaggagag aagatggtaa gtacggtggg atacgtacac aaacataggc cactagtgga     60
tctg                                                                   64

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
```

-continued cgcacgtcaa gactgtcaag                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
tcgtatgtga atgctggtcg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
ttcgccactg tcttatctac                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
ccgttcgttc cagaattatc                                              20

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA

<400> SEQUENCE: 11
ccttaggacc gttgagagga atag                                         24

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA

<400> SEQUENCE: 12
tcccggagaa caaagtaagt gg                                           22

<210> SEQ ID NO 13
<211> LENGTH: 25
<212> TYPE: DNA
<213> ORGANISM: Artificial Sequence
<220> FEATURE:
<223> OTHER INFORMATION: Synthetic DNA

<400> SEQUENCE: 13
aaaaacggga aataacaata acgac                                        25

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
tgcgatctta ttagtgtgtg acatt                                          25

<210> SEQ ID NO 15
<211> LENGTH: 1458
<212> TYPE: DNA
<213> ORGANISM: Saccharomyces cerevisiae S288C

<400> SEQUENCE: 15
atggttcatt taggtccaaa gaaaccacag gctagaaagg gttccatggc tgatgtgccc     60
aaggaattga tggatgaaat tcatcagttg gaagatatgt ttacagttga cagcgagacc    120
ttgagaaagg ttgttaagca ctttatcgac gaattgaata aaggtttgac aaagaaggga    180
ggtaacattc caatgattcc cggttgggtc atggaattcc caacaggtaa agaatctggt    240
aactatttgg ccattgattt gggtggtact aacttaagag tcgtgttggt caagttgagc    300
ggtaaccata cctttgacac cactcaatcc aagtataaac taccacatga catgagaacc    360
actaagcacc aagaggagtt atggtccttt attgccgact cttttgaagga ctttatggtc    420 gagcaagaat tgctaaacac caaggacacc ttaccattag gtttcacctt ctcgtaccca    480
gcttcccaaa acaagattaa cgaaggtatt ttgcaaagat ggaccaaggg tttcgatatt    540
ccaaatgtcg aaggccacga tgtcgtccca ttgctacaaa cgaaatttc caagagagag     600 ttgcctattg aaattgtagc attgattaat gatactgttg gtactttaat tgcctcatac    660
tacactgacc cagagactaa gatgggtgtg attttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc aagacctggt caacaagct    900 tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaagac tttgtgaatt gatcggtacc agagctgcta gattagctgt tgtggtatt   1200 gccgctattt gccaaaagag aggttacaag actggtcaca ttgccgctga cggttctgtc   1260
tataacaaat acccaggttt caaggaagcc gccgctaagg gttgagagaa tatctatgga   1320
tggactggtg acgcaagcaa agatccaatt acgattgttc cagctgagga tggttcaggt   1380
gcaggtgctg ctgttattgc tgcattgtcc gaaaaaagaa ttgccgaagg taagtctctt   1440
ggtatcattg gcgcttaa                                                 1458

<210> SEQ ID NO 16
<211> LENGTH: 1461
<212> TYPE: DNA
<213> ORGANISM: Saccharomyces cerevisiae S288C

<400> SEQUENCE: 16
atggttcatt taggtccaaa aaaaccacaa gccagaaagg gttccatggc cgatgtgcca     60
aaggaattga tgcaacaaat tgagaatttt gaaaaaattt tcactgttcc aactgaaact    120
ttacaagccg ttaccaagca cttcatttcc gaattggaaa agggtttgtc caagaagggt    180

```
ggtaacattc caatgattcc aggttgggtt atggatttcc caactggtaa ggaatccggt    240
gatttcttgg ccattgattt gggtggtacc aacttgagag ttgtcttagt caagttgggc    300
ggtgaccgta cctttgacac cactcaatct aagtacagat taccagatgc tatgagaact    360
actcaaaatc cagacgaatt gtgggaattt attgccgact cttgaaagc ttttattgat     420
```
*(line 420: gtgggaattt attgccgact cttgaaagc ttttattgat)*
```
gagcaattcc cacaaggtat ctctgagcca attccattgg gtttcacctt ttcttccca     480
gcttctcaaa acaaaatcaa tgaaggtatc ttgcaaagat ggactaaagg ttttgatatt    540
ccaaacattg aaaaccacga tgttgttcca atgttgcaaa agcaaatcac taagaggaat    600
atcccaattg aagttgttgc tttgataaac gacactaccg gtactttggt tgcttcttac    660
tacactgacc cagaaactaa gatgggtgtt atcttcggta ctggtgtcaa tggtgcttac   720
tacgatgttt gttccgatat cgaaaagcta caaggaaaac tatctgatga cattccacca    780
tctgctccaa tggccatcaa ctgtgaatac ggttccttcg ataatgaaca tgtcgttttg    840
ccaagaacta atacgatat caccattgat gaagaatctc caagaccagg ccaacaaacc     900
tttgaaaaaa tgtcttctgg ttactactta ggtgaaattt tgcgtttggc cttgatggac    960
atgtacaaac aaggtttcat cttcaagaac caagacttgt ctaagttcga caagcctttc   1020
gtcatggaca cttcttaccc agccagaatc gaggaagatc cattcgagaa cctagaagat   1080
accgatgact tgttccaaaa tgagttcggt atcaacacta ctgttcaaga acgtaaattg   1140
atcagacgtt tatctgaatt gattggtgct agagctgcta gattgtccgt ttgtggtatt   1200
gctgctatct gtcaaaagag aggttacaag accggtcaca tcgctgcaga cggttccgtt   1260
tacaacagat acccaggttt caaagaaaag gctgccaatg ctttgaagga catttacggc   1320
tggactcaaa cctcactaga cgactaccca atcaagattg ttcctgctga agatggttcc   1380
ggtgctggtg ccgctgttat tgctgctttg gcccaaaaaa gaattgctga aggtaagtcc   1440
gttggtatca tcggtgctta a                                             1461
```

<210> SEQ ID NO 17
<211> LENGTH: 1503
<212> TYPE: DNA
<213> ORGANISM: Saccharomyces cerevisiae S288C

<400> SEQUENCE: 17

```
atgtcattcg acgacttaca caaagccact gagagagcgg tcatccaggc cgtggaccag     60
atctgcgacg atttcgaggt tacccccgag aagctggacg aattaactgc ttacttcatc    120
gaacaaatgg aaaaaggtct agctccacca aaggaaggcc acacattggc ctcggacaaa    180
ggtcttccta tgattccggc gttcgtcacc gggtcaccca acgggacgga gcgcggtgtt    240
ttactagccg ccgacctggg tggtaccaat ttccgtatat gttctgttaa cttgcatgga    300
gatcatactt tctccatgga gcaaatgaag tccaagattc ccgatgattt gctagacgat    360
gagaacgtca catctgacga cctgtttggg tttctagcac gtcgtacact ggcctttatg    420
aagaagtatc acccggacga gttggccaag ggtaaagacg ccaagcccat gaaactgggg    480
ttcactttct cataccctgt agaccagacc tctctaaact ccgggacatt gatccgttgg    540
accagggtt tccgcatcgc ggacaccgtc ggaaaggatg tcgtgcaatt gtaccaggag    600
caattaagcg ctcagggtat gcctatgatc aaggttgttg cattaaccaa cgacaccgtc    660
ggaacgtacc tatcgcattg ctacacgtcc gataacacgg actcaatgac gtccggagaa    720
atctcggagc cggtcatcgg atgtatttc ggtaccggta ccaatgggtg ctatatggag    780
gagatcaaca agatcacgaa gttgccacag gagttgcgtg acaagttgat aaaggagggt    840
```

-continued

```
aagacacaca tgatcatcaa tgtcgaatgg gggtccttcg ataatgagct caagcacttg      900
cctactacta agtatgacgt cgtaattgac cagaaactgt caacgaaccc gggatttcac      960
ttgtttgaaa aacgtgtctc agggatgttc ttgggtgagg tgttgcgtaa cattttagtg     1020
gacttgcact cgcaaggctt gcttttgcaa cagtacaggt ccaaggaaca acttcctcgc     1080
cacttgacta cacctttcca gttgtcatcc gaagtgctgt cgcatattga aattgacgac     1140
tcgacaggtc tacgtgaaac agagttgtca ttattacaga gtctcagact gcccaccact     1200
ccaacagagc gtgttcaaat tcaaaaattg gtgcgcgcga tttctaggag atctgcgtat     1260
ttagccgccg tgccgcttgc cgcgatattg atcaagacaa atgctttgaa caagagatat     1320
catggtgaag tcgagatcgg ttgtgatggt tccgttgtgg aatactaccc cggtttcaga     1380
tctatgctga gacacgcctt agccttgtca cccttgggtg ccgagggtga gaggaaggtg     1440
cacttgaaga ttgccaagga tggttccgga gtgggtgccg ccttgtgtgc gcttgtagca     1500
tga                                                                   1503
```

<210> SEQ ID NO 18
<211> LENGTH: 1587
<212> TYPE: DNA
<213> ORGANISM: Saccharomyces cerevisiae S288C

<400> SEQUENCE: 18

```
atgactaaat ctcattcaga agaagtgatt gtacctgagt tcaattctag cgcaaaggaa       60
ttaccaagac cattggccga aaagtgcccg agcataatta agaaatttat aagcgcttat      120
gatgctaaac cggattttgt tgctagatcg cctggtagag tcaatctaat tggtgaacat      180
attgattatt gtgacttctc ggttttacct ttagctattg attttgatat gctttgcgcc      240
gtcaaagttt tgaacgagaa aaatccatcc attaccttaa taaatgctga tcccaaattt      300
gctcaaagga agttcgattt gccgttggac ggttcttatg tcacaattga tccttctgtg      360
tcggactggt ctaattactt taaatgtggt ctccatgttg ctcactcttt tctaaagaaa      420
cttgcaccgg aaaggtttgc cagtgctcct ctggccgggc tgcaagtctt ctgtgagggt      480
gatgtaccaa ctggcagtgg attgtcttct tcggccgcat tcatttgtgc cgttgcttta      540
gctgttgtta aagcgaatat gggccctggt tatcatatgt ccaagcaaaa tttaatgcgt      600
attacggtcg ttgcagaaca ttatgttggt gttaacaatg gcggtatgga tcaggctgcc      660
tctgtttgcg gtgaggaaga tcatgctcta tacgttgagt tcaaaccgca gttgaaggct      720
actccgttta aatttccgca attaaaaaac catgaaatta gctttgttat tgcgaacacc      780
cttgttgtat ctaacaagtt tgaaaccgcc ccaaccaact ataatttaag agtggtagaa      840
gtcactacag ctgcaaatgt tttagctgcc acgtacggtg ttgttttact ttctggaaaa      900
gaaggatcga gcacgaataa aggtaatcta agagatttca tgaacgttta ttatgccaga      960
tatcacaaca tttccacacc ctggaacggc atattgaat ccggcatcga acggttaaca     1020
aagatgctag tactagttga agagtctctc gccaataaga acagggctt tagtgttgac      1080 gatgtcgcac aatccttgaa ttgttctcgc gaagaattca aagagacta cttaacaaca      1140 tctccagtga gatttcaagt cttaaagcta tatcagaggg ctaagcatgt gtattctgaa      1200 tcttttaagag tcttgaaggc tgtgaaatta atgactacag cgagctttac tgccgacgaa     1260 gacttttttca agcaatttgg tgccttgatg aacgagtctc aagcttcttg cgataaactt     1320
tacgaatgtt cttgtccaga gattgacaaa atttgttcca ttgctttgtc aaatggatca     1380
```

| | |
|---|---|
| tatggttccc gtttgaccgg agctggctgg ggtggttgta ctgttcactt ggttccaggg | 1440 |
| ggcccaaatg caacataga aaaggtaaaa gaagcccttg ccaatgagtt ctacaaggtc | 1500 |
| aagtacccta agatcactga tgctgagcta gaaaatgcta tcatcgtctc taaaccagca | 1560 |
| ttgggcagct gtctatatga attataa | 1587 |

<210> SEQ ID NO 19
<211> LENGTH: 1503
<212> TYPE: DNA
<213> ORGANISM: Saccharomyces cerevisiae S288C

<400> SEQUENCE: 19

| | |
|---|---|
| atgtcatttg aaaatttaca taaagtcaat gctgaggcat ggaagatgc agtggttgag | 60 |
| atctgctcct cattgcaggt tgatgcagca aagttggacg aactaacagc gtacttcatt | 120 |
| gaatgtatgg aaaaggggtt gaataacacc tctgtaggcg aagaaaagac ggtggacaag | 180 |
| ggtctaccca tgatccctac atatgtaacc agtttgccca atgggacgga acgtggtgtt | 240 |
| ttgctggctg cagatttagg tgggactcac ttcagagtgt gttctgtgac tttgaatggt | 300 |
| gacggaacct tgatatgca gcaattgaag tctaagattc cggaagaata tctaaatgac | 360 |
| aaggatgtca ccagcgagga gctgtttagc tacctgggtc gccgtacaag ggccttcgtt | 420 |
| aggaagcatc atcctgagtt gttgaagtcc acggggagaa acataaaacc tttgaaaatg | 480 |
| ggatttacct tctcatatcc cgttgaccaa acctctttga gttccggtac tttaatcaga | 540 |
| tggaccaaaa gcttcaagat tgaagacacg gtcggcaagg atgtcgtgag gttataccag | 600 |
| gagcaattag acattcaggg gctctctatg attaatgtgg tagctttgac caacgacacg | 660 |
| gttggcactt tcctatccca ctgctacact tcaggctctc gtccatcgag tgctggtgag | 720 |
| attagcgagc ctgtcattgg ttgtatcttt ggtactggta ctaacggttg ctatatggag | 780 |
| gatattgaaa acatcaagaa gctaccagat gagctcagaa caagactgct gcatgaagga | 840 |
| aaaacccaaa tgtgcatcaa catcgaatgg ggttcttttcg acaatgaatt gaaacatttg | 900 |
| tctgctacaa agtatgacat cgatattgac caaaaatttt ctccaaatcc aggttaccat | 960 |
| ctatttgaaa aaagaattttc cggcatgtac ttgggtgagc tgttaaggaa catcctggtg | 1020 |
| gacttgcatg caaggggctt aatcttggga cagtatcgta attacgatca attacctcac | 1080 |
| cgtttaaaga ctccttttcca attgtgcagt gaagttcttt ccaggattga aatcgatgat | 1140 |
| tcgacaaact gcgtgaaaac tgaattgtcg tttttgcaga gtttgaggct accgaccact | 1200 |
| tttgaagaac gtaaagcaat tcaaaatctg gtccgttcca ttacgagaag gtctgcatat | 1260 |
| ctagcagccg ttccgattgc cgccatccta atcaagacaa acgctttgaa caaaagatat | 1320 |
| cacggtgagg tagaaattgg ttttgacggt tatgtcatcg aatactatcc tggattcaga | 1380 |
| tccatgctga gacatgcttt ggcattaagt ccaattggca ctgagggtga acgtaagata | 1440 |
| catttgcgtc tagccaaaga tgggtccggt gttggcgcag ctttgtgtgc tctggtggca | 1500 |
| taa | 1503 |

<210> SEQ ID NO 20
<211> LENGTH: 1302
<212> TYPE: DNA
<213> ORGANISM: Saccharomyces cerevisiae S288C

<400> SEQUENCE: 20

| | |
|---|---|
| atgacaattg aaagcactct agctcgggaa ttagaaaagct tgattttacc cgctgattcc | 60 |
| atagtgaatg tagttgacca attccaagag gagttgttat cacggcttca gacaaatacg | 120 |

-continued

```
atttctatgc tcccgcagtg tttagtccca gataaacgat cgcgatggaa ccctgaagac    180
aaaattctga ccattgattt cggcgggaca agactgaaat tgcaattat ctctctgccc     240 caaatcgtta tcgaatacaa tgatgccttc gaacttacct acaacatcgt tgattcgaat    300
ttctttaatc aaatcatcta tacaatatgt accaggctgg ctgcaaatgg ttatataaaa    360
aaaaagaacg agtcatctga ggcgtctaaa ttttttgttt ccgtgacatt cagttttcct    420
ctaaatccag aagggaggt agttgcaatg ggaaaaggat tgtgatgac tgacacccttt     480 caaggatcca cggtgaaaca gctcatccaa tcttcctttc accggattat atcagaaaat    540
atcgaagaat ttttctgtac catgaacgtg tgtcatgtaa taaacgatgc aattgcagtt    600
tcactaacaa gcaaatttat atgcgaaaac gattccatct cattaataat aggaactggt    660
acaaatgcat gttttgaggt tccatacgga tatttaccac ctttcaagag agatgccctg    720
agagaaacat taccgtcaag ctataataag gagacattaa atttcaaaca tgttctcatt    780
aattctgaaa ttggctttat tggtaaaaat gtcattgcat tgcaaccgtt tgacattcat    840
ggagcaatct catacgaaat gccactagag tgcgttactt ctggtaaatg gcttccccta    900
tcattaaaaa atattctatt gcaatataac ataatcccca aaacttccc agtagagttc      960 aatggggaac tggtatgcca gctggcagaa gactgtacta atgcttggtt cgaaaacgaa    1020
cattatgcac taatttgtca gatcgcacga ctattaatca agagagccgc atttatgtt     1080 gctgcaattg tacaagctat tgatatcatc acaggctgca aaaactataa ctttattcat    1140
attggctacg ttggatcctt tctccacaat tcaaattttt atcgagagca gataaaatat    1200
tactccagca tacatattaa gttgcaattc ttaaatcaca gtaatcttct aggcgctgca    1260
atagccacct acttgaacaa atcagacaac caagttcaat aa                       1302
```

<210> SEQ ID NO 21
<211> LENGTH: 485
<212> TYPE: PRT
<213> ORGANISM: Saccharomyces cerevisiae S288C

<400> SEQUENCE: 21

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
                20                  25                  30

Met Phe Thr Val Asp Ser Glu Thr Leu Arg Lys Val Val Lys His Phe
            35                  40                  45

Ile Asp Glu Leu Asn Lys Gly Leu Thr Lys Lys Gly Gly Asn Ile Pro
        50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160
```

```
Ala Ser Gln Asn Lys Ile Asn Glu Gly Ile Leu Gln Arg Trp Thr Lys
            165                 170                 175
Gly Phe Asp Ile Pro Asn Val Glu Gly His Asp Val Val Pro Leu Leu
        180                 185                 190
Gln Asn Glu Ile Ser Lys Arg Glu Leu Pro Ile Glu Ile Val Ala Leu
    195                 200                 205
Ile Asn Asp Thr Val Gly Thr Leu Ile Ala Ser Tyr Tyr Thr Asp Pro
210                 215                 220
Glu Thr Lys Met Gly Val Ile Phe Gly Thr Gly Val Asn Gly Ala Phe
225                 230                 235                 240
Tyr Asp Val Val Ser Asp Ile Glu Lys Leu Glu Gly Lys Leu Ala Asp
                245                 250                 255
Asp Ile Pro Ser Asn Ser Pro Met Ala Ile Asn Cys Glu Tyr Gly Ser
            260                 265                 270
Phe Asp Asn Glu His Leu Val Leu Pro Arg Thr Lys Tyr Asp Val Ala
        275                 280                 285
Val Asp Glu Gln Ser Pro Arg Pro Gly Gln Gln Ala Phe Glu Lys Met
    290                 295                 300
Thr Ser Gly Tyr Tyr Leu Gly Glu Leu Leu Arg Leu Val Leu Leu Glu
305                 310                 315                 320
Leu Asn Glu Lys Gly Leu Met Leu Lys Asp Gln Asp Leu Ser Lys Leu
                325                 330                 335
Lys Gln Pro Tyr Ile Met Asp Thr Ser Tyr Pro Ala Arg Ile Glu Asp
            340                 345                 350
Asp Pro Phe Glu Asn Leu Glu Asp Thr Asp Asp Ile Phe Gln Lys Asp
        355                 360                 365
Phe Gly Val Lys Thr Thr Leu Pro Glu Arg Lys Leu Ile Arg Arg Leu
    370                 375                 380
Cys Glu Leu Ile Gly Thr Arg Ala Ala Arg Leu Ala Val Cys Gly Ile
385                 390                 395                 400
Ala Ala Ile Cys Gln Lys Arg Gly Tyr Lys Thr Gly His Ile Ala Ala
                405                 410                 415
Asp Gly Ser Val Tyr Asn Lys Tyr Pro Gly Phe Lys Glu Ala Ala Ala
            420                 425                 430
Lys Gly Leu Arg Asp Ile Tyr Gly Trp Thr Gly Asp Ala Ser Lys Asp
        435                 440                 445
Pro Ile Thr Ile Val Pro Ala Glu Asp Gly Ser Gly Ala Gly Ala Ala
    450                 455                 460
Val Ile Ala Ala Leu Ser Glu Lys Arg Ile Ala Glu Gly Lys Ser Leu
465                 470                 475                 480
Gly Ile Ile Gly Ala
                485

<210> SEQ ID NO 22
<211> LENGTH: 486
<212> TYPE: PRT
<213> ORGANISM: Saccharomyces cerevisiae S288C

<400> SEQUENCE: 22

Met Val His Leu Gly Pro Lys Lys Pro Gln Ala Arg Lys Gly Ser Met
1               5                   10                  15
Ala Asp Val Pro Lys Glu Leu Met Gln Gln Ile Glu Asn Phe Glu Lys
            20                  25                  30
Ile Phe Thr Val Pro Thr Glu Thr Leu Gln Ala Val Thr Lys His Phe
        35                  40                  45
```

```
Ile Ser Glu Leu Glu Lys Gly Leu Ser Lys Gly Gly Asn Ile Pro
     50                  55                  60

Met Ile Pro Gly Trp Val Met Asp Phe Pro Thr Gly Lys Glu Ser Gly
 65                  70                  75                  80

Asp Phe Leu Ala Ile Asp Leu Gly Gly Thr Asn Leu Arg Val Val Leu
                     85                  90                  95

Val Lys Leu Gly Gly Asp Arg Thr Phe Asp Thr Thr Gln Ser Lys Tyr
                100                 105                 110

Arg Leu Pro Asp Ala Met Arg Thr Thr Gln Asn Pro Asp Glu Leu Trp
            115                 120                 125

Glu Phe Ile Ala Asp Ser Leu Lys Ala Phe Ile Asp Glu Gln Phe Pro
        130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Leu Phe Gln Asn Glu
        355                 360                 365

Phe Gly Ile Asn Thr Thr Val Gln Glu Arg Lys Leu Ile Arg Arg Leu
370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
        435                 440                 445

Tyr Pro Ile Lys Ile Val Pro Ala Glu Asp Gly Ser Gly Ala Gly Ala
            450                 455                 460
```

```
Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 23
<211> LENGTH: 500
<212> TYPE: PRT
<213> ORGANISM: Saccharomyces cerevisiae S288C

<400> SEQUENCE: 23

Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
            20                  25                  30

Asp Glu Leu Thr Ala Tyr Phe Ile Glu Gln Met Glu Lys Gly Leu Ala
        35                  40                  45

Pro Pro Lys Glu Gly His Thr Leu Ala Ser Asp Lys Gly Leu Pro Met
    50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Thr Asn Phe Arg Ile Cys Ser Val
                85                  90                  95

Asn Leu His Gly Asp His Thr Phe Ser Met Glu Gln Met Lys Ser Lys
            100                 105                 110

Ile Pro Asp Asp Leu Leu Asp Asp Glu Asn Val Thr Ser Asp Asp Leu
        115                 120                 125

Phe Gly Phe Leu Ala Arg Arg Thr Leu Ala Phe Met Lys Lys Tyr His
    130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190

Asp Val Val Gln Leu Tyr Gln Glu Gln Leu Ser Ala Gln Gly Met Pro
        195                 200                 205

Met Ile Lys Val Val Ala Leu Thr Asn Asp Thr Val Gly Thr Tyr Leu
    210                 215                 220

Ser His Cys Tyr Thr Ser Asp Asn Thr Asp Ser Met Thr Ser Gly Glu
225                 230                 235                 240

Ile Ser Glu Pro Val Ile Gly Cys Ile Phe Gly Thr Gly Thr Asn Gly
                245                 250                 255

Cys Tyr Met Glu Glu Ile Asn Lys Ile Thr Lys Leu Pro Gln Glu Leu
            260                 265                 270

Arg Asp Lys Leu Ile Lys Glu Gly Lys Thr His Met Ile Ile Asn Val
        275                 280                 285

Glu Trp Gly Ser Phe Asp Asn Glu Leu Lys His Leu Pro Thr Thr Lys
    290                 295                 300

Tyr Asp Val Val Ile Asp Gln Lys Leu Ser Thr Asn Pro Gly Phe His
305                 310                 315                 320

Leu Phe Glu Lys Arg Val Ser Gly Met Phe Leu Gly Glu Val Leu Arg
                325                 330                 335

Asn Ile Leu Val Asp Leu His Ser Gln Gly Leu Leu Leu Gln Gln Tyr
            340                 345                 350
```

```
Arg Ser Lys Glu Gln Leu Pro Arg His Leu Thr Thr Pro Phe Gln Leu
        355                 360                 365

Ser Ser Glu Val Leu Ser His Ile Glu Ile Asp Asp Ser Thr Gly Leu
        370                 375                 380

Arg Glu Thr Glu Leu Ser Leu Leu Gln Ser Leu Arg Leu Pro Thr Thr
385                 390                 395                 400

Pro Thr Glu Arg Val Gln Ile Gln Lys Leu Val Arg Ala Ile Ser Arg
                405                 410                 415

Arg Ser Ala Tyr Leu Ala Ala Val Pro Leu Ala Ala Ile Leu Ile Lys
                420                 425                 430

Thr Asn Ala Leu Asn Lys Arg Tyr His Gly Glu Val Glu Ile Gly Cys
                435                 440                 445

Asp Gly Ser Val Val Glu Tyr Tyr Pro Gly Phe Arg Ser Met Leu Arg
            450                 455                 460

His Ala Leu Ala Leu Ser Pro Leu Gly Ala Glu Gly Glu Arg Lys Val
465                 470                 475                 480

His Leu Lys Ile Ala Lys Asp Gly Ser Gly Val Gly Ala Ala Leu Cys
                485                 490                 495

Ala Leu Val Ala
            500

<210> SEQ ID NO 24
<211> LENGTH: 528
<212> TYPE: PRT
<213> ORGANISM: Saccharomyces cerevisiae S288C

<400> SEQUENCE: 24

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
                20                  25                  30

Ile Lys Lys Phe Ile Ser Ala Tyr Asp Ala Lys Pro Asp Phe Val Ala
            35                  40                  45

Arg Ser Pro Gly Arg Val Asn Leu Ile Gly Glu His Ile Asp Tyr Cys
        50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
                100                 105                 110

Tyr Val Thr Ile Asp Pro Ser Val Ser Asp Trp Ser Asn Tyr Phe Lys
            115                 120                 125

Cys Gly Leu His Val Ala His Ser Phe Leu Lys Lys Leu Ala Pro Glu
        130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ser Ala Ala Phe Ile Cys
                165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
        195                 200                 205

Val Gly Val Asn Asn Gly Gly Met Asp Gln Ala Ala Ser Val Cys Gly
```

-continued

```
            210                 215                 220
Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
                260                 265                 270

Asn Tyr Asn Leu Arg Val Val Glu Val Thr Ala Ala Asn Val Leu
            275                 280                 285

Ala Ala Thr Tyr Gly Val Val Leu Leu Ser Gly Lys Glu Gly Ser Ser
290                 295                 300

Thr Asn Lys Gly Asn Leu Arg Asp Phe Met Asn Val Tyr Ala Arg
305                 310                 315                 320

Tyr His Asn Ile Ser Thr Pro Trp Asn Gly Asp Ile Glu Ser Gly Ile
                325                 330                 335

Glu Arg Leu Thr Lys Met Leu Val Leu Val Glu Glu Ser Leu Ala Asn
                340                 345                 350

Lys Lys Gln Gly Phe Ser Val Asp Asp Val Ala Gln Ser Leu Asn Cys
            355                 360                 365

Ser Arg Glu Glu Phe Thr Arg Asp Tyr Leu Thr Thr Ser Pro Val Arg
370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Ala Ser Phe
                405                 410                 415

Thr Ala Asp Glu Asp Phe Phe Lys Gln Phe Gly Ala Leu Met Asn Glu
                420                 425                 430

Ser Gln Ala Ser Cys Asp Lys Leu Tyr Glu Cys Ser Cys Pro Glu Ile
            435                 440                 445

Asp Lys Ile Cys Ser Ile Ala Leu Ser Asn Gly Ser Tyr Gly Ser Arg
450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
            515                 520                 525

<210> SEQ ID NO 25
<211> LENGTH: 500
<212> TYPE: PRT
<213> ORGANISM: Saccharomyces cerevisiae S288C

<400> SEQUENCE: 25

Met Ser Phe Glu Asn Leu His Lys Val Asn Ala Glu Ala Leu Glu Asp
1               5                   10                  15

Ala Val Val Glu Ile Cys Ser Ser Leu Gln Val Asp Ala Ala Lys Leu
                20                  25                  30

Asp Glu Leu Thr Ala Tyr Phe Ile Glu Cys Met Glu Lys Gly Leu Asn
            35                  40                  45

Asn Thr Ser Val Gly Glu Glu Lys Thr Val Asp Lys Gly Leu Pro Met
50                  55                  60
```

```
Ile Pro Thr Tyr Val Thr Ser Leu Pro Asn Thr Glu Arg Gly Val
 65                  70                  75                  80

Leu Leu Ala Ala Asp Leu Gly Gly Thr His Phe Arg Val Cys Ser Val
                 85                  90                  95

Thr Leu Asn Gly Asp Gly Thr Phe Asp Met Gln Gln Leu Lys Ser Lys
                100                 105                 110

Ile Pro Glu Glu Tyr Leu Asn Asp Lys Asp Val Thr Ser Glu Glu Leu
                115                 120                 125

Phe Ser Tyr Leu Gly Arg Arg Thr Arg Ala Phe Val Arg Lys His His
            130                 135                 140

Pro Glu Leu Leu Lys Ser Thr Gly Glu Asn Ile Lys Pro Leu Lys Met
145                 150                 155                 160

Gly Phe Thr Phe Ser Tyr Pro Val Asp Gln Thr Ser Leu Ser Ser Gly
                    165                 170                 175

Thr Leu Ile Arg Trp Thr Lys Ser Phe Lys Ile Glu Asp Thr Val Gly
                180                 185                 190

Lys Asp Val Val Arg Leu Tyr Gln Glu Gln Leu Asp Ile Gln Gly Leu
            195                 200                 205

Ser Met Ile Asn Val Val Ala Leu Thr Asn Asp Thr Val Gly Thr Phe
210                 215                 220

Leu Ser His Cys Tyr Thr Ser Gly Ser Arg Pro Ser Ser Ala Gly Glu
225                 230                 235                 240

Ile Ser Glu Pro Val Ile Gly Cys Ile Phe Gly Thr Gly Thr Asn Gly
                    245                 250                 255

Cys Tyr Met Glu Asp Ile Glu Asn Ile Lys Lys Leu Pro Asp Glu Leu
                260                 265                 270

Arg Thr Arg Leu Leu His Glu Gly Lys Thr Gln Met Cys Ile Asn Ile
            275                 280                 285

Glu Trp Gly Ser Phe Asp Asn Glu Leu Lys His Leu Ser Ala Thr Lys
290                 295                 300

Tyr Asp Ile Asp Ile Asp Gln Lys Phe Ser Pro Asn Pro Gly Tyr His
305                 310                 315                 320

Leu Phe Glu Lys Arg Ile Ser Gly Met Tyr Leu Gly Glu Leu Leu Arg
                    325                 330                 335

Asn Ile Leu Val Asp Leu His Ala Arg Gly Leu Ile Leu Gly Gln Tyr
                340                 345                 350

Arg Asn Tyr Asp Gln Leu Pro His Arg Leu Lys Thr Pro Phe Gln Leu
            355                 360                 365

Cys Ser Glu Val Leu Ser Arg Ile Glu Ile Asp Ser Thr Asn Leu
370                 375                 380

Arg Glu Thr Glu Leu Ser Phe Leu Gln Ser Leu Arg Leu Pro Thr Thr
385                 390                 395                 400

Phe Glu Glu Arg Lys Ala Ile Gln Asn Leu Val Arg Ser Ile Thr Arg
                    405                 410                 415

Arg Ser Ala Tyr Leu Ala Ala Val Pro Ile Ala Ala Ile Leu Ile Lys
                420                 425                 430

Thr Asn Ala Leu Asn Lys Arg Tyr His Gly Glu Val Glu Ile Gly Phe
            435                 440                 445

Asp Gly Tyr Val Ile Glu Tyr Tyr Pro Gly Phe Arg Ser Met Leu Arg
450                 455                 460

His Ala Leu Ala Leu Ser Pro Ile Gly Thr Glu Gly Glu Arg Lys Ile
465                 470                 475                 480

His Leu Arg Leu Ala Lys Asp Gly Ser Gly Val Gly Ala Ala Leu Cys
```

```
                  485              490              495
Ala Leu Val Ala
            500

<210> SEQ ID NO 26
<211> LENGTH: 433
<212> TYPE: PRT
<213> ORGANISM: Saccharomyces cerevisiae S288C

<400> SEQUENCE: 26

Met Thr Ile Glu Ser Thr Leu Ala Arg Glu Leu Glu Ser Leu Ile Leu
1               5                   10                  15

Pro Ala Asp Ser Ile Val Asn Val Val Asp Gln Phe Gln Glu Glu Leu
            20                  25                  30

Leu Ser Arg Leu Gln Thr Asn Thr Ile Ser Met Leu Pro Gln Cys Leu
        35                  40                  45

Val Pro Asp Lys Arg Ser Arg Trp Asn Pro Glu Asp Lys Ile Leu Thr
    50                  55                  60

Ile Asp Phe Gly Gly Thr Arg Leu Lys Phe Ala Ile Ile Ser Leu Pro
65                  70                  75                  80

Gln Ile Val Ile Glu Tyr Asn Asp Ala Phe Glu Leu Thr Tyr Asn Ile
                85                  90                  95

Val Asp Ser Asn Phe Phe Asn Gln Ile Ile Tyr Thr Ile Cys Thr Arg
            100                 105                 110

Leu Ala Ala Asn Gly Tyr Ile Lys Lys Lys Asn Glu Ser Ser Glu Ala
        115                 120                 125

Ser Lys Phe Phe Val Ser Val Thr Phe Ser Phe Pro Leu Asn Pro Glu
    130                 135                 140

Gly Glu Val Val Ala Met Gly Lys Gly Phe Val Met Thr Asp Thr Leu
145                 150                 155                 160

Gln Gly Ser Thr Val Lys Gln Leu Ile Gln Ser Ser Phe His Arg Ile
                165                 170                 175

Ile Ser Glu Asn Ile Glu Glu Phe Phe Cys Thr Met Asn Val Cys His
            180                 185                 190

Val Ile Asn Asp Ala Ile Ala Val Ser Leu Thr Ser Lys Phe Ile Cys
        195                 200                 205

Glu Asn Asp Ser Ile Ser Leu Ile Ile Gly Thr Gly Thr Asn Ala Cys
    210                 215                 220

Phe Glu Val Pro Tyr Gly Tyr Leu Pro Pro Phe Lys Arg Asp Ala Leu
225                 230                 235                 240

Arg Glu Thr Leu Pro Ser Ser Tyr Asn Lys Glu Thr Leu Asn Phe Lys
                245                 250                 255

His Val Leu Ile Asn Ser Glu Ile Gly Phe Ile Gly Lys Asn Val Ile
            260                 265                 270

Ala Leu Gln Pro Phe Asp Ile His Gly Ala Ile Ser Tyr Glu Met Pro
        275                 280                 285

Leu Glu Cys Val Thr Ser Gly Lys Trp Leu Pro Leu Ser Leu Lys Asn
    290                 295                 300

Ile Leu Leu Gln Tyr Asn Ile Ile Pro Lys Asn Phe Pro Val Glu Phe
305                 310                 315                 320

Asn Gly Glu Leu Val Cys Gln Leu Ala Glu Asp Cys Thr Asn Ala Trp
                325                 330                 335

Phe Glu Asn Glu His Tyr Ala Leu Ile Cys Gln Ile Ala Arg Leu Leu
            340                 345                 350
```

```
Ile Lys Arg Ala Ala Phe Tyr Val Ala Ala Ile Val Gln Ala Ile Asp
        355                 360                 365
Ile Ile Thr Gly Cys Lys Asn Tyr Asn Phe Ile His Ile Gly Tyr Val
    370                 375                 380
Gly Ser Phe Leu His Asn Ser Asn Phe Tyr Arg Glu Gln Ile Lys Tyr
385                 390                 395                 400
Tyr Ser Ser Ile His Ile Lys Leu Gln Phe Leu Asn His Ser Asn Leu
                405                 410                 415
Leu Gly Ala Ala Ile Ala Thr Tyr Leu Asn Lys Ser Asp Asn Gln Val
            420                 425                 430
Gln
```

<210> SEQ ID NO 27
<211> LENGTH: 64
<212> TYPE: DNA
<213> ORGANISM: Artificial Sequence
<220> FEATURE:
<223> OTHER INFORMATION: Synthetic DNA

<400> SEQUENCE: 27
taatatacct ctatacttta acgtcaagga gaaaaaacta taatgcagct gaagcttcgt    60
acgc                                                                 64

<210> SEQ ID NO 28
<211> LENGTH: 66
<212> TYPE: DNA
<213> ORGANISM: Artificial Sequence
<220> FEATURE:
<223> OTHER INFORMATION: Synthetic DNA

<400> SEQUENCE: 28
aatgagaagt tgttctgaac aaagtaaaaa aaagaagtat acttacatag gccactagtg    60
gatctg                                                               66

<210> SEQ ID NO 29
<211> LENGTH: 25
<212> TYPE: DNA
<213> ORGANISM: Artificial Sequence
<220> FEATURE:
<223> OTHER INFORMATION: Synthetic DNA

<400> SEQUENCE: 29
atggcattat actcctgcta gaaag                                          25

<210> SEQ ID NO 30
<211> LENGTH: 24
<212> TYPE: DNA
<213> ORGANISM: Artificial Sequence
<220> FEATURE:
<223> OTHER INFORMATION: Synthetic DNA

<400> SEQUENCE: 30
aaaggatggc agagcatgtt atcg                                           24

<210> SEQ ID NO 31
<211> LENGTH: 24
<212> TYPE: DNA
<213> ORGANISM: Artificial Sequence
<220> FEATURE:
<223> OTHER INFORMATION: Synthetic DNA

<400> SEQUENCE: 31
gattgcgaga tccacgaaat tacc					24

<210> SEQ ID NO 32
<211> LENGTH: 24
<212> TYPE: DNA
<213> ORGANISM: Artificial Sequence
<220> FEATURE:
<223> OTHER INFORMATION: Synthetic DNA

<400> SEQUENCE: 32
aatcaccgga ttccttacca gttg					24

<210> SEQ ID NO 33
<211> LENGTH: 25
<212> TYPE: DNA
<213> ORGANISM: Artificial Sequence
<220> FEATURE:
<223> OTHER INFORMATION: Synthetic DNA

<400> SEQUENCE: 33
gaaattcacg ggatttattc gtgac					25

<210> SEQ ID NO 34
<211> LENGTH: 25
<212> TYPE: DNA
<213> ORGANISM: Artificial Sequence
<220> FEATURE:
<223> OTHER INFORMATION: Synthetic DNA

<400> SEQUENCE: 34
tttccatgtt tctaagcgta gtgag					25

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA

<400> SEQUENCE: 35
cccgtttgtt ggaagatagc					20

<210> SEQ ID NO 36
<211> LENGTH: 18
<212> TYPE: DNA
<213> ORGANISM: Artificial Sequence
<220> FEATURE:
<223> OTHER INFORMATION: Synthetic DNA

<400> SEQUENCE: 36
cacatcagcc atggaacc					18

<210> SEQ ID NO 37
<211> LENGTH: 19
<212> TYPE: DNA
<213> ORGANISM: Artificial Sequence
<220> FEATURE:
<223> OTHER INFORMATION: Synthetic DNA

<400> SEQUENCE: 37
gcaggtgctg ctgttattg					19

<210> SEQ ID NO 38
<211> LENGTH: 21
<212> TYPE: DNA
<213> ORGANISM: Artificial Sequence
<220> FEATURE:
<223> OTHER INFORMATION: Synthetic DNA

<400> SEQUENCE: 38
ccgagctatc ctacgacttt c                                                21

<210> SEQ ID NO 39
<211> LENGTH: 23
<212> TYPE: DNA
<213> ORGANISM: Artificial Sequence
<220> FEATURE:
<223> OTHER INFORMATION: Synthetic DNA

<400> SEQUENCE: 39
gcccgacagg gtaacatatt atc                                              23

<210> SEQ ID NO 40
<211> LENGTH: 23
<212> TYPE: DNA
<213> ORGANISM: Artificial Sequence
<220> FEATURE:
<223> OTHER INFORMATION: Synthetic DNA

<400> SEQUENCE: 40
ccggaatcat aggaagacct ttg                                              23

<210> SEQ ID NO 41
<211> LENGTH: 24
<212> TYPE: DNA
<213> ORGANISM: Artificial Sequence
<220> FEATURE:
<223> OTHER INFORMATION: Synthetic DNA

<400> SEQUENCE: 41
agaggaaggt gcacttgaag attg                                             24

<210> SEQ ID NO 42
<211> LENGTH: 24
<212> TYPE: DNA
<213> ORGANISM: Artificial Sequence
<220> FEATURE:
<223> OTHER INFORMATION: Synthetic DNA

<400> SEQUENCE: 42
ataagatgga attggccggt cttg                                             24

<210> SEQ ID NO 43
<211> LENGTH: 1587
<212> TYPE: DNA
<213> ORGANISM: Saccharomyces cerevisiae CEN.PK 113-7D

<400> SEQUENCE: 43
atgactaaat ctcattcaga agaagtgatt gtacctgagt tcaattctag cgcaaaggaa      60
ttaccaagac cattggccga aaagtgcccg agcataatta agaaatttat aagcgcttat     120
gatgctaaac cggattttgt tgctagatcg cctggtagag tcaatctaat tggtgaacat     180
attgattatt gtgacttctc ggttttacct ttagctattg attttgatat gctttgcgcc     240
gtcaaagttt tgaacgagaa aaatccatcc attaccttaa taaatgctga tcccaaattt     300
gctcaaagga agttcgattt gccgttggac ggttcttatg tcacaattga tccttctgtg     360
tcagactggt ctaattactt taaatgtggt ctccatgttg ctcactcttt tctaaagaaa     420
cttgcaccgg aaaggtttgc cagtgctcct ctggccgggc tgcaagtctt ctgtgagggt     480

```
gatgtaccaa ctggcagtgg attgtcttct tcggccgcat tcatttgtgc cgttgcttta      540
gctgttgtta aagcgaatat gggccctggt tatcatatgt ccaagcaaaa tttaatgcgt      600
atcacggtcg ttgcagaaca ttatgttggt gttaacaatg gcggtatgga tcaggctgcc      660
tctgtttgcg gtgaggaaga tcatgctcta tacgttgagt tcaaaccgca gttgaaggct      720
actccgttta aatttccgca attaaaaaac catgaaatta gctttgttat tgcgaacacc      780
cttgttgtat ctaacaagtt tgaaaccgcc ccaaccaact ataatttaag agtggtagaa      840
gtcactacag ctgcaaatgt tttagctgcc acgtacggtg ttgttttacc ttctggaaaa      900
gaaggatcga gcacgaataa aggtaatcta agagatttca tgaacgttta ttatgccaga      960
tatcacaaca tttccacacc ctggaacggc gatattgaat ccggcatcga acggttaaca     1020
aagatgctag tactagttga agagtctctc gccaataaga aacagggctt tagtgttgac     1080
gatgtcgcgc aatccttgaa ttgttctcgc gaagaattca caagagacta cttaacaaca     1140
tctccagtga gatttcaagt cttaaagcta tcagagggg ctaagcatgt gtattctgaa     1200
tctttaagag tcttgaaggc tgtgaaatta atgactacag agagctttac tgccgatgaa     1260
gacttttcca gcaatttggt gccttgatg aacgagtctc aagcttcttg cgataaactt     1320
tacgaatgtt cttgtccaga gattgacaaa atttgttcca ttgctttgtc aaatggatca     1380
tatggttccc gtttgaccgg agctggctgg ggtggttgta ctgttcactt ggttccaggg     1440
ggcccaaatg gcaacataga aaggtaaaa gaagcccttg ccaatgagtt ctacaaggtc      1500
aagtacccta agatcactga tgctgagctt gaaaatgcta ttatcgtctc taaaccagca     1560
ttgggcagct gtctatatga attataa                                         1587

<210> SEQ ID NO 44
<211> LENGTH: 1587
<212> TYPE: DNA
<213> ORGANISM: Saccharomyces cerevisiae IMK318

<400> SEQUENCE: 44
atgactaaat ctcattcaga agaagtgatt gtacctgagt tcaattctag cgcaaaggaa       60
ttaccaagac cattggccga aaagtgcccg agcataatta agaaatttat aagcgcttat      120
gatgctaaac cggattttgt tgctagatcg cctggtagag tcaatctaat tggtgaacat      180
attgattatt gtgacttctc ggttttacct ttagctattg attttgatat gctttgcgcc      240
gtcaaagttt tgaacgagaa aaatccatcc attaccttaa taaatgctga tcccaaattt      300
gctcaaagga agttcgattt gccgttggac ggttcttatg tcacaattga tccttctgtg      360
tcagactggt ctaattactt taaatgtggt ctccatgttg ctcactcttt tctaaagaaa      420
cttgcaccgg aaaggtttgc cagtgctcct ctggccgggc tgcaagtctt ctgtgagggt      480
gatgtaccaa ctggcagtgg attgtcttct tcggccgcat tcatttgtgc cgttgcttta      540
gctgttgtta aagcgaatat gggccctggt tatcatatgt ccaagcaaaa tttaatgcgt      600
atcacggtcg ttgcagaaca ttatgttggt gttaacaatg gcggtatgga tcaggctgcc      660
tctgtttgcg gtgaggaaga tcatgctcta tacgttgagt tcaaaccgca gttgaaggct      720
actccgttta aatttccgca attaaaaaac catgaaatta gctttgttat tgcgaacacc      780
cttgttgtat ctaacaagtt tgaaaccgcc ccaaccaact ataatttaag agtggtagaa      840
gtcactacag ctgcaaatgt tttagctgcc acgtacggtg ttgttttacc ttctggaaaa      900
gaaggatcga gcacgaataa aggtaatcta agagatttca tgaacgttta ttatgccaga      960
tatcacaaca tttccacacc ctggaacggc gatattgaat ccggcatcga acggttaaca     1020
```

```
aagatgctag tactagttga agagtctctc gccaataaga acagggctt tagtgttgac      1080 gatgtcgcgc aatccttgaa ttgttctcgc gaagaattca caagagtcta cttaacaaca      1140
tctccagtga gatttcaagt cttaaagcta tatcagaggg ctaagcatgt gtattctgaa      1200
tctttaagag tcttgaaggc tgtgaaatta atgactacag agagctttac tgccgatgaa      1260 gacttttttca agcaatttgg tgccttgatg aacgagtctc aagcttcttg cgataaactt      1320
tacgaatgtt cttgtccaga gattgacaaa atttgttcca ttgctttgtc aaatggatca      1380
tatggttccc gtttgaccgg agctggctgg ggtggttgta ctgttcactt ggttccaggg      1440
ggcccaaatg gcaacataga aaaggtaaaa gaagcccttg ccaatgagtt ctacaaggtc      1500
aagtacccta agatcactga tgctgagctt gaaaatgcta ttatcgtctc taaaccagca      1560
ttgggcagct gtctatatga attataa                                        1587

<210> SEQ ID NO 45
<211> LENGTH: 1587
<212> TYPE: DNA
<213> ORGANISM: Saccharomyces cerevisiae IMW017

<400> SEQUENCE: 45
atgactaaat ctcattcaga agaagtgatt gtacctgagt tcaattctag cgcaaaggaa        60
ttaccaagac cattggccga aaagtgcccg agcataatta agaaatttat aagcgcttat       120
gatgctaaac cggattttgt tgctagatcg cctggtagag tcaatctaat tggtgaacat       180
attgattatt gtgacttctc ggttttacct ttagctattg attttgatat gctttgcgcc       240
gtcaaagttt tgaacgagaa aaatccatcc attaccttaa taaatgctga tcccaaattt       300
gctcaaagga agttcgattt gccgttggac ggttcttatg tcacaattga tccttctgtg       360
tcagactggt ctaattactt taaatgtggt ctccatgttg ctcactcttt tctaaagaaa       420
cttgcaccgg aaaggtttgc cagtgctcct ctggccgggc tgcaagtctt ctgtgagggt       480
gatgtaccaa ctggcagtgg attgtcttct tcggccgcat tcatttgtgc cgttgctttta      540 gctgttgtta aagcgaatat gggccctggt tatcatatgt ccaagcaaaa tttaatgcgt       600
atcacggtcg ttgcagaaca ttatgttggt gttaacaatg gcggtatgga tcaggctgcc       660
tctgtttgcg gtgaggaaga tcatgctcta tacgttgagt tcaaaccgca gttgaaggct       720
actccgttta aatttccgca attaaaaaac catgaaatta gctttgttat tgcgaacacc       780
cttgttgtat ctaacaagtt tgaaaccgcc caaccaact ttaatttaag agtggtagaa       840
gtcactacag ctgcaaatgt tttagctgcc acgtacggtg ttgttttacc ttctggaaaa       900
gaaggatcga gcacgaataa aggtaatcta agagatttca tgaacgttta ttatgccaga       960
tatcacaaca tttccacacc ctggaacggc gatattgaat ccggcatcga acggttaaca      1020
aagatgctag tactagttga agagtctctc gccaataaga acagggctt tagtgttgac      1080 gatgtcgcgc aatccttgaa ttgttctcgc gaagaattca caagagtcta cttaacaaca      1140
tctccagtga gatttcaagt cttaaagcta tatcagaggg ctaagcatgt gtattctgaa      1200
tctttaagag tcttgaaggc tgtgaaatta atgactacag agagctttac tgccgatgaa      1260 gacttttttca agcaatttgg tgccttgatg aacgagtctc aagcttcttg cgataaactt      1320
tacgaatgtt cttgtccaga gattgacaaa atttgttcca ttgctttgtc aaatggatca      1380
tatggttccc gtttgaccgg agctggctgg ggtggttgta ctgttcactt ggttccaggg      1440
ggcccaaatg gcaacataga aaaggtaaaa gaagcccttg ccaatgagtt ctacaaggtc      1500
```

| aagtacccta agatcactga tgctgagctt gaaaatgcta ttatcgtctc taaaccagca | 1560 |
| ttgggcagct gtctatatga attataa | 1587 |

<210> SEQ ID NO 46
<211> LENGTH: 1587
<212> TYPE: DNA
<213> ORGANISM: Saccharomyces cerevisiae IMW018

<400> SEQUENCE: 46

| atgactaaat ctcattcaga agaagtgatt gtacctgagt tcaattctag cgcaaaggaa | 60 |
| ttaccaagac cattggccga aaagtgcccg agcataatta agaaatttat aagcgcttat | 120 |
| gatgctaaac cggattttgt tgctagatcg cctggtagag tcaatctaat tggtgaacat | 180 |
| attgattatt gtgacttctc ggttttacct ttagctattg attttgatat gctttgcgcc | 240 |
| gtcaaagttt tgaacgagaa aaatccatcc attaccttaa taaatgctga tcccaaattt | 300 |
| gctcaaagga agttcgattt gccgttggac ggttcttatg tcacaattga tccttctgtg | 360 |
| tcagactggt ctaattactt taaatgtggt ctccatgttg ctcactcttt tctaaagaaa | 420 |
| cttgcaccgg aaaggtttgc cagtgctcct ctggccgggc tgcaagtctt ctgtgagggt | 480 |
| gatgtaccaa ctggcagtgg attgtcttct tcggccgcat tcatttgtgc cgttgcttta | 540 |
| gctgttgtta aagcgaatat gggccctggt tatcatatgt ccaagcaaaa tttaatgcgt | 600 |
| atcacggtcg ttgcagaaca ttatgttggt gttaacaatg cggtatgga tcaggctgcc | 660 |
| tctgtttgcg gtgaggaaga tcatgctcta tacgttgagt tcaaaccgca gttgaaggct | 720 |
| actccgttta aatttccgca attaaaaaac catgaaatta gctttgttat tgcgaacacc | 780 |
| cttgttgtat ctaacaagtt tgaaaccgcc ccaaccaact ataatttaag agtggtagaa | 840 |
| gtcactacag ctgcaaatgt tttagctgcc acgtacggtg ttgttttacc ttctggaaaa | 900 |
| gaaggatcga gcacgaataa aggtaatcta agagatttca tgaacgttta ttatgccaga | 960 |
| tatcacaaca tttccacacc ctggaacggc gatattgaat ccggcatcga acggttaaca | 1020 |
| aagatgctag tactagttga agagtctctc gccaataaga acagggctt tagtgttgac | 1080 |
| gatgtcgcgc aatccttgaa ttgttctcgc gaagaattca agagtctact taacaaca | 1140 |
| tctccagtga gatttcaagt cttaaagcta tatcagaggg ctaagcatgt gtattctgaa | 1200 |
| tctttaagag tcttgaaggc tgtgaaatta atgactacag agagctttac tgccgatgaa | 1260 |
| gactttttca gcaatttggg tgccttgatg aacgagtctc aagcttcttg cgataaactt | 1320 |
| tacgaatgtt cttgtccaga gattgacaaa atttgttcca ttgctttgtc aaatggatca | 1380 |
| tatggttccc gtttgaccgg agctggctgg ggtggttgta ctgttcactt ggttccaggg | 1440 |
| ggcccaaatg gcaacataga aaaggtaaaa gaagcccttg ccaatgagtt ctacaaggtc | 1500 |
| aagtacccta agatcactga tgctgagctt gaaaatgcta ttatcgtctc taaaccagca | 1560 |
| ttgggcagct gtctatatga attataa | 1587 |

<210> SEQ ID NO 47
<211> LENGTH: 1725
<212> TYPE: DNA
<213> ORGANISM: Saccharomyces cerevisiae CEN.PK 113-7D
<400> SEQUENCE: 47

| atggcagttg aggagaacaa tatgcctgtt gtttcacagc aaccccaagc tggtgaagac | 60 |
| gtgatctctt cactcagtaa agattcccat ttaagcgcac aatctcaaaa gtattccaat | 120 |
| gatgaattga agccggtga gtcagggcct gaaggctccc aaagtgttcc tatagagata | 180 |

```
cccaagaagc ccatgtctga atatgttacc gtttccttgc tttgtttgtg tgttgccttc      240
ggcggcttca tgtttggctg ggataccggt actatttctg ggtttgttgt ccaaacagac      300
tttttgagaa ggtttggtat gaaacataag gatggtaccc actatttgtc aaacgtcaga      360
acaggtttaa tcgtcgccat tttcaatatt ggctgtgcct tggtggtat tatactttcc      420 aaaggtggag atatgtatgg ccgtaaaaag ggtctttcga ttgtcgtctc ggtttatata      480
gttggtatta tcattcaaat tgcctctatc aacaagtggt accaatattt cattggtaga      540
atcatatctg gtttgggtgt cggcggcatc gccgtcttat gtcctatgtt gatctctgaa      600
attgctccaa agcacttgag aggcacacta gtttcttgtt atcagctgat gattactgca      660
ggtatctttt tgggctactg tactaattac ggtacaaaga gctattcgaa ctcagttcaa      720
tggagagttc cattagggct atgtttcgct tggtcattat ttatgattgg cgctttgacg      780
ttagttcctg aatccccacg ttatttatgt gaggtgaata aggtagaaga cgccaagctt      840
tccattgcta agtctaacaa ggtgtcacca gaggatcctg ccgtccaggc agagttagat      900
ctgatcatgg ccggtataga agctgaaaaa ctggctggca atgcgtcctg ggggaatta      960 ttttccacca agaccaaagt atttcaacgt tgttgatgg gtgtatttgt tcaaatgttc      1020
caacaattaa ccggtaacaa ttattttttc tactacggta ccgttatttt caagtcagtt      1080
ggcctggatg attcctttga acatccatt gtcattggtg tagtcaactt tgcctccact      1140
ttctttagtt tgtggactgt cgaaaacttg gggcgtcgta atgtttact tttgggcgct      1200 gccactatga tggcttgtat ggtcatctac gcctctgttg gtgttaccag attatatcct      1260
cacggtaaaa gccagccatc ttctaaaggt gccggtaact gtatgattgt ctttacctgt      1320
ttttatattt tctgttatgc cacaacctgg gcgccagttg cctgggtcat cacagcagaa      1380
tcattcccac tgagagtcaa gtcgaaatgt atggcgttgg cctctgcttc caattgggta      1440
tgggggttct tgattgcatt tttcacccca ttcatcacat ctgccattaa cttctactac      1500
ggttatgtct tcatgggctg tttggttgcc atgtttttt atgtcttttt ctttgttcca      1560
gaaactaaag gcctatcgtt agaagaaatt caagaattat gggaagaagg tgttttacct      1620
tggaaatctg aaggctggat tccttcatcc agaagaggta ataattacga tttagaggat      1680
ttacaacatg acgacaaacc gtggtacaag gccatgctag aataa                    1725
```

<210> SEQ ID NO 48
<211> LENGTH: 1725
<212> TYPE: DNA
<213> ORGANISM: Saccharomyces cerevisiae IMK318

<400> SEQUENCE: 48

```
atggcagttg aggagaacaa tatgcctgtt gtttcacagc aaccccaagc tggtgaagac       60
gtgatctctt cactcagtaa agattcccat ttaagcgcac aatctcaaaa gtattccaat      120
gatgaattga agccggtga gtcagggcct gaaggctccc aaagtgttcc tatagagata      180
cccaagaagc ccatgtctga atatgttacc gtttccttgc tttgtttgtg tgttgccttc      240
ggcggcttca tgtttggctg ggataccggt actatttctg ggtttgttgt ccaaacagac      300
tttttgagaa ggtttggtat gaaacataag gatggtaccc actatttgtc aaacgtcaga      360
acaggtttaa tcgtcgccat tttcaatatt ggctgtgcct tggtggtat tatactttcc      420 aaaggtggag atatgtatgg ccgtaaaaag ggtctttcga ttgtcgtctc ggtttatata      480
gttggtatta tcattcaaat tgcctctatc aacaagtggt accaatattt cattggtaga      540
```

```
atcatatctg gtttgggtgt cggcggcatc gccgtcttat gtcctatgtt gatctctgaa    600
attgctccaa agcacttgag aggcacacta gtttcttgtt atcagctgat gattactgca    660
ggtatctttt tgggctactg tactaattac ggtacaaaga gctattcgaa ctcagttcaa    720
tggagagttc cattagggct atgtttcgct tggtcattat ttatgattgg cgctttgacg    780
ttagttcctg aatccccacg ttatttatgt gaggtgaata aggtagaaga cgccaagctt    840
tccattgcta agtctaacaa ggtgtcacca gaggatcctg ccgtccaggc agagttagat    900
ctgatcatgg ccggtataga agctgaaaaa ctggctggca atgcgtcctg ggggaatta     960 ttttccacca agaccaaagt atttcaacgt tgttgatgg gtgtatttgt tcaaatgttc     1020
caacaattaa ccggtaacaa ttatttttc tactacggta ccgttatttt caagtcagtt     1080
ggcctggatg attcctttga acatccatt gtcattggtg tagtcaactt tgcctccact     1140
ttctttagtt tgtggactgt cgaaaacttg gggcgtcgta aatgtttact tttgggcgct    1200
gccactatga tggcttgtat ggtcatctac gcctctgttg gtgttaccag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcacccca ttcatcacat ctgccattaa cttctactac    1500
ggttatgtct tcatgggctg tttggttgcc atgttttttt atgtcttttt ctttgttcca    1560
gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa              1725
```

<210> SEQ ID NO 49
<211> LENGTH: 1725
<212> TYPE: DNA
<213> ORGANISM: Saccharomyces cerevisiae IMW017

<400> SEQUENCE: 49

```
atggcagttg aggagaacaa tatgcctgtt gtttcacagc aaccccaagc tggtgaagac     60
gtgatctctt cactcagtaa agattcccat ttaagcgcac aatctcaaaa gtattccaat    120
gatgaattga agccggtga gtcagggcct gaaggctccc aaagtgttcc tatagagata    180
cccaagaagc ccatgtctga atatgttacc gtttccttgc tttgtttgtg tgttgccttc    240
ggcggcttca tgtttggctg ggataccggt actatttctg ggtttgttgt ccaaacagac    300 ttttttgagaa ggtttggtat gaaacataag gatggtaccc actatttgtc aaacgtcaga    360
acaggtttaa tcgtcgccat tttcaatatt ggctgtgcct tggtggtat tatactttcc    420 aaaggtggag atatgtatgg ccgtaaaaag ggtctttcga ttgtcgtctc ggtttatata    480
gttggtatta tcattcaaat tgcctctatc aacaagtggt accaatattt cattggtaga    540
atcatatctg gtttgggtgt cggcggcatc gccgtcttat gtcctatgtt gatctctgaa    600
attgctccaa agcacttgag aggcacacta gtttcttgtt atcagctgat gattaatgca    660
ggtatctttt tgggctactg tactaattac ggtacaaaga gctattcgaa ctcagttcaa    720
tggagagttc cattagggct atgtttcgct tggtcattat ttatgattgg cgctttgacg    780
ttagttcctg aatccccacg ttatttatgt gaggtgaata aggtagaaga cgccaagctt    840
tccattgcta agtctaacaa ggtgtcacca gaggatcctg ccgtccaggc agagttagat    900
ctgatcatgg ccggtataga agctgaaaaa ctggctggca atgcgtcctg ggggaatta     960
```

```
ttttccacca agaccaaagt atttcaacgt tgttgatgg gtgtatttgt tcaaatgttc    1020
caacaattaa ccggtaacaa ttattttttc tactacggta ccgttatttt caagtcagtt    1080
ggcctggatg attcctttga acatccatt gtcattggtg tagtcaactt tgcctccact    1140
ttctttagtt tgtggactgt cgaaaacttg gggcgtcgta aatgtttact tttgggcgct    1200
gccactatga tggcttgtat ggtcatctac gcctctgttg gtgttaccag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcaccccca ttcatcacat ctgccattaa cttctactac    1500
ggttatgtct tcatgggctg tttggttgcc atgttttttt atgtcttttt ctttgttcca    1560
gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa                   1725
```

<210> SEQ ID NO 50
<211> LENGTH: 1725
<212> TYPE: DNA
<213> ORGANISM: Saccharomyces cerevisiae IMW018

<400> SEQUENCE: 50

```
atggcagttg aggagaacaa tatgcctgtt gtttcacagc aaccccaagc tggtgaagac      60
gtgatctctt cactcagtaa agattcccat ttaagcgcac aatctcaaaa gtattccaat     120
gatgaattga agccggtga gtcagggcct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg ggtttgttgt ccaaacagac     300
tttttgagaa ggtttggtat gaaacataag gatggtaccc actatttgtc aaacgtcaga     360
acaggtttaa tcgtcgccat tttcaatatt ggctgtgcct ttggtggtat tatactttcc     420
aaaggtggag atatgtatgg ccgtaaaaag gtctttcga ttgtcgtctc ggttatata       480 gttggtatta tcattcaaat tgcctctatc aacaagtggt accaatattt cattggtaga     540
atcatatctg gtttgggtgt cggcggcatc gccgtcttat gtcctatgtt gatctctgaa     600
attgctccaa gcacttgag aggcacacta gtttcttgtt atcagctgat gattactgca     660
ggtatctttt tgggctactg tactaattac ggtacaaaga gctattcgaa ctcagttcaa     720
tggagagttc cattagggct atgtttcgct tggtcattat ttatgattgg cgctttgacg     780
ttagttcctg aatccccacg ttatttatgt gaggtaataa aggtagaaga cgccaagctt     840
tccattgcta agtctaacaa ggtgtcacca gaggatcctg ccgtccaggc agagttagat     900
ctgatcatgg ccgtatagaa gctgaaaaa ctggctggca atgcgtcctg ggggaatta      960 ttttccacca agaccaaagt atttcaacgt tgttgatgg gtgtatttgt tcaaatgttc    1020
caacaattaa ccggtaacaa ttattttttc tactacggta ccgttatttt caagtcagtt    1080
ggcctggatg attcctttga acatccatt gtcattggtg tagtcagctt tgcctccact    1140
ttctttagtt tgtggactgt cgaaaacttg gggcgtcgta aatgtttact tttgggcgct    1200
gccactatga tggcttgtat ggtcatctac gcctctgttg gtgttaccag attatatcct    1260
cacggtaaaa gccagccatc ttctaaaggt gccggtaact gtatgattgt ctttacctgt    1320
```

```
tttatatttt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcacccca ttcatcacat ctgccattaa cttctactac    1500
ggttatgtct tcatgggctg tttggttgcc atgttttttt atgtctttt ctttgttcca     1560 gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa                    1725
```

<210> SEQ ID NO 51
<211> LENGTH: 528
<212> TYPE: PRT
<213> ORGANISM: Saccharomyces cerevisiae CEN.PK 113-7D

<400> SEQUENCE: 51

```
Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
        115                 120                 125

Cys Gly Leu His Val Ala His Ser Phe Leu Lys Lys Leu Ala Pro Glu
    130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ser Ala Ala Phe Ile Cys
                165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
        195                 200                 205

Val Gly Val Asn Asn Gly Gly Met Asp Gln Ala Ala Ser Val Cys Gly
    210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
        275                 280                 285

Ala Ala Thr Tyr Gly Val Val Leu Pro Ser Gly Lys Glu Gly Ser Ser
    290                 295                 300
```

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
            325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
            355                 360                 365

Ser Arg Glu Glu Phe Thr Arg Asp Tyr Leu Thr Thr Ser Pro Val Arg
    370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Glu Ser Phe
                405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
            435                 440                 445

Asp Lys Ile Cys Ser Ile Ala Leu Ser Asn Gly Ser Tyr Gly Ser Arg
450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
515                 520                 525

<210> SEQ ID NO 52
<211> LENGTH: 528
<212> TYPE: PRT
<213> ORGANISM: Saccharomyces cerevisiae IMK318

<400> SEQUENCE: 52

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
        115                 120                 125

Cys Gly Leu His Val Ala His Ser Phe Leu Lys Leu Ala Pro Glu
    130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ala Ala Phe Ile Cys
        165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Ala Glu His Tyr
        195                 200                 205

Val Gly Val Asn Asn Gly Gly Met Asp Gln Ala Ala Ser Val Cys Gly
    210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
        275                 280                 285

Ala Ala Thr Tyr Gly Val Val Leu Pro Ser Gly Lys Glu Gly Ser Ser
    290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
                325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
        355                 360                 365

Ser Arg Glu Glu Phe Thr Arg Val Tyr Leu Thr Thr Ser Pro Val Arg
    370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Glu Ser Phe
                405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
        435                 440                 445

Asp Lys Ile Cys Ser Ile Ala Leu Ser Asn Gly Ser Tyr Gly Ser Arg
    450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
        515                 520                 525

<210> SEQ ID NO 53
<211> LENGTH: 528
<212> TYPE: PRT
<213> ORGANISM: Saccharomyces cerevisiae IMW017

<400> SEQUENCE: 53

Met Thr Lys Ser His Ser Glu Glu Val Ile Val Pro Glu Phe Asn Ser

```
1               5                    10                   15

Ser Ala Lys Glu Leu Pro Arg Pro Leu Ala Glu Lys Cys Pro Ser Ile
                20                   25                  30

Ile Lys Lys Phe Ile Ser Ala Tyr Asp Ala Lys Pro Asp Phe Val Ala
            35                  40                  45

Arg Ser Pro Gly Arg Val Asn Leu Ile Gly Glu His Ile Asp Tyr Cys
        50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
                100                 105                 110

Tyr Val Thr Ile Asp Pro Ser Val Ser Asp Trp Ser Asn Tyr Phe Lys
                115                 120                 125

Cys Gly Leu His Val Ala His Ser Phe Leu Lys Leu Ala Pro Glu
                130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ala Ala Phe Ile Cys
                165                 170                 175

Ala Val Ala Leu Ala Val Val Lys Ala Asn Met Gly Pro Gly Tyr His
                180                 185                 190

Met Ser Lys Gln Asn Leu Met Arg Ile Thr Val Val Ala Glu His Tyr
                195                 200                 205

Val Gly Val Asn Asn Gly Gly Met Asp Gln Ala Ala Ser Val Cys Gly
                210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
                260                 265                 270

Asn Phe Asn Leu Arg Val Val Glu Val Thr Thr Ala Ala Asn Val Leu
                275                 280                 285

Ala Ala Thr Tyr Gly Val Val Leu Pro Ser Gly Lys Glu Gly Ser Ser
                290                 295                 300

Thr Asn Lys Gly Asn Leu Arg Asp Phe Met Asn Val Tyr Ala Arg
305                 310                 315                 320

Tyr His Asn Ile Ser Thr Pro Trp Asn Gly Asp Ile Glu Ser Gly Ile
                325                 330                 335

Glu Arg Leu Thr Lys Met Leu Val Leu Val Glu Glu Ser Leu Ala Asn
                340                 345                 350

Lys Lys Gln Gly Phe Ser Val Asp Asp Val Ala Gln Ser Leu Asn Cys
                355                 360                 365

Ser Arg Glu Glu Phe Thr Arg Val Tyr Leu Thr Thr Ser Pro Val Arg
                370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Glu Ser Phe
                405                 410                 415

Thr Ala Asp Glu Asp Phe Lys Gln Phe Gly Ala Leu Met Asn Glu
                420                 425                 430
```

```
Ser Gln Ala Ser Cys Asp Lys Leu Tyr Glu Cys Ser Cys Pro Glu Ile
        435                 440                 445

Asp Lys Ile Cys Ser Ile Ala Leu Ser Asn Gly Ser Tyr Gly Ser Arg
    450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
                500                 505                 510

Ala Ile Ile Val Ser Lys Pro Ala Leu Gly Ser Cys Leu Tyr Glu Leu
            515                 520                 525

<210> SEQ ID NO 54
<211> LENGTH: 528
<212> TYPE: PRT
<213> ORGANISM: Saccharomyces cerevisiae IMW018

<400> SEQUENCE: 54

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
        115                 120                 125

Cys Gly Leu His Val Ala His Ser Phe Leu Lys Leu Ala Pro Glu
    130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ser Ala Ala Phe Ile Cys
                165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
        195                 200                 205

Val Gly Val Asn Asn Gly Gly Met Asp Gln Ala Ala Ser Val Cys Gly
    210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
```

```
            275                 280                 285
Ala Ala Thr Tyr Gly Val Val Leu Pro Ser Gly Lys Glu Gly Ser Ser
    290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
                325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
        355                 360                 365

Ser Arg Glu Glu Phe Thr Arg Val Tyr Leu Thr Thr Ser Pro Val Arg
    370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Glu Ser Phe
                405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
        435                 440                 445

Asp Lys Ile Cys Ser Ile Ala Leu Ser Asn Gly Ser Tyr Gly Ser Arg
    450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
        515                 520                 525

<210> SEQ ID NO 55
<211> LENGTH: 574
<212> TYPE: PRT
<213> ORGANISM: Saccharomyces cerevisiae CEN.PK 113-7D

<400> SEQUENCE: 55

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125
```

```
Asn Ile Gly Cys Ala Phe Gly Gly Ile Ile Leu Ser Lys Gly Gly Asp
    130                 135                 140
Met Tyr Gly Arg Lys Lys Gly Leu Ser Ile Val Val Ser Val Tyr Ile
145                 150                 155                 160
Val Gly Ile Ile Ile Gln Ile Ala Ser Ile Asn Lys Trp Tyr Gln Tyr
                165                 170                 175
Phe Ile Gly Arg Ile Ile Ser Gly Leu Gly Val Gly Gly Ile Ala Val
            180                 185                 190
Leu Cys Pro Met Leu Ile Ser Glu Ile Ala Pro Lys His Leu Arg Gly
        195                 200                 205
Thr Leu Val Ser Cys Tyr Gln Leu Met Ile Thr Ala Gly Ile Phe Leu
    210                 215                 220
Gly Tyr Cys Thr Asn Tyr Gly Thr Lys Ser Tyr Ser Asn Ser Val Gln
225                 230                 235                 240
Trp Arg Val Pro Leu Gly Leu Cys Phe Ala Trp Ser Leu Phe Met Ile
                245                 250                 255
Gly Ala Leu Thr Leu Val Pro Glu Ser Pro Arg Tyr Leu Cys Glu Val
            260                 265                 270
Asn Lys Val Glu Asp Ala Lys Leu Ser Ile Ala Lys Ser Asn Lys Val
        275                 280                 285
Ser Pro Glu Asp Pro Ala Val Gln Ala Glu Leu Asp Leu Ile Met Ala
    290                 295                 300
Gly Ile Glu Ala Glu Lys Leu Ala Gly Asn Ala Ser Trp Gly Glu Leu
305                 310                 315                 320
Phe Ser Thr Lys Thr Lys Val Phe Gln Arg Leu Leu Met Gly Val Phe
                325                 330                 335
Val Gln Met Phe Gln Gln Leu Thr Gly Asn Asn Tyr Phe Phe Tyr Tyr
            340                 345                 350
Gly Thr Val Ile Phe Lys Ser Val Gly Leu Asp Asp Ser Phe Glu Thr
        355                 360                 365
Ser Ile Val Ile Gly Val Val Asn Phe Ala Ser Thr Phe Phe Ser Leu
    370                 375                 380
Trp Thr Val Glu Asn Leu Gly Arg Arg Lys Cys Leu Leu Leu Gly Ala
385                 390                 395                 400
Ala Thr Met Met Ala Cys Met Val Ile Tyr Ala Ser Val Gly Val Thr
                405                 410                 415
Arg Leu Tyr Pro His Gly Lys Ser Gln Pro Ser Ser Lys Gly Ala Gly
            420                 425                 430
Asn Cys Met Ile Val Phe Thr Cys Phe Tyr Ile Phe Cys Tyr Ala Thr
        435                 440                 445
Thr Trp Ala Pro Val Ala Trp Val Ile Thr Ala Glu Ser Phe Pro Leu
    450                 455                 460
Arg Val Lys Ser Lys Cys Met Ala Leu Ala Ser Ala Ser Asn Trp Val
465                 470                 475                 480
Trp Gly Phe Leu Ile Ala Phe Phe Thr Pro Phe Ile Thr Ser Ala Ile
                485                 490                 495
Asn Phe Tyr Tyr Gly Tyr Val Phe Met Gly Cys Leu Val Ala Met Phe
            500                 505                 510
Phe Tyr Val Phe Phe Val Pro Glu Thr Lys Gly Leu Ser Leu Glu
        515                 520                 525
Glu Ile Gln Glu Leu Trp Glu Glu Gly Val Leu Pro Trp Lys Ser Glu
    530                 535                 540
Gly Trp Ile Pro Ser Ser Arg Arg Gly Asn Asn Tyr Asp Leu Glu Asp
```

Leu Gln His Asp Asp Lys Pro Trp Tyr Lys Ala Met Leu Glu
                565                 570

<210> SEQ ID NO 56
<211> LENGTH: 574
<212> TYPE: PRT
<213> ORGANISM: Saccharomyces cerevisiae IMK318

<400> SEQUENCE: 56

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

```
Gly Thr Val Ile Phe Lys Ser Val Gly Leu Asp Asp Ser Phe Glu Thr
            355                 360                 365
Ser Ile Val Ile Gly Val Val Asn Phe Ala Ser Thr Phe Phe Ser Leu
370                 375                 380
Trp Thr Val Glu Asn Leu Gly Arg Arg Lys Cys Leu Leu Leu Gly Ala
385                 390                 395                 400
Ala Thr Met Met Ala Cys Met Val Ile Tyr Ala Ser Val Gly Val Thr
                405                 410                 415
Arg Leu Tyr Pro His Gly Lys Ser Gln Pro Ser Ser Lys Gly Ala Gly
            420                 425                 430
Asn Cys Met Ile Val Phe Thr Cys Phe Tyr Ile Phe Cys Tyr Ala Thr
            435                 440                 445
Thr Trp Ala Pro Val Ala Trp Val Ile Thr Ala Glu Ser Phe Pro Leu
            450                 455                 460
Arg Val Lys Ser Lys Cys Met Ala Leu Ala Ser Ala Ser Asn Trp Val
465                 470                 475                 480
Trp Gly Phe Leu Ile Ala Phe Phe Thr Pro Phe Ile Thr Ser Ala Ile
                485                 490                 495
Asn Phe Tyr Tyr Gly Tyr Val Phe Met Gly Cys Leu Val Ala Met Phe
            500                 505                 510
Phe Tyr Val Phe Phe Val Pro Glu Thr Lys Gly Leu Ser Leu Glu
            515                 520                 525
Glu Ile Gln Glu Leu Trp Glu Gly Val Leu Pro Trp Lys Ser Glu
530                 535                 540
Gly Trp Ile Pro Ser Ser Arg Arg Gly Asn Asn Tyr Asp Leu Glu Asp
545                 550                 555                 560
Leu Gln His Asp Asp Lys Pro Trp Tyr Lys Ala Met Leu Glu
            565                 570

<210> SEQ ID NO 57
<211> LENGTH: 574
<212> TYPE: PRT
<213> ORGANISM: Saccharomyces cerevisiae IMW017

<400> SEQUENCE: 57

Met Ala Val Glu Glu Asn Asn Met Pro Val Val Ser Gln Gln Pro Gln
1               5                   10                  15
Ala Gly Glu Asp Val Ile Ser Ser Leu Ser Lys Asp Ser His Leu Ser
            20                  25                  30
Ala Gln Ser Gln Lys Tyr Ser Asn Asp Glu Leu Lys Ala Gly Glu Ser
        35                  40                  45
Gly Pro Glu Gly Ser Gln Ser Val Pro Ile Glu Ile Pro Lys Lys Pro
    50                  55                  60
Met Ser Glu Tyr Val Thr Val Ser Leu Leu Cys Leu Cys Val Ala Phe
65              70                  75                  80
Gly Gly Phe Met Phe Gly Trp Asp Thr Gly Thr Ile Ser Gly Phe Val
                85                  90                  95
Val Gln Thr Asp Phe Leu Arg Arg Phe Gly Met Lys His Lys Asp Gly
            100                 105                 110
Thr His Tyr Leu Ser Asn Val Arg Thr Gly Leu Ile Val Ala Ile Phe
        115                 120                 125
Asn Ile Gly Cys Ala Phe Gly Gly Ile Ile Leu Ser Lys Gly Gly Asp
    130                 135                 140
Met Tyr Gly Arg Lys Lys Gly Leu Ser Ile Val Val Ser Val Tyr Ile
145                 150                 155                 160
```

```
Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
                180                 185                 190

Leu Cys Pro Met Leu Ile Ser Glu Ile Ala Pro Lys His Leu Arg Gly
                195                 200                 205

Thr Leu Val Ser Cys Tyr Gln Leu Met Ile Asn Ala Gly Ile Phe Leu
                210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
                260                 265                 270

Asn Lys Val Glu Asp Ala Lys Leu Ser Ile Ala Lys Ser Asn Lys Val
                275                 280                 285

Ser Pro Glu Asp Pro Ala Val Gln Ala Glu Leu Asp Leu Ile Met Ala
                290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
                340                 345                 350

Gly Thr Val Ile Phe Lys Ser Val Gly Leu Asp Asp Ser Phe Glu Thr
                355                 360                 365

Ser Ile Val Ile Gly Val Val Asn Phe Ala Ser Thr Phe Phe Ser Leu
370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
                420                 425                 430

Asn Cys Met Ile Val Phe Thr Cys Phe Tyr Ile Phe Cys Tyr Ala Thr
                435                 440                 445

Thr Trp Ala Pro Val Ala Trp Val Ile Thr Ala Glu Ser Phe Pro Leu
                450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
                500                 505                 510

Phe Tyr Val Phe Phe Phe Val Pro Glu Thr Lys Gly Leu Ser Leu Glu
                515                 520                 525

Glu Ile Gln Glu Leu Trp Glu Glu Gly Val Leu Pro Trp Lys Ser Glu
                530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570
```

<210> SEQ ID NO 58
<211> LENGTH: 574
<212> TYPE: PRT
<213> ORGANISM: Saccharomyces cerevisiae IMW018

<400> SEQUENCE: 58

```
Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
        355                 360                 365

Ser Ile Val Ile Gly Val Val Ser Phe Ala Ser Thr Phe Phe Ser Leu
    370                 375                 380
```

```
Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
        435                 440                 445

Thr Trp Ala Pro Val Ala Trp Val Ile Thr Ala Glu Ser Phe Pro Leu
    450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
            485                 490                 495

Asn Phe Tyr Tyr Gly Tyr Val Phe Met Gly Cys Leu Val Ala Met Phe
            500                 505                 510

Phe Tyr Val Phe Phe Phe Val Pro Glu Thr Lys Gly Leu Ser Leu Glu
        515                 520                 525

Glu Ile Gln Glu Leu Trp Glu Glu Gly Val Leu Pro Trp Lys Ser Glu
    530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570
```